United States Patent
Kendrick et al.

(10) Patent No.: US 10,927,400 B2
(45) Date of Patent: Feb. 23, 2021

(54) PROTEIN STANDARD COMPOSITIONS AND METHODS OF MAKING AND USING THE SAME

(71) Applicant: KENDRICK LABORATORIES, INC., Madison, WI (US)

(72) Inventors: Nancy Kendrick, Monona, WI (US); Jon Johansen, Madison, WI (US); Matthew Hoelter, Columbus, WI (US); Andrew Koll, Madison, WI (US); Ginny Powers, Madison, WI (US)

(73) Assignee: KENDRICK LABORATORIES, INC., Madison, WI (US)

( * ) Notice: Subject to any disclaimer, the term of this patent is extended or adjusted under 35 U.S.C. 154(b) by 67 days.

(21) Appl. No.: 15/808,006

(22) Filed: Nov. 9, 2017

(65) Prior Publication Data

US 2018/0127802 A1   May 10, 2018

Related U.S. Application Data

(60) Provisional application No. 62/419,588, filed on Nov. 9, 2016.

(51) Int. Cl.

| | |
|---|---|
| *A61K 38/43* | (2006.01) |
| *A61K 38/45* | (2006.01) |
| *C07K 14/435* | (2006.01) |
| *C07K 16/40* | (2006.01) |
| *C12Q 1/48* | (2006.01) |
| *G01N 33/561* | (2006.01) |
| *C12N 9/12* | (2006.01) |
| *C07K 16/18* | (2006.01) |

(52) U.S. Cl.
CPC .............. *C12Q 1/485* (2013.01); *C07K 16/40* (2013.01); *C12N 9/12* (2013.01); *C12Y 207/10001* (2013.01); *G01N 33/561* (2013.01); *C07K 2317/30* (2013.01); *G01N 2440/14* (2013.01)

(58) Field of Classification Search
CPC .......................... C12N 9/12; C12Y 207/10001; G01N 33/561; G01N 2440/14; C07K 16/40; C07K 2317/30; C12Q 1/485
See application file for complete search history.

(56) References Cited

U.S. PATENT DOCUMENTS

2005/0003450 A1*   1/2005 Rush ...................... C07K 14/47
435/7.1

OTHER PUBLICATIONS

Chen et al. The effects of N-ethylmaleimide on the phosphorylation and aggregation of insulin receptors in the isolated plasma membranes of 3T3-F442A adipocytes. J.B.C. 1986, vol. 261, No. 2, pp. 902-908. (Year: 1986).*
Wu et al. Studies of Phosphoproteomic Changes Induced by Nucleophosmin-Anaplastic Lymphoma Kinase (ALK) Highlight Deregulation of Tumor Necrosis Factor (TNF)/Fas/TNF-related Apoptosis-induced Ligand Signaling Pathway in ALK-positive . . . Mol. Cell. Proteomics. 2010, vol. 9, pp. 1616-1632. (Year: 2010).*
Huang et al. Anaplastic Lymphoma Kinase (ALK) Receptor Tyrosine Kinase: A Catalytic Receptor with many Faces. Int. J. Mol. Sci. 2018, vol. 19, pp. (Year: 2018).*
Lou et al. The first three domains of the insulin receptor differ structurally from the insulin-like growth factor 1 receptor in the regions governing ligand specificity. PNAS, vol. 2006, vol. 103, pp. 12429-12434. (Year: 2006).*
Anderson, L., et al., "High resolution two-dimensional electrophoresis of human plasma proteins," Proc Natl Acad Sci U S A 1977, 74:5421-5425.
Burgess-Cassler, A. et al., "Computerized quantitative analysis of coomassie-blue-stained serum proteins separated by two-dimensional electrophoresis," Clin Chem 1989, 35:2297-2304.
Kendrick, N. et al., "Preparation of a phosphotyrosinylated protein standard for 2D gel western blotting," Presentation from Nov. 9, 2015, pp. 1-16.
Laemmli, U. K., "Cleavage of structural proteins during the assembly of the head of bacteriophage T4," Nature 1970, 227:680-685.
Lemmon, M. A., et al., "Cell signaling by receptor tyrosine kinases," Cell 2010, 141:1117-1134.
Liu, B. A., et al., "The human and mouse complement of SH2 domain proteins—establishing the boundaries of phosphotyrosine signaling," Mol Cell 2006, 22:851-868.
Liu, B. A., et al., "The SH2 domain-containing proteins in 21 species establish the provenance and scope of phosphotyrosine signaling in eukaryotes," Sci Signal 2011, 4:ra83.
Liu, H. et al., "Disulfide bond structures of IgG molecules: structural variations, chemical modifications and possible impacts to stability and biological function," MAbs 2012, 4:17-23.
O'Farrell, P.H., "High resolution two-dimensional electrophoresis of proteins," J Biol Chem 1975, 250:4007-4021.
ProQinase recombinant human active protein kinase ALK, product No. 1048-0000-1, Certificate of Analysis, pp. 1-2.
Roskoski, R., "Anaplastic lymphoma kinase (ALK): structure, oncogenic activation, and pharmacological inhibition," Pharmacol Res 2013, 68:68-94.

* cited by examiner

*Primary Examiner* — Shafiqul Haq
(74) *Attorney, Agent, or Firm* — Quarles & Brady LLP

(57) ABSTRACT

The invention generally relates to protein standard compositions and methods of making the same. Also contemplated are kits including the protein standard compositions or kits for making the protein standard compositions and methods of using the protein standard compositions to quantify the abundance of a phosphorylated protein in a sample.

11 Claims, 23 Drawing Sheets

Specification includes a Sequence Listing.

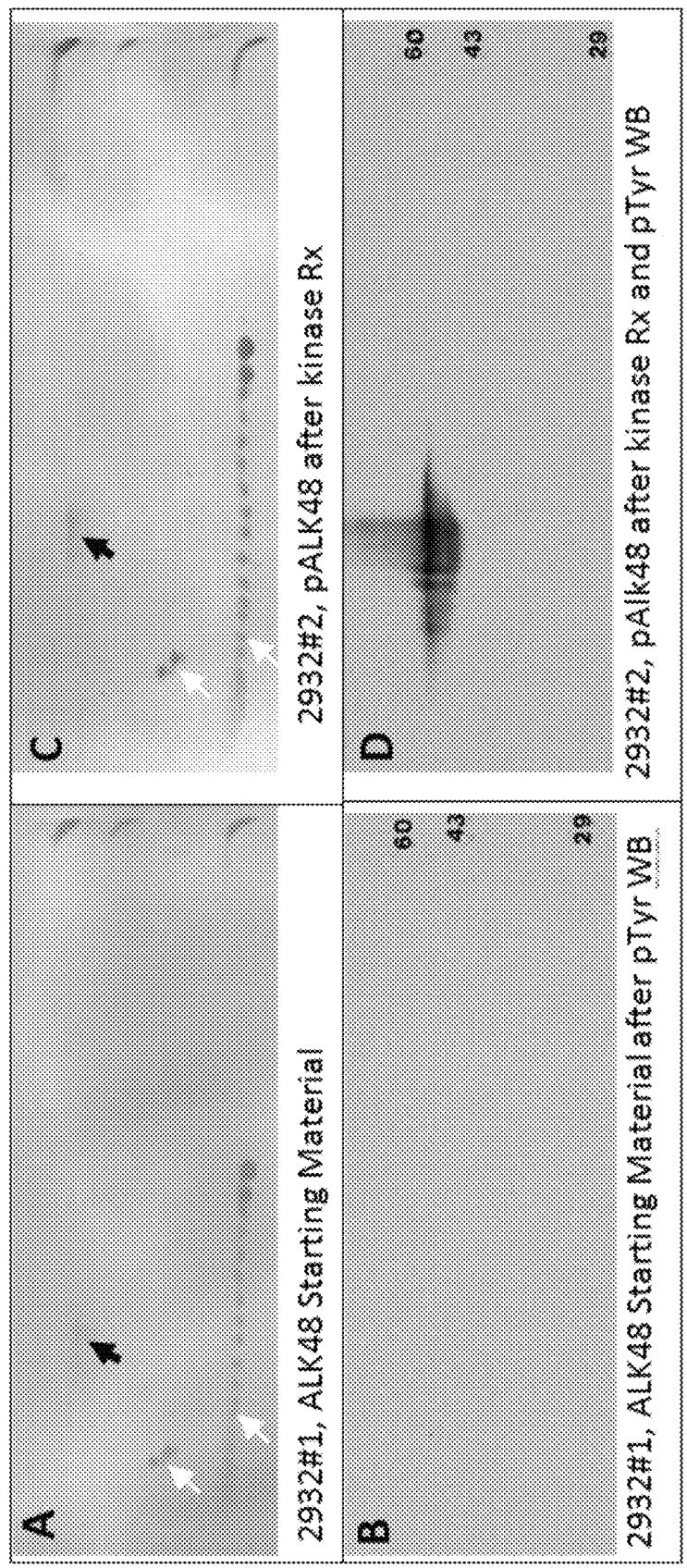

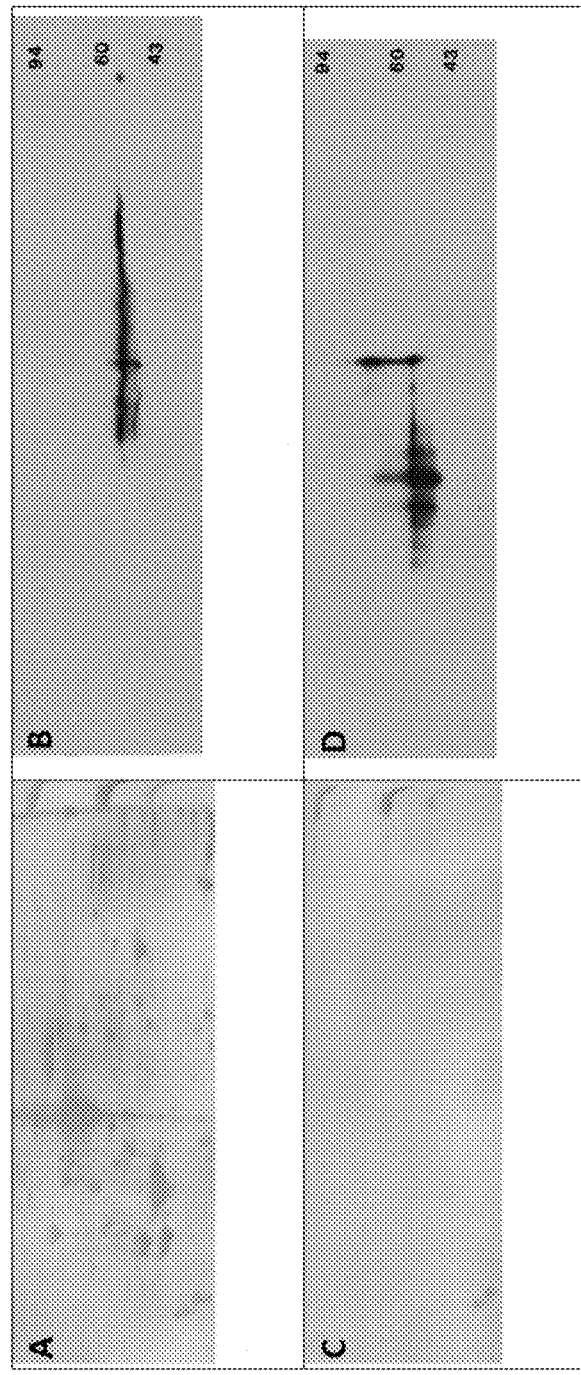

Fig. 6 p3016, 2D Images and quantification of 3' & 10' films
pE/pA ratios: X, 2X, 0.5X and X (double load both)

| #1: 10 ul EGFR/ 1 ng pA (Ratio = X) | | #2: 10 ul EGFR/ 1 ng pA (Ratio = X) | |
|---|---|---|---|
| 3 min | 10 min | 3 min | 10 min |
| EGFR-L1 | 858,367 | 1,864,688 | EGFR-L1 | 410,854 | 874,891 |
| pA-L1 | 369,504 | 939,838 | pA-L1 | 294,586 | 910,336 |
| Ratio | 232 | 198 | Ratio | 139 | 96 |

| #3: 20 ul EGFR, 1 ng pA (Ratio = 2X) | | #4: 20 ul EGFR, 1 ng pA (Ratio = 2X) | |
|---|---|---|---|
| 3 min | 10 min | 3 min | 10 min |
| EGFR-L1 | 2,761,023 | 5,372,107 | EGFR-L1 | 4,418,428 | 7,309,965 |
| pA-L1 | 1,032,940 | 2,246,275 | pA-L1 | 819,690 | 1,752,477 |
| Ratio | 267 | 239 | Ratio | 539 | 417 |

Fig. 6 cont.

| #5: 10 ul EGFR, 2 ng pA (Ratio = 0.5X) | | #6: 10 ul EGFR, 2 ng pA (Ratio = 0.5X) | |
|---|---|---|---|
| 3 min | 10 min | 3 min | 10 min |
| EGFR-L1 | 810,905 | EGFR-L1 | 1,706,261 | EGFR-L1 | 1,718,883 | EGFR-L1 | 3,296,128 |
| pA-L1 | 1,567,715 | pA-L1 | 3,079,783 | pA-L1 | 1,880,101 | pA-L1 | 3,811,654 |
| Ratio | 52 | Ratio | 55 | Ratio | 91 | Ratio | 86 |
| #7: 20 ul EGFR, 2 ng pA (Ratio = X, double load) | | #8: 20 ul EGFR, 2 ng pA (Ratio = X, double load) | |
| 3 min | 10 min | 3 min | 10 min |
| EGFR-L1 | 4,175,056 | EGFR-L1 | 6,633,112 | EGFR-L1 | 3,881,129 | EGFR-L1 | 7,064,838 |
| pA-L1 | 1,745,918 | pA-L1 | 3,309,934 | pA-L1 | 2,240,357 | pA-L1 | 4,331,457 |
| Ratio | 239 | Ratio | 200 | Ratio | 173 | Ratio | 163 |

Fig. 7 p3017#1-8, 2D images and quantification of 3' & 10' films, EGFR-L2/pA-L2 ratios: X, 2X, 0.5X and X (double load both)

| #1: 10 ul EGFR, 1 ng pA (Ratio = X) | | | #2: 10 ul EGFR, 1 ng pA (Ratio = X) | | |
|---|---|---|---|---|---|
| 3 min | | 10 min | 3 min | | 10 min |
| EGFR-L2 | 182,147 | 401,411 | EGFR-L2 | 400,936 | 1,209,531 |
| pA-L2 | 351,782 | 979,354 | pA-L2 | 719,111 | 2,167,918 |
| Ratio | 52 | 41 | Ratio | 56 | 56 |
| #3: 20 ul EGFR, 1 ng pA (Ratio = 2X) | | | #4: 20 ul EGFR, 1 ng pA (Ratio = 2X) | | |
| 3 min | | 10 min | 3 min | | 10 min |
| EGFR-L2 | 156,198 | 385,040 | EGFR-L2 | 501,508 | 1,457,235 |
| pA-L2 | 245,624 | 507,519 | pA-L2 | 516,498 | 1,283,738 |
| Ratio | 64 | 76 | Ratio | 97 | 114 |

Fig. 7 cont.

| #5: 10 ul EGFR, 2 ng pA (Ratio = 0.5X) | | | #6: 10 ul EGFR, 2 ng pA (Ratio = 0.5X) | | |
|---|---|---|---|---|---|
| 3 min | 10 min | | 3 min | 10 min | |
| EGFR-L2 | 180,675 | 371,348 | EGFR-L2 | 210,808 | 683,256 |
| pA-L2 | 573,050 | 1,508,084 | pA-L2 | 2,040,416 | 4,825,933 |
| Ratio | 32 | 25 | Ratio | 10 | 14 |

| #7: 20 ul EGFR, 2 ng pA (Ratio = X) | | | #8: 20 ul EGFR, 2 ng pA (Ratio = X) | | |
|---|---|---|---|---|---|
| 3 min | 10 min | | 3 min | 10 min | |
| EGFR-L2 | 435,597 | 2,167,940 | EGFR-L2 | 1,333,349 | 3,586,746 |
| pA-L2 | 876,377 | 3,097,656 | pA-L2 | 3,007,997 | 5,959,296 |
| Ratio | 50 | 70 | Ratio | 44 | 60 |

Fig. 15

ALK Recombinant Fusion Protein Amino Acid Sequence

MDYKDDDDKD YKDDDDKDYK DDDDKDYKDD DDKSGGGGSLQ ANQMELQSPE YKLSKLRTST
IMTDYNPNY FAGKTSSISD LKEVPRKNIT LIRGLGHGAF GEVYEGQVSG MPNDPSPLQV
AVKTLPEVCS EQDELDFLME ALIISKFNHQ NIVRCIGVSL QSLPRFILLE LMAGGDLKSF
LRETRPRPSQ PSSLAMLDLL HIVARDIACGC QYLEENHFIH RDIAARNCLL TCPPGRVAK
IGDFGMARDI YRASYYRKGG CAMLPVKWMP PEAFMEGIFT SKTDTWSFGV LLWEIFSLGY
MPYPSKSNQE VLEFVTSGGR MDPPKNCPGP VYRIMTQCWQ HQPEDRPNFA IILERIEYCT
QDPDVINTAL PIEYGPLVEE EEKVPVRPKD PEGVPPLLVS QQAKREERSK LLEHHHHHH
HH 1-218: GST  Green: FLAG  Red: HIS6-tag & also tyrosine (Y)  blue: ALK fragment A. 2 ng pA + 10 ug pE
lot 3 (3028#3)

B. 2 ng pA + 10 ug pE
lot 3 + 150 ug tumor L3
(3028#7)

C. 2 ng pA + 50 ug pE
lot 3 + 150 ug tumor L4
(3029#5)

PROTEIN STANDARD COMPOSITIONS AND METHODS OF MAKING AND USING THE SAME

CROSS-REFERENCE TO RELATED PATENT APPLICATIONS

The present application claims the benefit of priority to United States Provisional Patent Application No. 62/419,588, filed on Nov. 9, 2016, the content of which is incorporated herein by reference in its entirety.

SEQUENCE LISTING

This application is being filed electronically via EFS-Web and includes an electronically submitted Sequence Listing in .txt format. The .txt file contains a sequence listing entitled "2017-11-09 6386-00002_ST25.txt" created on Nov. 9, 2017 and is 29,994 bytes in size. The Sequence Listing contained in this .txt file is part of the specification and is hereby incorporated by reference herein in its entirety.

INTRODUCTION

Protein phosphorylation is an important post-translational modification that regulates protein function in a broad range of cellular activities. For example, receptor tyrosine kinase proteins (RTK), such as epidermal growth factor receptor (EGFR), are known to be activated by transphosphorylation of tyrosine residues via kinase domains after these membrane proteins dimerize. Phosphotyrosines (pTyr) then serve as docking sites for cytosolic proteins containing corresponding SH2 domains. Subsequent interactions between the docked proteins give rise to a host of important downstream interactions including cell division.

Abnormal protein phosphorylation events, including in the EGFR pathway, have been implicated in many disease states including several types of cancer. Given the importance of protein phosphorylation in many types of disease, determining the phosphorylation status of an individual protein or proteins has become a critical step in developing new disease treatments and understanding the molecular underpinnings of disease.

Common methods for phosphorylation analyses include the use of phospho-specific antibodies, mass spectrometry, and $^{32}$P radioactive labeling. Although current phosphorylation analyses methodologies have increased our understanding of the role of protein phosphorylation in many disease states, these methodologies suffer from a number of limitations. One important limitation to current methodologies is that they often fail to provide quantitative data or data that can be accurately compared between samples. For example, one major problem with western blotting using phospho-specific antibodies is that pictorial results from even small groups of samples are cumbersome to tabulate and present. A second problem is that the ECL light emission, while imparting high sensitivity, also varies dramatically over the first couple of hours of film or scanner exposure. Thus, western blot density results vary with conditions.

Given these limitations, there remains a need in the art for new protein standard compositions and methodologies that may be used to reproducibly determine the normalized abundance of a phosphorylated protein in a sample. Such abundances may, for example, facilitate the accurate comparison of a particular phosphorylated protein across two or more samples.

SUMMARY

In one aspect, protein standards are provided. The protein standards may include a protein including a phosphorylated amino acid residue and a cysteine residue comprising a blocked sulfhydryl group. In some embodiments, the protein of the present invention is a kinase domain from an Anaplastic Lymphoma Kinase (ALK) protein. The ALK kinase domain may include SEQ ID NO: 1 (human ALK protein fragment from ProQinase L1066-51437), a polypeptide having at least 60%, 70%, 75%, 80%, 85%, 90%, 95%, 98%, or 99% sequence identity to SEQ ID NO: 1, SEQ ID NO: 2 (tagged version human ALK protein fragment from ProQinase L1066-51437), or a polypeptide having at least 60%, 70%, 75%, 80%, 85%, 90%, 95%, 98%, or 99% sequence identity to SEQ ID NO: 2.

In another aspect, methods of making a protein standard are provided. The methods may include (i) phosphorylating a starting protein including an amino acid residue capable of being phosphorylated and a cysteine residue to produce a phosphorylated protein, and (ii) contacting the phosphorylated protein with a sulfhydryl blocking agent.

In another aspect, methods for quantitating the abundance of a phosphorylated protein in a sample are also provided. The methods may include (a) obtaining the sample, and (b) adding a predetermined amount of any one of the protein standards disclosed herein to the sample to produce a spiked sample. Optionally, the methods may further include any one of, or any combination of the following steps: (c) separating the proteins in the spiked sample to produce a separated sample, (d) detecting the phosphorylated protein in the separated sample to produce a phosphoprotein signal, (e) detecting the protein standard in the separated sample to produce a protein standard signal, (f) determining the abundance of the phosphorylated protein in the sample based on the phosphoprotein signal and the protein standard signal. In some embodiments, the methods may further include extracting the sample prior to the separation step (c).

In a further aspect, kits are provided. The kits may include any one of the protein standards disclosed herein. Alternatively, the kits may include (i) a starting protein comprising an amino acid residue capable of being phosphorylated and a cysteine residue and (ii) a sulfhydryl blocking agent.

BRIEF DESCRIPTION OF THE DRAWINGS

FIG. 1 shows 2D western blots from 1 μg Alk48 starting material before and after kinase reaction. (A) and (C): Coomassie stained blots showing total protein pattern. (B) and (D): corresponding images obtained from pTyr western blotting of (A) and (C): Black arrows in the top row indicate the ALK48 starting material. White arrows indicate internal IEF markers, tropomyosin doublet, lower spot 33 kDa, pI 5.2, and a train of carbamylated CPK pI markers. (B): No western blot signal is observed for ALK48 before the kinase reaction. (D): A strong western blot signal is observed after the kinase reaction (30 sec exposure).

FIG. 2 shows the apparent pI of pALK48 varies with sample loaded in the 2D gel. (A): Total protein patterns for 100 ng of pALK48 (lot 1)+200 μg of human lung tumor sample. (C): Total protein pattern for 100 ng of pALK48 alone. (B) and (D): Films showing the corresponding pTyr western blots.

FIG. 3 shows the effect of cysteine blockage. 2D gels were loaded with 20 ng of pAlk48 or pAlk48-SB (lot 2). (A) and (C) show overlay images of Coomassie-stained blots aligned to the p-Tyr film via the internal tropomyosin std, pI 5.2, 33 kDa; (B) and (D) show ECL film images before and after iodoacetamide reaction.

FIG. 4 shows images (10 min films, desktop scans) for 1D SDS PAGE pTyr western blots. The GP48 gels were loaded with pALK48-SB (Lot 1) and EGFR test sample (Lot 10852). Table 1 shows the loading scheme for 1D SDS PAGE pTyr western blots in FIG. 4.

FIG. 5 shows plots of band density versus ng pALK48-SB for the 1D triplicate gels of GP48 #1-3. The curves start to level off at 4 ng (not shown). $R^2$ values are ≥0.9590 in every case for the range 0 to 2 ng pALK48-SB per lane. The 1D gel images are shown in FIG. 4.

FIG. 6 shows western blot images, spot densities and ratios for p3016 #1-8 loaded with pAlk48-SB (pA) lot 1+pEGFR (lot 10852). The pTyr-EGFR spot is on the upper right at 175 kDa; the pA spot is the lower left. Results for FIG. 6 are tabulated in Tables 6 and 7.

FIG. 7 shows western blot images, spot densities and ratios for p3017 #1-8 loaded with pAlk48-SB (pA) lot 2 and EGFR (lot 13639). The pTyr-EGFR spot is always on the upper right at 175 kDa; the pALK48-SB spot is on the lower left. Results for FIG. 7 are tabulated in Tables 8 and 9.

FIG. 8 shows an image of western blot films showing results from four 1D SDS PAGE gels identically loaded with Group 1 samples (40 μg protein/lane). Fresh aliquots of each sample were thawed and kept on ice prior to loading gels run on the same day. Each gel was western blotted with a different antibody as indicated. Arrows indicate pTyr bands.

FIG. 9 shows 2D SDS PAGE pTyr western blots for lung tumor samples L1-L6 and three lung control samples received and run in 2011. The PY20 pTyr antibody was used at a dilution of 1:1000 in combination with Kodak XAR film. Gels for L1, L2, L3, L3-NAT, L4 and L6 were run on 3/10/11; for L5 on 3/29/11, asthmatic control on 4/26/11 and tuberculosis control on 5/12/11. Red (light grey) arrows indicate spots identified as tyrosine kinase proteins; blue (dark grey) arrows indicate unknown pTyr-proteins present in control samples.

FIG. 10 shows a comparison of pTyr 2D western blot (WB) patterns from L3 and L5 tumor samples with those from EGFR and PDGFR western blots. The Coomassie stained patterns shows human albumin used to line up the patterns either by non-specific binding or by negative staining. Another high-MW point for lining up the gels is a small amount of RTK material hangs up on the extreme basic end of the gel.

FIG. 13 shows putative degradation products (arrows). New ~30 kDa pTyr spots appeared after treatment of Tumor L3 and L5 at 37° C. for 3 hrs with and without deglycosylation enzymes. (A) and (C). These new protein spots react strongly with the pTyr antibody; they are not visible with silver staining. A similar strong pTyr spot appeared once for Tumor L3 in 2014 (D) and also was present in Tumor L7 (E) but not L7-NAT (F).

Figure 14:
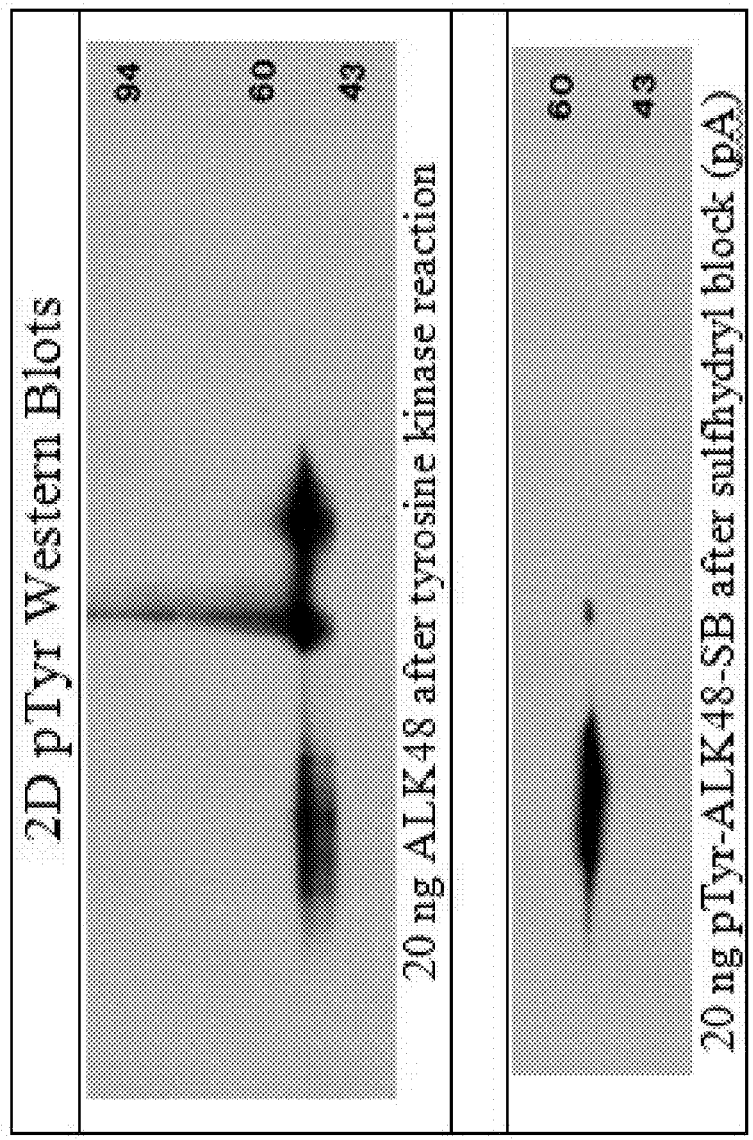

FIG. 14 shows patterns obtained after 2D SDS PAGE western blotting of 20 ng of recombinant 48 kDa ALK fragment subjected to a tyrosine kinase reaction in vitro with ATP at 30° C. for 30 min (top panel, 2989 #5), and after the second step of alkylation with iodoacetamide to block sulfhydryl groups (bottom panel, 2996 #1).

FIG. 15 shows results of analysis for phosphotyrosine residues in ALK48-SB (SEQ ID NO: 2) using mass spectrometry. ALK fragment (SEQ ID NO: 2) tyrosines 69 and 256 were found to be phosphorylated.

Figure 16:
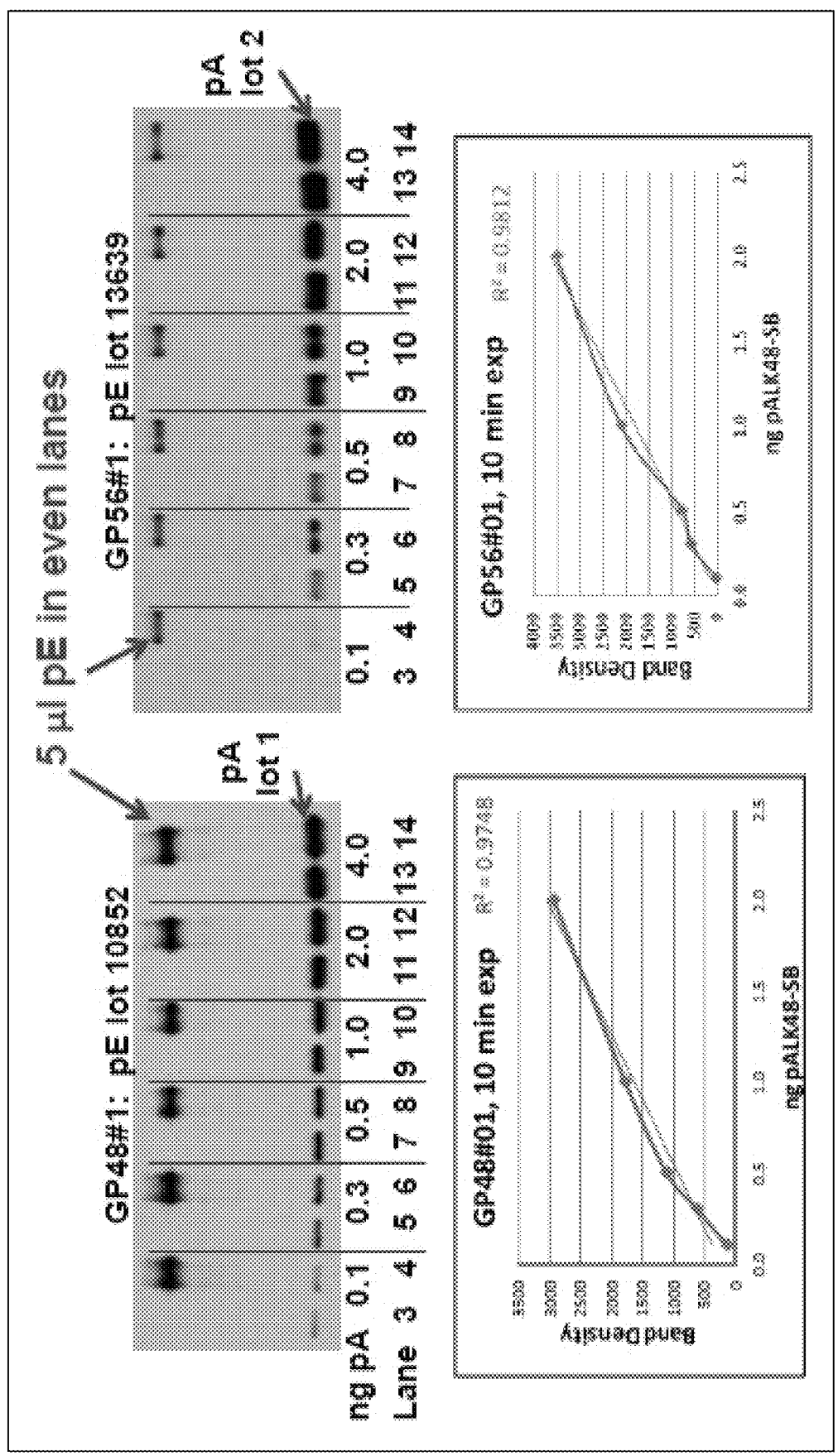

FIG. 16 shows images of cropped 1D films showing pA from two different lots loaded in increasing amounts from 0.1 to 4.0 ng/lane in duplicate in lanes 3-14. A fixed amount, 5 μl, of pE, positive control, was loaded in even lanes. TotalLab software was used to determine pA and pE band densities for both 3 minute (not shown) and 10 minute film exposures. Plots of pA band density versus load are shown for the 10 minute exposures.

Figure 17:
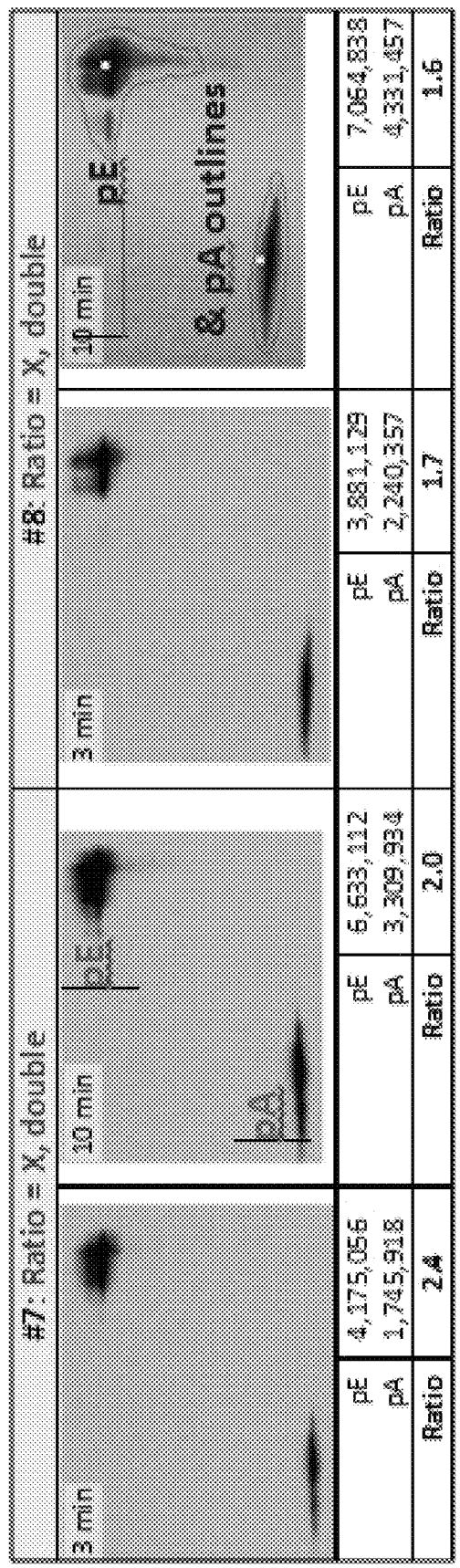

FIG. 17 shows images of 3 and 10 minute pTyr western blot films (p3016) showing pTyr-EGFR (pE) and pA standard along with spot density values and ratios. Spot outlines shown for gel #8 (Ratio=X, double loads) were propagated to the other images using Progenesis SameSpots software for images obtained with a calibrated laser densitometer.

Figure 18:
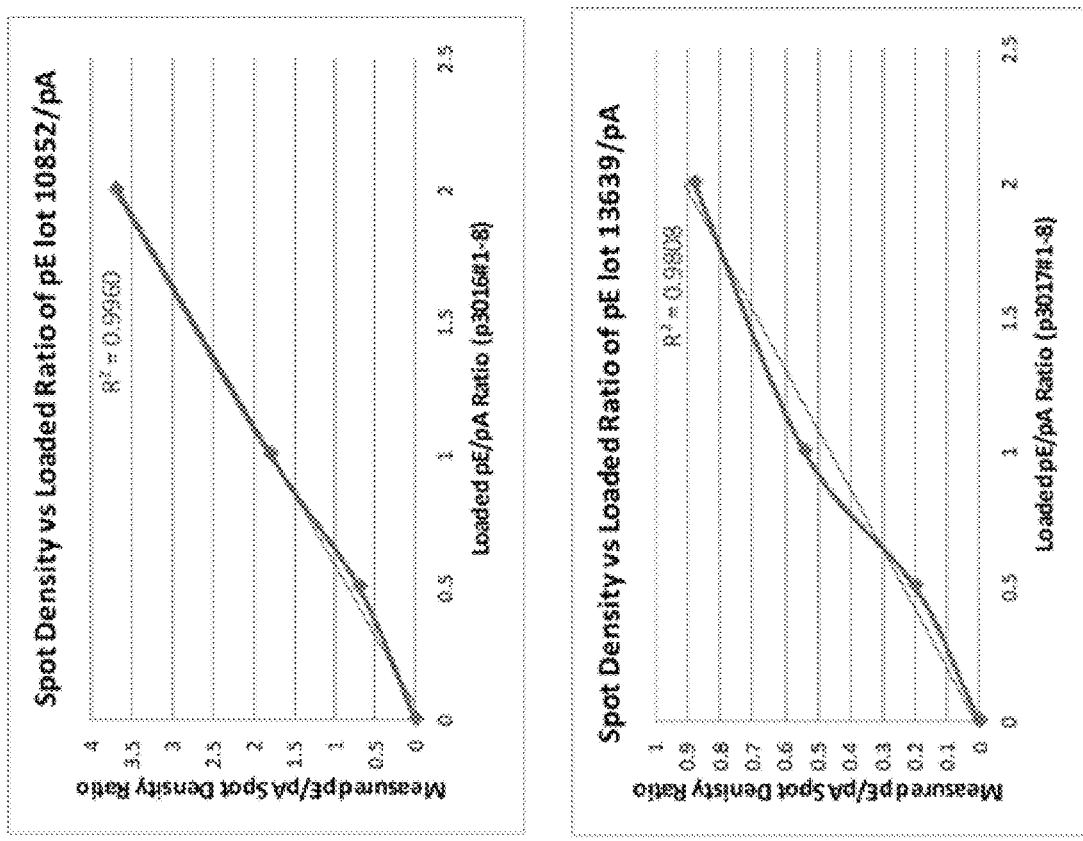

FIG. 18 shows two plots showing spot density ratios for 0.5X (n=2 gels, 4 films), X (n=4 gels, 8 films) and 2X (n=2 gels, 4 films) for pE lots 10852 (p3016 #1-8) and 13639 (p3017 #1-8).

Figure 19A:
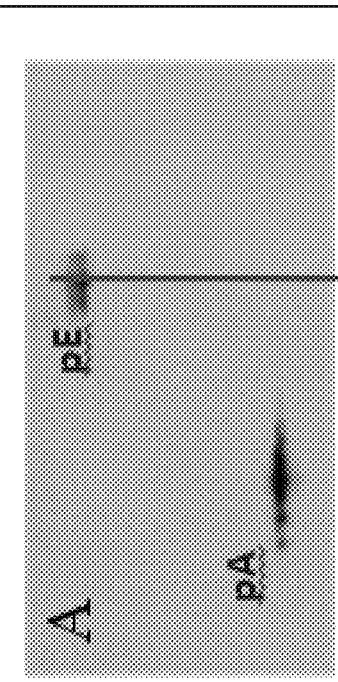
Figure 19B:
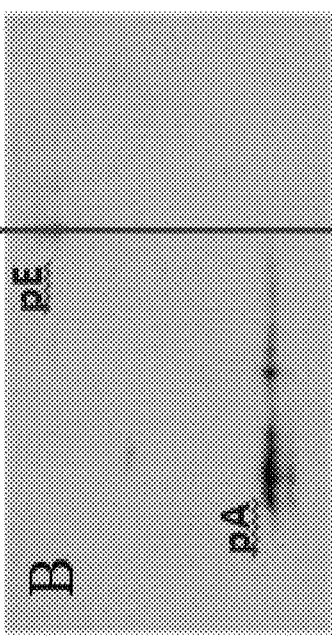
Figure 19C:
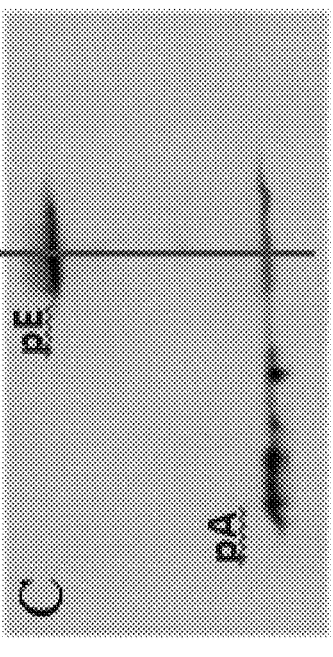

FIG. 19 shows a comparison of pA patterns (3 min films) in the presence of: (A): no added tumor lysate, (B): 150 ug of tumor L3, and (C): 150 ug of tumor L4. Substances in the tumor lysate, possibly proteins with SH2 domains, are causing the pA to streak during IEF. The pE lot 3 in this case, used as a pI marker, was an in-house combination of lots 10852 and 13639.

Figure 20:
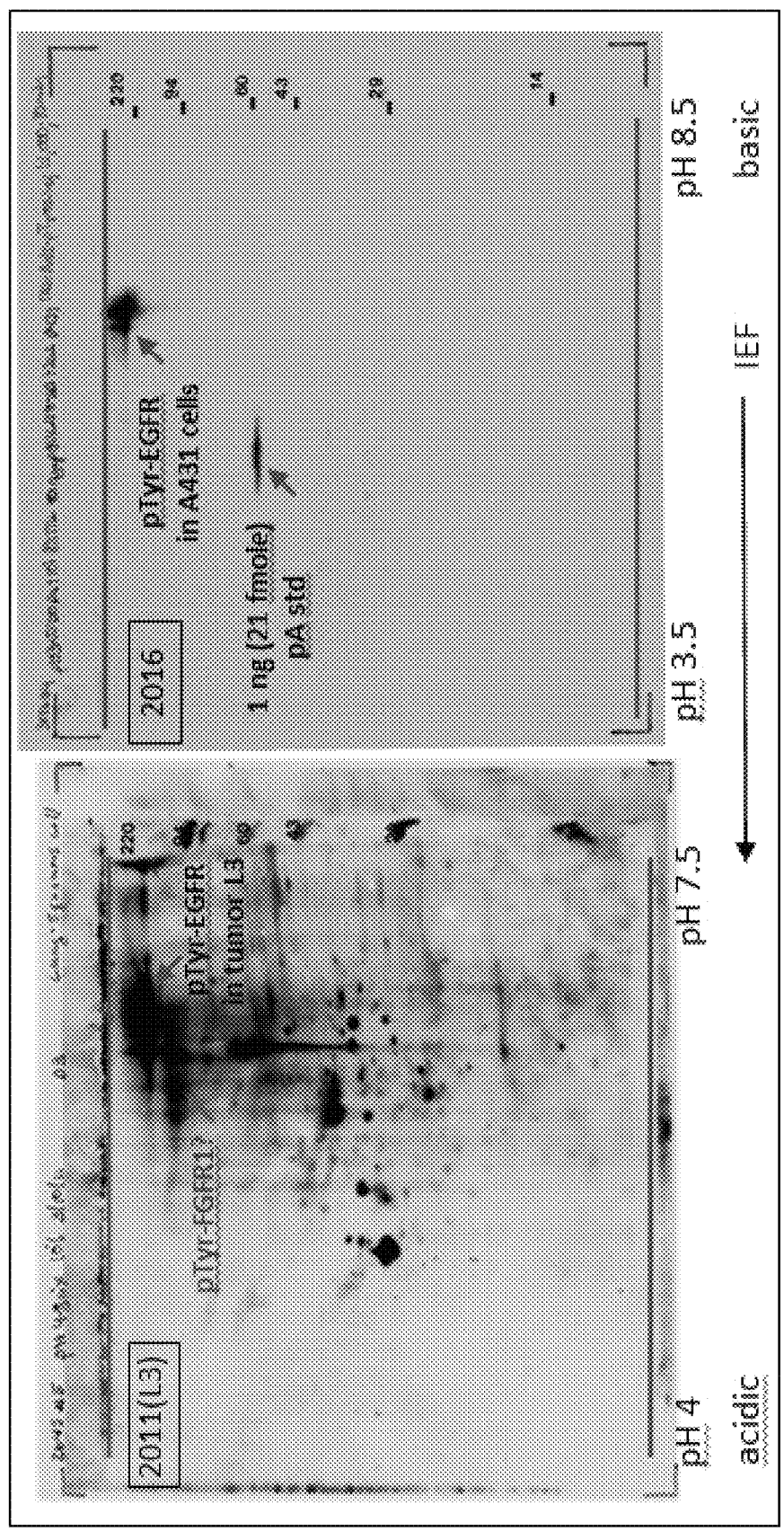

FIG. 20 shows 2D SDS PAGE pTyr western blot pattern from human tumor L3 (2011, left, 30 minute exposure) compared to that of a mixture of pE plus 1 ng pA (2016, right, 10 minute exposure). Red lines determined from the Coomassie pattern mark the top and dye front of the 2D gels. The IEF ampholine mixture varied between the two runs as indicated by the pH scale. Red arrows mark pTyr-EGFR and pTyr-Alk48; the green arrow on the left marks a low abundance, unknown pTyr-RTK.

DETAILED DESCRIPTION

The present inventors provide compositions, methods, and kits that may be used to quantitate a phosphorylated protein in a sample. In the Examples, the present inventors found that phosphorylated protein standards tended to streak in an irreproducible way when analyzed using protein analysis methods such as gel electrophoresis. Such irreproducible behavior exhibited by the phosphorylated protein standard makes it difficult to interpret the results of the protein analysis and makes it unlikely that such protein analyses could meet strict GLP/GMP documentation requirements.

Surprisingly, however, the present inventors found that the irreproducible behavior exhibited by a phosphorylated protein standard could be alleviated or eliminated by blocking the sulfhydryl groups of the cysteine residues within the phosphorylated protein standard. Without being bound by theory, the present inventors hypothesize that by blocking the sulfhydryl groups of cysteine residues within the phosphorylated protein standard, the phosphorylated protein standard is less likely to dimerize and/or aggregate causing less streaking and irreproducible behavior in protein analyses.

In one aspect of the present invention, protein standards are provided. The protein standards may include a protein including a phosphorylated amino acid residue and a cysteine residue with a blocked sulfhydryl group. Optionally, the protein standards may further include a buffer. Suitable buffers for proteins are well known in the art and may include, without limitation, phosphate-buffered saline (PBS) buffers, TRIS buffers (such as Tris buffered saline (TBS)), HEPES buffers, or MOPS buffers The buffer may also be a denaturing buffer including, without limitation, sodium dodecyl sulphate (SDS) and/or beta-mercaptoethanol.

As used herein, the terms "protein" or "polypeptide" or "peptide" may be used interchangeably to refer to a polymer of amino acids. A "protein" as contemplated herein typically comprises a polymer of naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine).

The proteins contemplated herein may be further modified in vitro or in vivo to include non-amino acid moieties. These modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation, lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a non-enzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine) are also included.

The protein of the present invention may be within a particular molecular weight range. The protein may be between 5 and 250 kilodaltons or within any range therein. In some embodiments, the protein has a molecular weight between 40 and 60 kilodaltons.

As used herein, a "phosphorylated amino acid residue" refers to serine, threonine, histidine, or tyrosine amino acid residues that have side chains that are phosphorylated. The protein of the present invention may have from 1-20 phosphorylated amino acid residues or any range therein. In some embodiments, the protein includes 2-18 phosphorylated amino acid residues. In some embodiments, the protein includes 2-18 phosphorylated tyrosine residues.

The protein of the present invention may include a cysteine residue including a blocked sulfhydryl group. As used herein, a "blocked sulfhydryl group" refers to a sulfhydryl group that has been modified to prevent the ability of the sulfhydryl group to form disulfide bonds with another sulfhydryl group. Several reagents may be used to block cysteine sulfhydryl groups including, without limitation, N-Ethylmaleimide (NEM), Methyl methanethiosulfonate (MMTS), EMCA, or iodoacetamide. Each of these reagents modifies the sulfhydryl group with a different blocking moiety (NEM creates a thioether (irreversible), MMTS creates a dithiomethane (reversible), EMCA creates a thioether (irreversible)). For example, iodoacteamide alkylates a sulfhydryl group with a cabamidolmethyl group (57.07 Da). Other means of blocking or capping cysteine sulfhydryl groups are known in the art. In some embodiments, the blocked sulfhydryl group is an alkylated sulfhydryl group. In some embodiments, the alkylated sulfhydryl group includes a cabamidolmethyl group.

The protein of the present invention may have from 1-20, or any range therein, cysteine residues including blocked sulfhydryl groups. In some embodiments, the protein includes 2-18 cysteine residues including a blocked sulfhydryl group.

The protein of the present invention may include a kinase domain of a tyrosine kinase. Tyrosine kinases are enzymes that can transfer a phosphate group from adenosine triphosphate (ATP) to the side chain of a tyrosine amino acid residue in a protein. Tyrosine kinases may include receptor tyrosine kinases and non-receptor tyrosine kinases. Receptor tyrosine kinases are cell surface receptors containing a transmembrane domain and tyrosine kinase domains. Non-receptor tyrosine kinases do not include transmembrane domains but do include tyrosine kinase domains. Receptor tyrosine kinases in accordance with the present invention may include, without limitation, Anaplastic Lymphoma Kinase receptors (ALK), Epidermal growth factor receptors (EGFRs), Fibroblast growth factor receptors (FGFRs), or Vascular endothelial growth factor receptors (VEGFRs). Non-receptor tyrosine kinases in accordance with the present invention may include, without limitation, PDGF, Src, Abl, or Jaks proteins.

In some embodiments, the protein of the present invention is a kinase domain from an Anaplastic Lymphoma Kinase (ALK) protein. Anaplastic Lymphoma Kinase (ALK) protein, also known as ALK tyrosine kinase receptor or CD246 (cluster of differentiation 246) is a receptor tyrosine kinase that in humans is encoded by the ALK gene (SEQ ID NO: 4). The human ALK protein has been reported to play an important role in brain development by exerting its effects on specific neurons in the nervous system.

In accordance with the present invention, ALK proteins may be any of the ALK proteins found in any mammal including, without limitation, humans or domesticated animals such as dogs, cats, horses, cows, pigs, mice, or rats. The protein sequence of an exemplary full-length ALK protein is indicated in SEQ ID NO: 3 (full-length human ALK protein). Suitably, the ALK protein includes the kinase domain of the protein and/or has at least 60%, 70%, 75%, 80%, 85%, 90%, 95%, 98%, or 99% sequence identity to SEQ ID NO: 1 (human ALK protein kinase domain) or SEQ ID NO: 2 (tagged version human ALK protein fragment from ProQinase L1066-S1437).

The ALK kinase domain may include SEQ ID NO: 1 (human ALK protein fragment from ProQinase L1066-S1437) or a polypeptide having at least 60%, 70%, 75%, 80%, 85%, 90%, 95%, 98%, or 99% sequence identity to SEQ ID NO: 1.

In some embodiments, the ALK kinase domain may include a phosphorylated tyrosine residue at position 31 of SEQ ID NO: 1, at position 218 of SEQ ID NO: 1, or both.

The ALK kinase domain may include SEQ ID NO: 2 (tagged version human ALK protein fragment from ProQinase L1066-51437) or a polypeptide having at least 60%, 70%, 75%, 80%, 85%, 90%, 95%, 98%, or 99% sequence identity to SEQ ID NO: 2.

In some embodiments, the ALK kinase domain may include a phosphorylated tyrosine residue at position 69 of SEQ ID NO: 2, at position 256 of SEQ ID NO: 2, or both.

In some embodiments, the ALK kinase domain may include 2-11, or any range therein, cysteine residues comprising a blocked sulfhydryl group.

The proteins described herein may include "mutant" proteins, variants, and derivatives thereof. As used herein the term "wild-type" is a term of the art understood by skilled persons and means the typical form of an organism, strain, gene or characteristic as it occurs in nature as distinguished from mutant or variant forms. As used herein, a "variant, "mutant," or "derivative" refers to a polypeptide molecule having an amino acid sequence that differs from a reference protein or polypeptide molecule. A variant or mutant may have one or more insertions, deletions, or substitutions of an amino acid residue relative to a reference molecule. A variant or mutant may include a fragment of a reference molecule. For example, a protein mutant or variant protein may have one or more insertions, deletions, or substitution of at least one amino acid residue relative to the "wild-type" protein. The protein sequences of a "wild-type" ALK protein and its kinase domain from humans are presented in SEQ ID NOs: 1 and 3. These sequences may be used as reference sequences.

A protein may be a full-length protein or may be fragments of the full-length protein. As used herein, a "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference protein, respectively. In some embodiments, a fragment may comprise at least 5, 10, 15, 20, 25, 30, 40, 50, 60, 70, 80, 90, 100, 150, 250, or 500 contiguous amino acid residues of a reference protein. Fragments may be preferentially selected from certain regions of a molecule. The term "at least a fragment" encompasses the full length polypeptide. A fragment may include an N-terminal truncation, a C-terminal truncation, or both truncations relative to the full-length tyrosine kinase protein or ALK protein. Preferably, a fragment of a tyrosine kinase protein or ALK protein includes amino acid residues required for the protein's kinase activity and/or autophosphorylation activity.

A "deletion" in a protein refers to a change in the amino acid sequence resulting in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide).

"Insertions" and "additions" in a protein refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A variant of a protein may have N-terminal insertions, C-terminal insertions, internal insertions, or any combination of N-terminal insertions, C-terminal insertions, and internal insertions.

Regarding proteins, the phrases "percent identity," "% identity," and "% sequence identity" refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases. As described herein, variants, mutants, or fragments (e.g., a tyrosine kinase protein variant, mutant, or fragment thereof or ALK protein variant, mutant, or fragment thereof) may have 99%, 98%, 97%, 96%, 95%, 94%, 93%, 92%, 91%, 90%, 80%, 70%, 60%, or 50% amino acid sequence identity relative to a reference molecule (e.g., relative to the kinase domain of an ALK protein (SEQ ID NO: 1) or a full-length ALK protein (SEQ ID NO: 3)).

Protein sequence identity may be measured over the length of an entire defined protein sequence, for example, as defined by a particular SEQ ID number, or may be measured over a shorter length, for example, over the length of a fragment taken from a larger, defined protein sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

The amino acid sequences of the protein variants, mutants, or derivatives as contemplated herein may include conservative amino acid substitutions relative to a reference amino acid sequence. For example, a variant, mutant, or derivative polypeptide may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

Methods of making a protein standard are provided. The methods may include (i) phosphorylating a starting protein including an amino acid residue capable of being phosphorylated and a cysteine residue to produce a phosphorylated protein, and (ii) contacting the phosphorylated protein with a sulfhydryl blocking agent.

As used herein, "phosphorylating a starting protein" refers to the process of transferring a phosphate group from adenosine triphosphate (ATP) to the side chain of a serine, threonine, histidine, or tyrosine amino acid residue in the starting protein. Phosphorylating the starting protein may be carried out by incubating the starting protein with a kinase protein. Alternatively, in the case of kinases that may autophosphorylate such as tyrosine kinases, the starting protein may be simply incubated in an appropriate buffer with ATP. In the Examples, the inventors phosphorylated the ALK starting protein by incubating the protein with ATP in an optimized reaction mixture specified by ProQinase.

In accordance with the present invention, a "starting protein" may include an amino acid residue capable of being phosphorylated and a cysteine residue. Amino acids capable of being phosphorylated include serine, threonine, histidine, and tyrosine. In some embodiments, the starting protein may include from 1-20 amino acid residues capable of being phosphorylated or any range therein. In some embodiments, the protein comprises 2-18 amino acid residues capable of being phosphorylated. In some embodiments, the protein comprises 2-18 tyrosine residues capable of being phosphorylated.

The "starting protein" may have from 1-20, or any range therein, cysteine residues. In some embodiments, the starting protein includes 2-18 cysteine residues.

The "starting protein" of the present invention may be within a particular molecular weight range. The starting protein may be between 5 and 250 kilodaltons or within any range therein. In some embodiments, the starting protein has a molecular weight between 40 and 60 kilodaltons.

The "starting protein" of the present invention may include a kinase domain of a tyrosine kinase. In some embodiments, the starting protein of the present invention is a kinase domain from an Anaplastic Lymphoma Kinase (ALK) protein. As used herein, the ALK kinase domain may include SEQ ID NO: 1 (human ALK protein fragment from ProQinase L1066-S1437), a polypeptide having at least 60%, 70%, 75%, 80%, 85%, 90%, 95%, 98%, or 99% sequence identity to SEQ ID NO: 1, SEQ ID NO: 2, or a polypeptide having at least 60%, 70%, 75%, 80%, 85%, 90%, 95%, 98%, or 99% sequence identity to SEQ ID NO: 2.

As used herein, a "sulfhydryl blocking agent" refers to an agent capable of modifying a sulfhydryl group of a cysteine residue so as to prevent the ability of the sulfhydryl group to form disulfide bonds with another sulfhydryl group. Several sulfhydryl blocking agents may be used to block cysteine sulfhydryl groups including, without limitation, N-Ethylmalemide (NEM), Methyl methanethiosulfonate (MMTS), EMCA, or iodoacetamide. In some embodiments, the sulfhydryl blocking agent includes an alkylating agent such as, without limitation, iodoacetamide.

Methods for quantitating the abundance of a phosphorylated protein in a sample are also provided. The methods may include (a) obtaining the sample, and (b) adding a predetermined amount of any one of the protein standards disclosed herein to the sample to produce a spiked sample. Optionally, the methods may further include any one of, or any combination of the following steps: (c) separating the proteins in the spiked sample to produce a separated sample, (d) detecting the phosphorylated protein in the separated sample to produce a phosphoprotein signal, (e) detecting the protein standard in the separated sample to produce a protein standard signal, (f) determining the abundance of the phosphorylated protein in the sample based on the phosphoprotein signal and the protein standard signal. In some embodiments, the methods may further include extracting the sample prior to the separation step (c).

As used herein, a "sample" may be any type of sample containing 1 or more proteins. The sample may be a clinical sample including, without limitation, a tumor, gut, fecal, blood, urine, synovial fluid, or saliva sample from a subject.

As used herein, the term "subject" are used interchangeably and refer to both human and non-human animals. The term "non-human animals" of the disclosure includes all vertebrates, e.g., mammals and non-mammals, such as non-human primates, sheep, dog, cat, horse, cow, chickens, amphibians, reptiles, and the like. Preferably, the subject is a human patient. Suitably, the subject is a human patient diagnosed with cancer or undergoing, or about to undergo, a cancer treatment regimen.

The sample may be a tumor sample from a lung, colorectal, pancreatic, breast, liver, esophageal, gastric, kidney, small bowel, cholangiocarcinoma, lung, head and neck, thyroid, melanoma, breast, renal, bladder, ovarian, cervical, uterine, prostate, lymphomas, leukemias, neuroendocrine, glioblastoma or any other form of brain cancer.

In accordance with the present methods, the "predetermined amount" of the protein standard may be between 0.05-10 ng per sample. Suitably, the predetermined amount of the protein standard may be between 0.1-2 ng per sample.

The phosphorylated protein of the present methods may include a protein that is, or is suspected of being, over or under phosphorylated in a cancer cell. Exemplary phosphorylated proteins include proteins of the HER signaling pathway including, without limitation, HER1 (EGFR), HER2, HER3, or HER4 proteins. In some embodiments, a phosphorylated protein may include a receptor tyrosine kinase including, without limitation, PDGFR, MET, FGFR, ALK, or VEGFR.

In some embodiments, the present methods may further comprise administering a "receptor tyrosine kinase targeting agent" to the subject following any or all of steps (a)-(f) of the present methods. Suitable receptor tyrosine kinase targeting agents may include, without limitation, necitumumab, crenolanib, crizotinib, or dovitinib.

In some embodiments, the present methods may further comprising administering a HER targeting agent to the subject following any or all of steps (a)-(f) of the present methods. A "HER targeting agent" is a therapeutic agent that may modify the activity of a HER protein. Suitable HER targeting agents include, without limitation, cetuximab (Erbitux™), gefitinib (Iressa™), erlotinib (Tarceva™), afatinib (Gilotrif™), brigatinib, icotinib, trastuzumab (Herceptin®), and lapatinib (Tyverb/Tykerb®). Cetuximab is a monoclonal antibody against HER1(EGFR) that is FDA approved for the treatment of head and neck cancer and colorectal cancer in patients. Gefitinib, Erlotinib, Afatinib, Brigatinib, and Icotinib are all small molecule inhibitors of HER1 (EGFR) each used to treat certain types of cancer. Trastuzumab and lapatinib are dual HER1 (EGFR)/HER2 inhibitors. Multiple other HER targeting agents are in various stages of clinical development and may be used in accordance with the present methods. Administration of the HER targeting agent would be in view of a physician's judgment and/or FDA-approved label requirements.

The present methods may include "extracting" the sample prior separation and/or detection. Suitable extraction methods for proteins are known in the art and may include, without limitation, repeated freezing and thawing, sonication, homogenization, filtration, or permeabilization.

The present methods may include "separating" the proteins in the spiked sample to produce a separated sample. Protein separation techniques are well-known in the art and may include, without limitation, centrifugation, ultracentrifugation, chromatography techniques, electrophoresis techniques, or combinations thereof. Chromatography techniques may include, without limitation, gas chromatography, size exclusion chromatography, gel permeation chromatography, hydrophobic interaction chromatography, ion exchange chromatography, high performance liquid chromatography (HPLC), reverse phase chromatography, and affinity chromatography. Electrophoresis techniques may be under denaturing (i.e., SDS) or non-denaturing conditions, may be one dimensional (1D) or two dimensional (2D), and may include, without limitation, polyacrylamide gel electrophoresis, agarose gel electrophoresis, starch gel electrophoresis, free-flow-electrophoresis, and capillary electrophoresis.

The present methods may include "detecting" the phosphorylated protein and/or protein standard. Protein detection methodologies are well-known in the art and may include, without limitation, western blotting, immunoprecipitation, enzyme-linked immunosorbent assay (ELISA), radioimmunoassay (RIA), mass spectrometry techniques, Surface Enhanced Laser Desorption Ionization Spectroscopy (SELDI), or a combination thereof. Mass spectrometry techniques may include, without limitations, Matrix Assisted Laser Desorption Ionization/Time of Flight (MALDI/TOF) and electrospray techniques.

The present methods may further include determining the abundance of the phosphorylated protein in the sample based on the phosphoprotein signal and the protein standard signal in a sample. Such methods may include comparing the intensity of the phosphoprotein signal to the intensity of the protein standard signal in the sample. One method of comparing the phosphoprotein signal and protein standard would be to divide the intensity of the phosphoprotein signal by the protein standard signal to produce a ratio that may be used for comparison across 2 or more samples.

Kits are provided. The kits may include any one of the protein standards disclosed herein. Optionally, the kits may further include a phospho-specific antibody. As used herein, a "phospho-specific antibody" refers to an antibody that specifically recognizes phosphorylated serine, threonine, histidine, or tyrosine amino acid residues in proteins. In some embodiments, the phospho-specific antibody is a phosphotyrosine-specific antibody that specifically recognizes phosphorylated tyrosine amino acid residues in proteins. In the Examples, the inventors use an anti-phosphotyrosine mouse monoclonal antibody PY20 (Exalpha, Cat #X1021). Other phosphotyrosine-specific antibodies are well-known in the art and thus may be used in accordance with the present invention.

The kits may include (i) a starting protein comprising an amino acid residue capable of being phosphorylated and a cysteine residue and (ii) a sulfhydryl blocking agent.

The kits may include adenosine triphosphate (ATP).

The kits may include instructions for performing any one of the methods of disclosed herein.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus ≥10% of the particular term.

The following examples are meant only to be illustrative and are not meant as limitations on the scope of the invention or of the appended claims.

EXAMPLES

Example 1—pALK48-SB: A New Phosphotyrosine-Protein Internal Standard for Enhanced Chemiluminescence Western Blotting of Biological Samples Receptor tyrosine kinases (RTK) such as epidermal growth factor receptor (EGFR) are high molecular weight, glycosylated, transmembrane proteins. They become activated when serum ligands such as EGF bind to a protein domain located on the outside of the cell. Ligand binding causes RTK dimerization, which in turn brings about trans-phosphorylation of multiple tyrosine residues on the RTK cytosolic chain via a kinase domain. Each phosphotyrosine (pTyr) residue serve as a specific docking site for a cytosolic protein containing a corresponding SH2 domain. Subsequent interactions between the docked proteins give rise to a host of important downstream interactions including cell division.

In 2011 our laboratory started experimenting with 1D and 2D SDS PAGE western blotting (WB) using enhanced chemiluminescence detection (ECL) in combination with a monoclonal pTyr antibody, PY20. We observed that this antibody has enough sensitivity to directly detect pTyr-EGFR, the activated form, in some human lung cancer samples. Specifically, a pTyr-band and corresponding 2D spot were detected at ~175 kDa in 2/14 of lung cancer samples from a commercial tissue bank. Anti-EGFR western blotting of the tumor and control samples showed that unphosphorylated EGFR (i.e. inactive) was present in all of the samples in varying amounts. Only two samples, however, showed a form that co-migrated with a strong pTyr signal. Furthermore, 2D western blotting was able to distinguish pTyr-EGFR from another RTK, pTyr-PDGFR (platelet derived growth factor receptor) in one of the two samples, and pTyr-keratins. These results suggest that 1D and 2D SDS PAGE pTyr WB might be a useful tool, an orthogonal method, to help unravel the role of various RTK in disease processes—if certain problems could be worked out.

One major problem with western blotting is that results are presented as pictures. Pictorial results from even a small group of 14 disease/control pairs were cumbersome to tabulate and present. A second problem is that ECL light emission, that imparts very high sensitivity, varies dramatically over the first 2 hours of film or scanner exposure. Thus, western blot density for the same sample often varies between SDS PAGE gels.

An appropriate pTyr-protein standard would theoretically solve both problems. An internal pTyr-protein standard would allow presentation of results as a number (ratio of RTK band density/pTyrStd band density) instead of a picture. The internal standard could be used to normalize results between different conditions of western blotting, and thus between labs. Finally, an internal standard could be used for validation of the method to meet GLP/GMP documentation requirements.

To that end we have developed an internal pTyr-protein standard which we call pALK48-SB or pA of molecular weight 48 kDa that contains at least two phosphotyrosines as evidenced by mass spectrometric analysis.

In this application we present data from pALK48-SB experiments with 2 different lots of a commercially available pTyr-EGFR samples (A431 cell lysates stimulated with EGF). We define the linear range of pALK48-SB detection with 1D SDS PAGE pTyr western blotting using standardized conditions. We demonstrate that pALK48-SB can be used to normalize results between different 2D SDS PAGE western blot film exposures and to determine the relative amount of pEGFR in different samples. pALK48-SB is a unique, useful, internal standard for phosphotyrosine western blotting.

Materials and Methods

Tyrosine phosphorylation of ALK48. Under the proper conditions, the kinase domain of one protein receptor tyrosine kinase reacts with and phosphorylates tyrosine side chains on another. The first step of our novel procedure is to perform a kinase reaction on the purchased starting material recombinant human active protein kinase ALK, product No 1048-0000-1 from ProQinase. Two different lots of pALK48-SB standard were prepared on different dates as follows: The starting material, recombinant human active protein kinase ALK (HIS-tag, product No 1048-0000-1) internal fragment amino acids L1066-S1437 (as in Gen Bank entry NM_004304.3) was purchased from ProQinase, GmbH. (Freiburg, Germany) The molecular weight of the ALK fragment is 47,991 daltons. This starting material is called ALK48.

Lot 1: A 20 µl aliquot of ALK48 containing 13.5 µg of protein was auto-phosphorylated by reaction with 2 mM ATP at 30° C. for one hour in an optimized reaction mixture specified by ProQinase. (GP, p43) Evidence of tyrosine phosphorylation is presented in the Results below.

The tyrosine-phosphorylated form of ALK48 is called pALK48.

Lot 2: A 20 ul aliquot of ALK48 containing 13.5 µg of protein was auto-phosphorylated by reaction with 2 mM ATP at 30° C. for one hour in an optimized reaction mixture specified by ProQinase. (GP, p51).

Alkylation of sulfhydryl groups with an iodoacetamide reaction. pAlk48 Lot 1 and Lot 2 sulfhydryl blockage: Cysteine sulfhydral groups were chemically blocked by alkylation with iodoacetamide according to directions from Thermo Scientific. (NK, GP's book p46-47 and GP p51-52). The sample was pretreated with TCEP-HCP for 1 hour at 55° C., and then reacted with iodoacetamide for 30 min at 55° C. protected from light. The reaction was stopped by addition of SDS Buffer containing 5% beta-mercaptoethanol. The iodoacetylated treated final standard is designated with an SB suffix (sulfhydryl blocked) i.e. pALK48-SB.

A431 whole cell lysate containing pTyr-EGFR protein standard Two Lots, lot 10852 and lot 13639, were purchased from Exalpha Biologicals, Shirley, Mass. (Cat #X1003, A431 cell lysates stimulated by EGF). These samples, already in SDS buffer were heated in a boiling water bath for 5 minutes before loading.

Sodium Dodecyl Polyacrylamide Gel Electrophoresis (SDS PAGE)

1D SDS PAGE: Standard format slab gels were poured in triplicate as follows. SDS slab gel electrophoresis was carried out according to standard methods and for the second dimension, using a 10% acrylamide slab gel (125 mm length×150 mm width×0.75 mm thickness) overlaid with a 25 mm stacking gel. Electrophoresis was performed using 15 mAmp/gel for about 3.5 hrs, at which time the bromophenol blue front had migrated to the end of the slab gel.

2D SDS PAGE: Two-dimensional electrophoresis was performed according to the carrier ampholyte method of isoelectric focusing by Kendrick Labs, Inc. (Madison, Wis.) according to standard operation procedures as follows: Isoelectric focusing was carried out in glass tubes of inner diameter 3.3 mm using 2% pH 3-10 Isodalt Servalytes (Serva, Heidelberg, Germany) for 9,600 volt-hrs. One µg of an IEF internal standard, tropomyosin, was added to each sample. This protein migrates as a doublet with lower polypeptide spot of MW 33,000 and pI 5.2. The enclosed tube gel pH gradient plot for this set of Servalytes was determined with a surface pH electrode.

After equilibration for 10 min in buffer "O" (10% glycerol, 50 mM dithiothreitol, 2.3% SDS and 0.0625 M tris, pH 6.8), each tube gel was sealed to the top of a stacking gel that overlaid a 10% acrylamide slab gel (0.75 mm thick). SDS slab gel electrophoresis was carried out for about 3.5 hrs at 15 mA/gel. The following proteins (Sigma Chemical Co., St. Louis, Mo. and EMD Millipore, Billerica, Mass.) were used as molecular weight standards: myosin (220,000), phosphorylase A (94,000), catalase (60,000), actin (43,000), carbonic anhydrase (29,000), and lysozyme (14,000). Note that this classic 2DE method, which uses carrier ampholines polymerized in acryamide tube gels for IEF, was first developed by O'Farrell in 1975. In 1977, Leigh and Norman Anderson first described compatibility with SDS which was subsequently confirmed by our lab in 1989. The Andersons showed that as IEF proceeds, SDS is stripped off proteins to make micelles with NP-40, a non-ionic detergent present in the tube gel. The charged micelles migrate to the acid end of the tube gel where they form a bulb that is cut off and discarded.

Transblotting: After slab gel electrophoresis, the gel for blotting was placed in transfer buffer (10 mM CAPS, pH 11.0, 10% methanol) and transblotted onto polyvinylidene difluoride (PVDF, ThermoFisher Scientific, Waltham, Mass.) membranes overnight at 200 mA and approximately 100 volts/two gels. The following proteins (Sigma Chemical Co., St. Louis, Mo. and EMD Millipore, Billerica, Mass.) were used as molecular weight standards: myosin (220,000), phosphorylase A (94,000), catalase (60,000), actin (43,000), carbonic anhydrase (29,000), and lysozyme (14,000). These standards appear as bands at the basic edge of the Coomassie blue-stained PVDF membrane. The following proteins (Sigma Chemical Co., St. Louis, Mo. and EMD Millipore, Billerica, Mass.) were added as molecular weight standards to a well: myosin (220,000), phosphorylase A (94,000), catalase (60,000), actin (43,000), carbonic anhydrase (29,000), and lysozyme (14,000). These standards appear as bands at the basic edge of the Coomassie blue-stained PVDF membrane.

Western Blotting: Each PVDF blot was stained with Coomassie Brilliant Blue R-250 and desktop scanned to record the total protein pattern. The blot was then blocked for two hours in 5% bovine serum albumin (BSA) in Tween-20 tris buffer saline (TTBS) and rinsed in TTBS. The blot was incubated overnight with shaking in primary antibody (Anti-phosphotyrosine mouse monoclonal antibody PY20 (Exalpha, Cat #X1021) diluted 1:1,000 in 2% BSA TTBS, rinsed 3×10 minutes in TTBS. The blot was then incubated in secondary antibody (Anti-mouse Ig G-HRP whole Ab, GE Healthcare Cat #NA9346) for 2 hours, rinsed 3×10 minutes in TTBS and treated with ECL Western Blotting Substrate (Pierce Thermo Fisher) and exposed to Kodak Biomax MR (High resolution radioisotope and chemiluminescent) x-ray film for 3 and then 10 minutes. The films were developed using a Konica Monolta SRX-101A film automatic film developer.

Western Blot Quantitative Analysis: The 1D and 2D ECL western blot films were digitized with a laser densitometer (Model PDSI, Molecular Dynamics Inc, Sunnyvale, Calif.). The densitometer was checked for linearity prior to scanning with a NIST calibrated Neutral Density Filter Set (Melles Griot, Irvine, Calif.). For western blot 1D gel images, band volumes were calculated using TotalLab Phoretix software (version 11.2) with a Microsoft (Windows 10) computer. Western blot 2D images were analyzed using Progenesis Same Spots software (version 4.5, 2011, TotalLab, UK) and Progenesis PG240 software (version 2006, TotalLab, UK) with a with a Microsoft (Windows 10) computer. Progenesis data for ratios (pE/pA) are shown in tables as a percent ((pE/pA)*100).

Results

Evidence of Tyrosine Phosphorylation of ALK48

A recombinant RTK fragment containing the tyrosine kinase domain should theoretically cross-phosphorylate itself under the proper conditions. FIG. 1 confirms the kinase domain of the recombinant starting material ALK48 is active. PVDF transblotted membranes are routinely stained prior to western blotting at Kendrick Labs to check total protein patterns and make sure each gel ran well. The blot is then destained and reacted with primary antibody overnight then incubated with secondary antibody followed by ECL detection. The final ECL x-ray film is superimposable with the Coomassie pattern, so spots lighting up on the film may be matched to the latter with confidence.

The position of internal pI markers on the stained blots in panels A and C of FIG. 1 indicate that both 2D gels, 2932 #1 and #2 ran identically and well. The ALK48 protein (black arrows) is streaky but visible in both cases. FIG. 1B shows that the anti-pTyr antibody does not bind to the unreacted ALK48 fragment, even for the heavy load of 1 μg protein. After the kinase reaction, a strong pTyr western blot signal is observed FIG. 1D at 48 kDa in a position that corresponds to the stained protein in 1C.

Alkylation of pAlk48 Prevents Aggregation

Interestingly, tyrosine phosphorylated ALK48 migrates differently in the isoelectric dimension of a 2D gel when mixed with 200 μg of human tumor sample (FIG. 2B) than when it is loaded by itself as shown in FIG. 2B. It also tends to streak in an irreproducible way when loaded alone, as shown in FIG. 2D. We hypothesize that during IEF, when the SDS is pulled off the protein by nonionic detergent NP-40 micelles in the tube gel, the ALK48 fragment tends to aggregate. It may be dimerizing with RTKs present in the tumor sample, or with itself.

Disulfide bonding between cysteine groups is well known to be a source of protein dimerization. ALK48 contains multiple cysteines that could form disulfide bonds in vivo to align the kinase domains properly. If this hypothesis is correct, blocking the ALK48 cysteines by alkylation with iodoacetamide would be expected to stop streaking due to disulfide bonding. In fact this is what is observed as shown in FIGS. 3C and 3D.

Figures 3A, 3B, 3C, 3D:
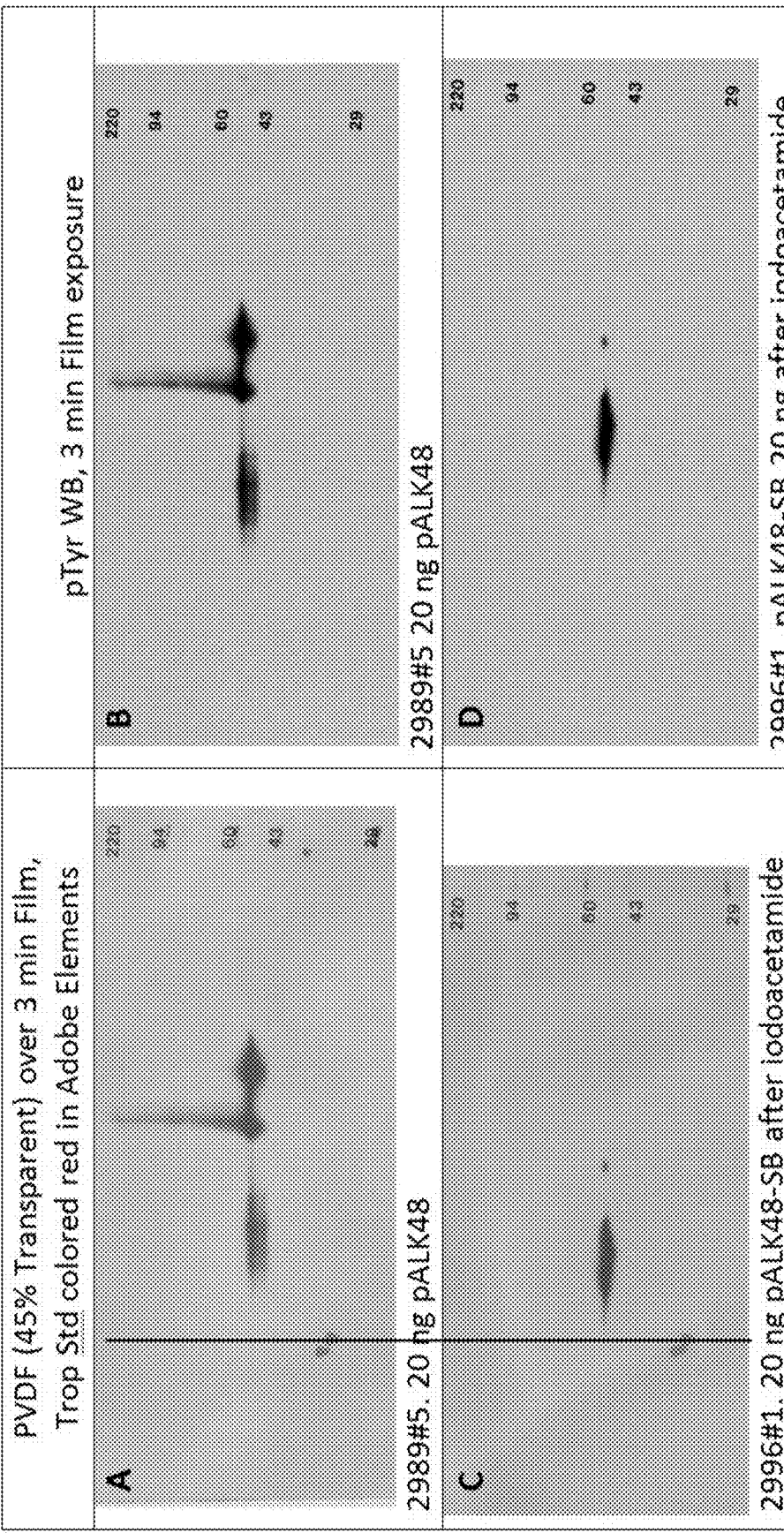

FIGS. 3A and B in the top row show the pALK48 streaky and diffuse pattern; 3C and D show the relatively tight, reproducible pattern after the iodoacetamide reaction. The blue overlay images on the left are aligned by the position of the tropomyosin internal standard (red spot). The pALK48-sulfhydryl-blocked (pALK48-SB) spot migrates primarily as single spot with slight streaking. It no longer aggregates during IEF and consistently migrates to the same 2D gel position in multiple experiments in the presence of A431 cell lysates containing pTyr-EGFR.

Quantitative Results of pA in 1D SDS PAGE

Figure 4:
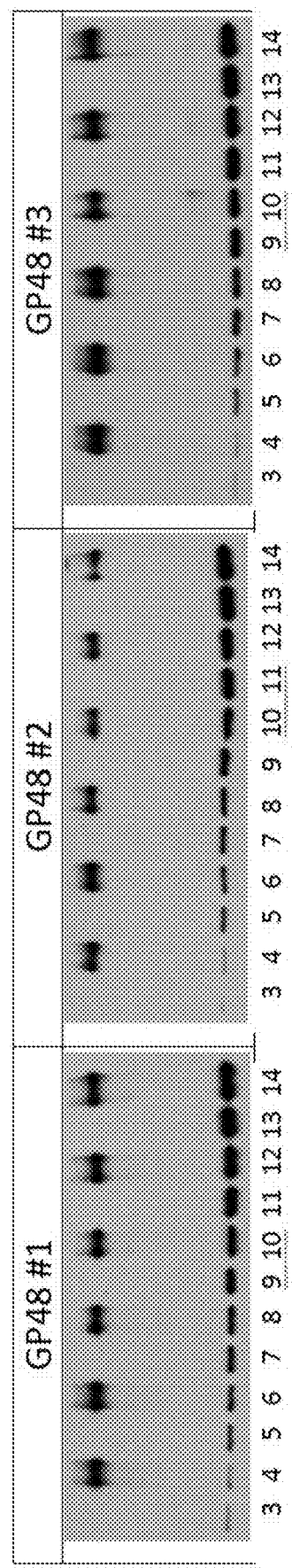

FIG. 4 and Table 1 shows images and loading scheme for triplicate 1D SDS PAGE pTyr WB films loaded with varying amounts of pA (0.1, 0.3, 0.5, 1.0, 2.0, and 4.0 ng) plus pEGFR positive control sample (commercial A431 EGF treated cell lysates that have a high level of pEGFR) in even rows. The films were scanned with a calibrated laser densitometer and the images analyzed with TotalLab 1D software. Standard curves were constructed for 3 min and 10 min films from each western blot. The ratio of each EGFR band to that of the average 1 ng pA band density was determined.

TABLE 1

Loading Scheme for Gels Shown in FIG. 4

| Lane | Sample |
|---|---|
| 3 | 0.1 ng pALK48-SB |
| 4 | 0.1 ng pALK48-SB + 5 μl EGFR test sample |
| 5 | 0.3 ng pALK48-SB |
| 6 | 0.3 ng pALK48-SB + 5 μl EGFR test sample |
| 7 | 0.5 ng pALK48-SB |
| 8 | 0.5 ng pALK48-SB + 5 μl EGFR test sample |
| 9 | 1.0 ng pALK48-SB |
| 10 | 1.0 ng pALK48-SB + 5 μl EGFR test sample |
| 11 | 2.0 ng pALK48-SB |
| 12 | 2.0 ng pALK48-SB + 5 μl EGFR test sample |
| 13 | 4.0 ng pALK48-SB |
| 14 | 4.0 ng pALK48-SB + 5 μl EGFR test sample |

Figure 5:
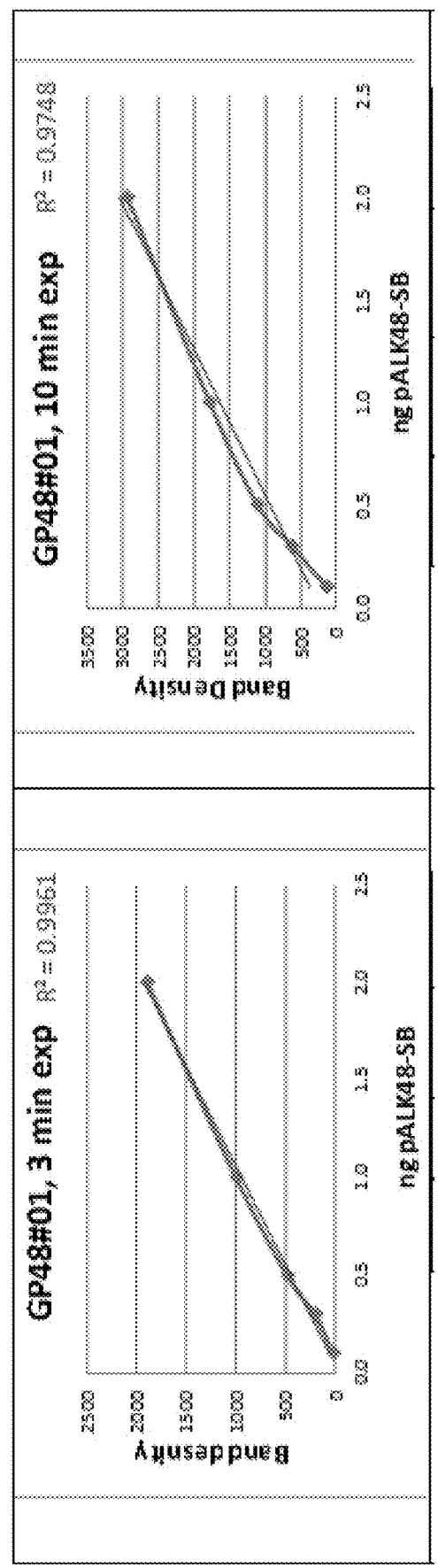
Figure 5:
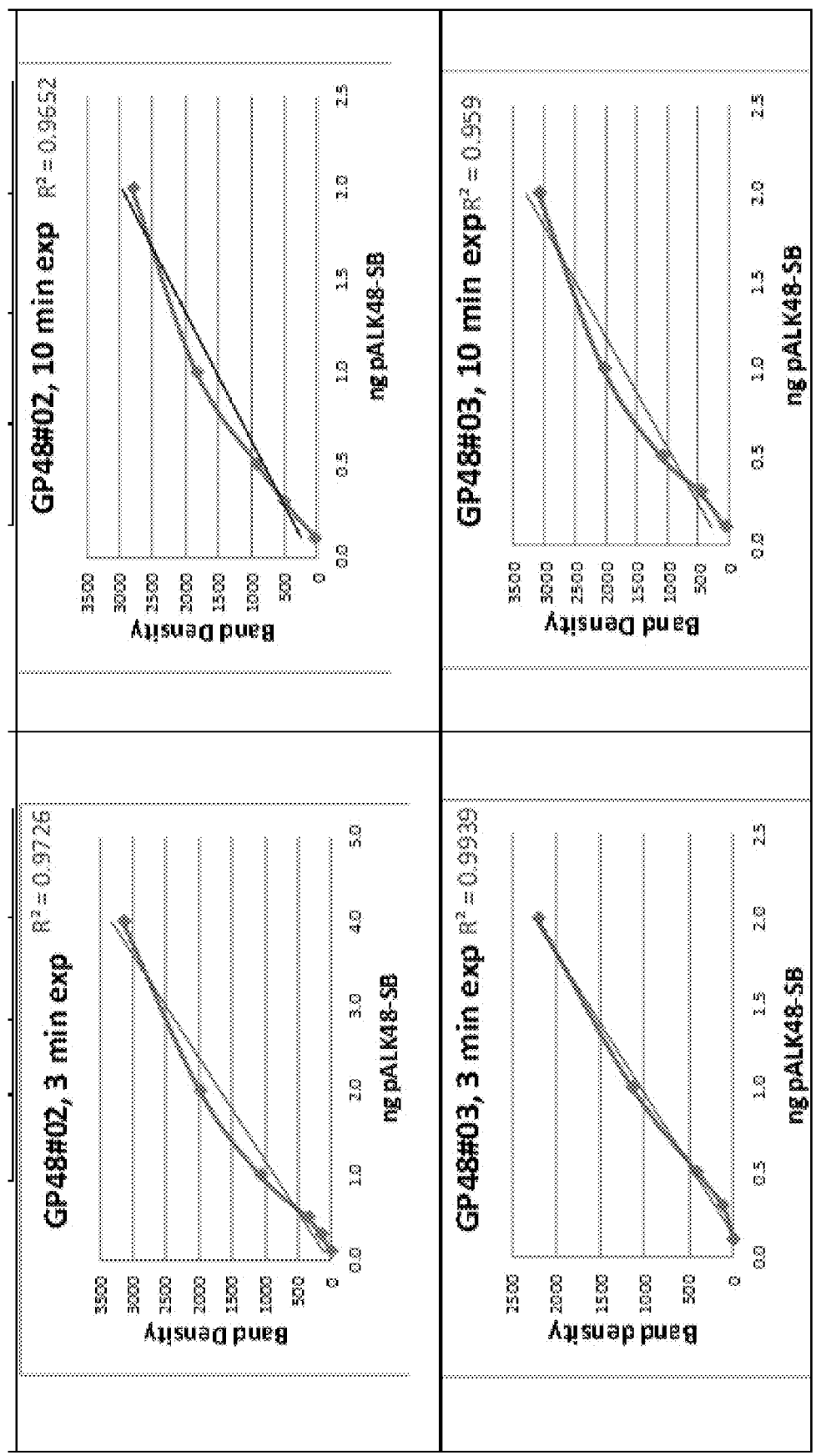

FIG. 5 shows plots of pALK48-SB band density versus ng loaded for GP48 #1, #2, and #3 (lot 1). The curves start to level off at the 4 ng point but are reasonably straight over the 0.1-2 ng range. Using pA as an internal standard within the linear range for standard western blot conditions would be appropriate, i.e. 1-2 ng.

The standard curves determined from a varied pALK48-SB load on each of the gels were linear over the range of 0.1 to 2.0 ng with Rf values of 0.95 or greater. The ratio of pEGFR/pAlk48-SB (1 ng) were calculated in Table 2. These ratios were used to estimate variability. The pEGFR/pA ratios agreed between different film exposures of each gel (Table 3), but varied from 1.0 to 2.0 between gels as shown in Table 4, because of variation in EGFR western blotting.

TABLE 2

Data and ratios of the pEGFR band density divided by the average (yellow) 1 ng pALK-SB density for even numbered lanes loaded with pEGFR test sample, lot 10852. There is good agreement between the 3 min and 10 min ratios for each of the 3 gels proving that density ratio normalization corrects for film exposure variation, as expected.

| GP48# 01 Lane | 5 ul EGFR 3 min Bd Density | 1000 EGFR/1 ng pALK48-SB | GP48# 01 Lane | 5 ul EGFR 10 min Bd Density | 1787 EGFR/1 ng pALK48-SB |
|---|---|---|---|---|---|
| 4 | 1820 | 1.8 | 4 | 3429 | 1.9 |
| 6 | 1901 | 1.9 | 6 | 3508 | 2 |
| 8 | 1350 | 1.4 | 8 | 2516 | 1.4 |
| 10 | 1259 | 1.3 | 10 | 2546 | 1.4 |
| 12 | 1667 | 1.7 | 12 | 3150 | 1.8 |
| 14 | 1730 | 1.7 | 14 | 3304 | 1.8 |
| | Average | 1.62 | | Average | 1.72 |
| | SD | 0.26 | | SD | 0.25 |
| | CV | 16 | | CV | 14 |
| GP48# 01 Lane | 5 ul EGFR 3 min Bd Density | 1069 EGFR/1 ng pALK48-SB | GP48# 02 Lane | 5 ul EGFR 10 min Bd Density | 1831 EGFR/1 ng pALK48-SB |
| 4 | 1030 | 1 | 4 | 2442 | 1.3 |
| 6 | 1573 | 1.5 | 6 | 3033 | 1.7 |
| 8 | 948 | 0.9 | 8 | 2099 | 1.1 |
| 10 | 467 | 0.4 | 10 | 1595 | 0.9 |
| 12 | 741 | 0.7 | 12 | 1366 | 1 |
| 14 | 703 | 0.7 | 14 | 1845 | 1 |
| | Average | 0.85 | | Average | 1.17 |
| | SD | 0.36 | | SD | 0.28 |
| | CV | 42 | | CV | 24 |
| GP48# 03 Lane | 5 ul EGFR 3 min Bd Density | 1144 EGFR/1 ng pALK48-SB | GP48# 03 Lane | 5 ul EGFR 10 min Bd Density | 2044 EGFR/1 ng pALK48-SB |
| 4 | 2633 | 2.3 | 4 | 4328 | 2.1 |
| 6 | 2688 | 2.3 | 6 | 4411 | 2.2 |
| 8 | 2687 | 2.3 | 8 | 4547 | 2.2 |
| 10 | 1371 | 1.2 | 10 | 3114 | 1.5 |
| 12 | 2190 | 1.9 | 12 | 3925 | 1.9 |
| 14 | 2343 | 2 | 14 | 3996 | 2 |
| | Average | 2.03 | | Average | 1.98 |
| | SD | 0.44 | | SD | 0.25 |
| | CV | 22 | | CV | 13 |

TABLE 3

Summary of pEGFR/pA (1 ng) Band Density Ratio Values for the 3 min (left) and 10 min (right) film exposures for all 3 gels. The average ratios obtained from three 1D gels loaded as described in FIG. 5 (two different film exposures each) were 1.4 +/- 0.61 for the 3 min and 1.6 +/- 0.43 for the 10 min EGFR/pA 1D band density ratios for Lot 1 (GP48)

| | GP48-3 min EGFR/1 ng pA Ratio (Laser) | | | | GP48-10 min: EGFR/1 ng pA Ratio (Laser) | | |
|---|---|---|---|---|---|---|---|
| Lane | 3 min #1 EGFR/pA | 3 min #2 EGFR/pA | 3 min #3 EGFR/pA | Lane | #1 EGFR/pA | #2 EGFR/pA | #3 EGFR/pA |
| 4 | 1.8 | 1.0 | 2.3 | 4 | 1.9 | 1.3 | 2.1 |
| 6 | 1.9 | 1.5 | 2..3 | 6 | 2.0 | 1.7 | 2.2 |
| 8 | 1.4 | 0.9 | 2.3 | 8 | 1.4 | 1.1 | 2.2 |
| 10 | 1.3 | 0.4 | 1.2 | 10 | 1.4 | 0.9 | 1.5 |
| 12 | 1.7 | 0.7 | 1.9 | 12 | 1.8 | 1.0 | 1.9 |
| 14 | 1.7 | 0.7 | 2.0 | 14 | 1.8 | 1.0 | 2.0 |
| | | AVERAGE | 1.4 | | | AVERAGE | 1.6 |
| n = 18 | | SD | 0.61 | n = 18 | | SD | 0.43 |

TABLE 4

Variation between GP48 gels shown in FIG. 5
pEGFR/pA average ratios

| Gel | 3 min | 10 min | Average |
|---|---|---|---|
| GP48#01 | 1.62 | 1.72 | 1.7 |
| GP48#02 | 0.85 | 1.17 | 1.0 |
| GP48#03 | 2.03 | 1.98 | 2.0 |

Quantitative Results for 2D SDS PAGE:

The concentration of pEGFR in the commercial EGF-treated A431 cell lysate, our pTyr positive test sample, is unknown. The lysate is sold in aliquots containing 1 mg/mL of total cellular protein as a positive control for the PY20 antibody. In fact, this commercial sample is a good model for real world biological samples where RTK concentrations are never known.

The goal is to test whether results from 2D pTyr western blots can be normalized by taking ratios of unknown pTyr spot densities to that of a known amount of pALK48-SB added as an internal standard. One way to do this is to vary the amount of pEGFR-A431 loaded while keeping the pALK48-SB constant. Doubling the amount of pEGFR-A431 (pE) relative to pALK48-SB (pA) for example, should theoretically cause the pE/pA ratio to double. Halving the pE load should reduce the pE/pA ratio by half. If the expected changes in density ratio agree with the measured ratios, the normalization is working.

To that end, the loaded ratio of pTyr-EGFR to pALK48-SB was varied, for 2 sets of 2D gels, according to Table 5. The goal was to determine if the resultant 2D spot density ratios would reflect these changes. The 1 and 2 ng loads of pALK48-SB are in the linear range shown for the 1D plots of band density versus ng loaded as previously shown in Table 2.

TABLE 5

Theoretical ratios and amounts loaded of pEGFR-A431
test sample and pALK48-SB control.

| Load 1 | Load 2 | Load 3 | Load 4 |
|---|---|---|---|
| Ratio = X | Ratio = 2X | Ratio = 0.5X | Ratio = X |
| 10 µl EGFR, | 20 µl EGFR, | 10 µl EGFR, | 20 µl EGFR, |
| 1 ng pALK-SB | 1 ng pALK-SB | 2 ng pALK-SB | 2 ng pALK-SB |

One set of eight gels would be loaded with Lot 10852 of pTyr-EGFR-A431 from Exalpha, while the other set would be loaded with Lot 13639. Visual comparisons of 2D pTyr western blots from the two lots show a noticeable difference: the pTyr spot was always lighter in Lot 13639 for the same volume of sample. Two different lots of pALK48-SB were used as well (Lot 1 and 2) but those 2D spots visually looked the same for the same amount loaded.

Two sets of 2D gels were loaded in duplicate for each condition (X, 2X, 0.5X and X with double pE and pA). Gels from p3016 #1-8 were loaded with pTyr-EGFR-A431 Lot 10852+pALK48-SB Lot 1. Gels from 3017 #1-8 were loaded with pTyr-EGFR-A431 Lot 13639+pALK48-SB lot 2. See FIGS. 6 and 7; Tables 6-9. The experiment performed with the gels of 2016 #1-8 was repeated with pTyr-EGFR-A431 Lot 13639 and pALK48-SB Lot 2. Again 2D SDS PAGE gels were loaded in duplicate (p3017 #1-8).

TABLE 6

Tabulated results for Spot Density Ratios for the four conditions of X, 2X, 0.5X and X (both loads doubled) for Lot 1 EGFR added to Lot 1 pALK48-SB. To find the best value for X, average ratios for each condition were added (X, 2X, 0.5X, and X) and the sum divided by 4.5. In this case the average value for the ratio X = 177.
Laser p30164#1-8, SameSpots outlines

| ID # | Film Exp. | EGFR/pA Ratio | Ave Ratio | Average n = 4 | SD (n = 4) | Load |
|---|---|---|---|---|---|---|
| 3016#1 | 3 min | 232 | 215 | 166 | 61 | Ratio = X |
| 3016#1 | 10 min | 198 | | | | 10 ul EGFR, |
| 3016#2 | 3 min | 139 | 118 | | | 1 ng pALK-SB |
| 3016#2 | 10 min | 96 | | | | |
| 3016#3 | 3 min | 267 | 253 | 366 | 140 | Ratio = 2X |
| 3016#3 | 10 min | 239 | | | | 20 ul EGFR, |
| 3016#4 | 3 min | 539 | 478 | | | 1 ng pALK-SB |
| 3016#4 | 10 min | 417 | | | | |
| 3016#5 | 3 min | 52 | 54 | 71 | 20 | Ratio = 0.5X |
| 3016#5 | 10 min | 55 | | | | 10 ul EGFR, |
| 3016#6 | 3 min | 91 | 89 | | | 2 ng pALK-SB |
| 3016#6 | 10 min | 86 | | | | |
| 3016#7 | 3 min | 239 | 220 | 194 | 34 | Ratio = X |
| 3016#7 | 10 min | 200 | | | | 20 ul EGFR, |
| 3016#8 | 3 min | 173 | 168 | | | 2 ng pALK-SB |
| 3016#8 | 10 min | 163 | | | | |
| | | Sum | 797 | | | |
| | Sum/4.5 = X | | 177 | | | |

TABLE 7

Measured density values divided by expected values
for the 4 conditions. Agreement is good.
Summary 3016#1-8
Ave X Ratio pEGFR/pA = 177

| Relative pEGFR/pA Density Ratio | p3016 Measured/X Expected |
|---|---|
| X = 1 | 0.94 |
| X = 2 | 2.1 |
| X = 0.5 | 0.40 |
| X = 1 | 1.1 |

TABLE 8

Tabulated results for Spot Density Ratios from p3017. To find the best value for X, average ratios for each condition were added (X, 2X, 0.5X, and X) and the sum divided by 4.5. In this case the average value for the ratio X = 48.
Laser p3017#1-8, SameSpots Outlines

| ID # | Film Exp. | EGFR/pA Ratio | Ave Ratio | Average n = 4 | SD (n = 4) | Load |
|---|---|---|---|---|---|---|
| 3017#1 | 3 min | 52 | 46.5 | 51 | 7 | Ratio = X |
| 3017#1 | 10 min | 41 | | | | 10 ul EGFR, |
| 3017#2 | 3 min | 56 | 56 | | | 1 ng |
| 3016#2 | 10 min | 56 | | | | pALK-SB |
| 3017#3 | 3 min | 64 | 70 | 88 | 22 | Ratio = 2X |
| 3017#3 | 10 min | 76 | | | | 20 ul EGFR , |
| 3017#4 | 3 min | 97 | 105.5 | | | 1 ng |
| 3017#4 | 10 min | 114 | | | | pALK-SB |
| 3017#5 | 3 min | 32 | 29 | 20 | 10 | Ratio = 0.5X |
| 3017#5 | 10 min | 25 | | | | 10 ul EGFR, |
| 3017#6 | 3 min | 10 | 12 | | | 2 ng |
| 3017#6 | 10 min | 14 | | | | pALK-SB |
| 3017#7 | 3 min | 50 | 60 | 56 | 11 | Ratio = X |
| 3017#7 | 10 min | 70 | | | | 20 ul EGFR, |
| 3017#8 | 3 min | 44 | 52 | | | 2 ng |
| 3017#8 | 10 min | 60 | | | | pALK-SB |
| | | Sum | 215 | 215 | | |
| | Sum/4.5 = X | | 48 | | | |

TABLE 9

Summary of measured vs expected ratios for Lot 13639 pEGFR & Lot 2 pALK48-SB for the 4 loading conditions. The absolute amount of pEGFR is much less in Lot 13639 than in Lot 1.
Summary 3017#1-8
Ave X Ratio pEGFR/pA = 48

| Relative pEGFR/pA Density Ratio | p3017 Measured/X Expected |
|---|---|
| X = 1 | 1.1 |
| X = 2 | 1.8 |
| X = 0.5 | 0.4 |
| X = 1 | 1.2 |

Discussion and Conclusions

Anaplastic lymphoma kinase (ALK) is a well-characterized receptor tyrosine kinase. See, e.g., Roskoski, R., Jr. (2013) Anaplastic lymphoma kinase (ALK): structure, oncogenic activation, and pharmacological inhibition, *Pharmacol Res* 68, 68-94. We have converted a commercially available recombinant 48 kDa ALK fragment containing the tyrosine kinase domain (ALK48) into a novel phosphotyrosine-protein standard by means of two chemical reactions. First, the fragment was phosphorylated on tyrosine residues by trans-reaction with its own kinase domain. Second, protein crosslinking between cysteine groups was blocked by treatment with the sulfhydryl-reactive alkylating agent iodoacetamide to give pALK48-SB (Sulfhydral Blocked).

In this application we provide evidence that the ALK48 is phosphorylated on tyrosine residues by the first reaction to give pALK48, and evidence that blocking disulfide crosslinking of pALK48 prevents streaking during the isoelectric focusing dimension of 2D SDS PAGE.

Results of 1D SDS PAGE demonstrate that the pAlk48-SB is linear in the range of 0.1-2 ng. However, variation in the ratio of pE/pA was observed in a few of the 1D lanes when comparing gels. This is visually apparent in the images shown in FIG. 5 and is largely due to variation in pEGFR signal. EGFR is a high molecular weight, glycosylated protein that appears as a diffuse spot pattern on a 2D gel because of micro-heterogeneity in the sugar chains of different molecules. It is not surprising that the western blot reaction would have more variability than is observed for the 48 kDa unglycosylated pTyr-standard. Even given EGFR variability, the method would clearly be useful to determine if a biological sample had low amounts of pEGFR (ratios of 1-2) versus high amounts, ratios of 25-50 for example. In cases where a biological sample contains a large amount of phosphorylated receptor tyrosine kinase (pRTK), the pRTK/pA ratio would not be strictly quantitative because the pRTK would fall in the saturated part of the curve. The true pRTK amount would always be greater than the ratio indicates, however. Results would still be meaningful.

Furthermore, we provide evidence that two specific questions can be answered positively. From here on pALK48-SB will be abbreviated pA and pTyr-EGFR-A431 test sample will be abbreviated pE.

Specific Questions

Q1. If 1 and 2 ng loads of pA are run in duplicate on 2D SDS PAGE gels with two known amounts (10 µl and 20 µl) of a pE test sample, will the measured ratio of the 2D spot density values of the proteins vary in agreement with the loaded ratios? For example, if the pE is doubled, will the pE/pA spot density ratio double?

The answer is Yes, with 10-12% difference variation between measurements. There is internal consistency between measurements for each set.

Each of the four conditions (X, 2X, 0.5X and X-double) was run in duplicate with 3 and 10 min film exposures. The 16 films were analyzed with SameSpots software to obtain a value for Spot Density (integrated spot density above background). The pE/pA spot density ratio was determined for each film and tabulated in Tables 6 (3016 #1-8) and 7 (3017 #1-8). Spot ratio agreement between the 2 film exposures was good.

An average pE/pA density value for X was determined from each of the four conditions (n=2 gels, 2 measurements each) as shown in Table 7 and the overall average of that was determined by summation and dividing by 4.5. (X+2X+0.5X+X). The overall average for the pE/pA X value (n=8 gels, 2 exposures each for 16 measurements) for 3016 #1-8 was 177, while the overall average pE/pA X value for 3017 #1-8 was 48. Assuming 177, the overall average pA/pE ratio, is the true ratio for Lot 1, than as shown in Table 10, the percent difference from expected is about 10%.

TABLE 10

Difference between measured values from duplicate gels and expected (overall average determined from 8 gels)
Variation from Overall Average Ratio of X (177)

| Loaded Ratio | p3016 pE/pA Measured Ave (n = 2 gels) | pE/pA Overall Average | Difference | % Diff = Diff/OA Ave*100 |
|---|---|---|---|---|
| X | 166 | 177 | 11 | 6 |
| 2X | 366 | 354 | −12 | 3 |
| 0.5X | 71 | 88 | 17 | 19 |
| X (dbl) | 194 | 177 | −17 | 10 |
| | | | Average % difference | 10 |

Similarly, for the p3017 gels, run identically except Lot 13639 of pE and lot 2 of pA were used, the percent difference from expected is 12% as shown in Table 11.

TABLE 11

Difference between measured values from duplicate gels and expected (overall average determined from 8 gels) for p3017.
Variation from Overall Average Ratio of X (48)

| Loaded Ratio | p3017 pE/pA Measured Ave (n = 2 gels) | pE/pA Overall Average | Difference | % Diff = Diff/ Exp*100 |
|---|---|---|---|---|
| X | 51 | 48 | −3 | 6 |
| 2X | 88 | 96 | 8 | 8 |
| 0.5X | 20 | 24 | 4 | 17 |
| X(dbl) | 56 | 48 | −8 | 17 |
| | | | Average % Diffeence | 12 |

Q2. If different samples of a pTyr-RTK contain different amounts of a pTyr-RTK, will the normalized values be predictive of relative amounts?

Evidence is provided that the answer is Yes. Table 12 shows results for each condition compared separately between the two lots of pE. The average of duplicate samples for each lot, loaded identically on 2D gels, gave comparison values of 3.3 to 4.2 with an average of 3.6+/−0.4 for the fold increase in Lot 10852 versus Lot 13639. Comparing the pE/pA Overall Average from Lot 10852 (3016, 177) to that of Lot 13639 (3017, 48) gives a fold difference of 3.7. Internal consistency between the measurements is good.

TABLE 12

Summary of pE/pA ratios from two independent experiments (3016 & 3017)

|  | Load 1<br>Ratio = X<br>10 µL EGFR,<br>1 ng pALK-SB | Load 2<br>Ratio = 2X<br>20 µL EGFR,<br>ng pALK-SB | Load 3<br>Ratio = 0.5X<br>10 µL EGFR,<br>2 ng pALK-SB | Load 4<br>Ratio = X<br>20 µL EGFR,<br>2 ng pALK-SB | Average | SD |
|---|---|---|---|---|---|---|
| 3016#1-8, pE Lot 1 | 166 | 366 | 71 | 194 | 3.6 | 0.4 |
| 3017#1-8, pE Lot 2 | 51 | 88 | 20 | 56 | | |
| Lot 1/Lot 2 | 3.3 | 4.2 | 3.6 | 3.5 | | |

1D and 2D SDS PAGE western blotting with a pTyr antibody is a sensitive way to detect active receptor tyrosine kinases in biological samples, but has the drawback that results are expressed as images rather than numbers. We also demonstrate here that adding pALK48-SB as an internal standard to biological samples before pTyr western blotting allows normalization of results and expression as a number (the ratio of pTyr-RTK band or spot density to that of the internal standard pALK48-SB). In the case of the two pTyr-EGFR lots from cell line A431 treated with EGF: Lot 10852 consistently gave a dark spot with pTyr 2D western blotting under standard conditions, while the second Lot 13639 consistently gave a light 2D spot. The 3.6 fold difference in the pE/pA ratios was in agreement with the visual observations.

Other considerations: The importance of using an SDS-compatible IEF system for membrane proteins cannot be overstated. Since proteins have maximum solubility in SDS it allows for resolution of most proteins present in complex sample, such as a tumor. In addition, using x-ray film lends itself to high-throughput (n>8 films) can be exposed and developed simultaneously as compared with (n=1-2) using a chemi-imaging system.

Overall Summary: The data presented show the development of a novel phosphoprotein standard pAlk48-SB that can be effectively and reproducibly used as an internal standard for phosphotyrosine western blotting.

Example 2—Activated Receptor Tyrosine Kinase Protein Drivers pTyr-EGFR and pTyr-PDGFR can be Detected in Human Lung Squamous Cell Carcinoma Tissue Using 1D and 2D SDS PAGE Western Blotting Squamous cell carcinoma (SCC) comprises 30% of non-small-cell lung cancer (NSCLC) cases. It has a poor prognosis due to a lack of biomarkers making it intractable to precision medicine. Consensus mutations that are common in NSCLC adenocarcinoma are absent in SCC. Protein analysis of 12 SCC and control lung tissues with 1D and 2D SDS PAGE and western blotting reveal that EGFR and platelet derived growth factor receptor (PDGFR), are preferentially activated by tyrosine phosphorylation in a subset of SCC. A phosphotyrosine protein standard was developed and characterized in order to compare tyrosine phosphorylation between gels and tumors. These data suggest that SDS PAGE/western blotting could serve as a bridge to define subtypes of SCC and identify those tumors that may be responsive to anti-RTK targeted therapies.

Squamous cell carcinoma (SCC) associated with smoking makes up about 30% of non-small-cell lung cancer. So far this subtype remains intractable to precision medicine and has a poor prognosis. Activating mutations of epidermal growth factor receptor (EGFR) and anaplastic lymphoma (ALK) both treatable and common in lung adenocarcinoma, are rare in SCC. Wild type (WT) EGFR protein is often over-expressed in SCC, but remains inactive until a tightly controlled step, tyrosine phosphorylation, occurs. The sequence of events that lead to tyrosine phosphorylation of receptor tyrosine kinases (RTK) is well understood, but has proved difficult to track.

Evidence is provided here that two RTK proteins commonly expressed in normal lung, EGFR, and platelet derived growth factor receptor (PDGFR), remain dormant in some SCC samples but are strongly activated in others by tyrosine phosphorylation. One possible cause is autocrine secretion of ligands by tumor cells. Tumor secretion of EGF for example, would trigger EGFR trans-tyrosine phosphorylation on the cytosolic chain, movement of mitogenic SH2 proteins into the proper position, and subsequent cell division. Genomic testing would not predict this post-translational pathway, rather, direct testing for pTyr-RTK protein is required.

Modern methods of 1-dimensional and 2-dimensional sodium dodecyl sulfate polyacrylamide gel electrophoresis (1D and 2D SDS PAGE) in combination with phosphotyrosine (pTyr) western blotting (WB) are sensitive enough to directly detect pTyr-RTK and pTyr TK proteins in human SCC excised tumor tissue. The key to success of this approach is dissolving the tumor proteins completely by homogenization in a buffer containing sodium dodecyl sulfate (SDS). Tissue samples prepared with SDS clarify upon heating; additional steps, such as centrifugation to remove insoluble "cell debris" containing RTKs may be avoided.

Results are shown for analysis of 12 human SCC samples, 2 adenocarcinoma (ADC) samples, and 11 control lung samples using 1D/2D SDS PAGE in combination with western blotting using enhanced chemiluminescent detection. Of Group 1 samples purchased in 2011: three SCC showed ~200 kDa pTyr-RTK proteins: L3 showed strong pTyr-EGFR plus weak pTyr-PDGFR, L4 showed weak pTyr-EGFR, and L5 showed strong P-Tyr-EGFR plus strong pTyr-PDGFR. An additional SCC tumor showed a strong 30 kDa pTyr breakdown product postulated to be the pTyr-chain of an unknown RTK.

To facilitate numerical expression of results, an internal pTyr-protein standard was generated by cross-reacting a recombinant 48 kDa ALK protein fragment containing the tyrosine kinase domain in vitro, followed by sulfhydryl blockage with iodoacetamide to reduce 2D IEF streaking. Analysis by mass spectrometry showed that the reacted fragment, which we call pAlk48-SB (pA) contained at least 2 phosphotyrosine residues. Standard curves of pA run on 1D SDS PAGE western blots showed good linearity from 0.1 to 2.0 ng protein. Quantification of a commercial pTyr-EGFR standard (pE) by expression of results as the ratio of pE/pA for proteins run on the same gel normalized results from 3 and 10 min film exposures for both 1D and 2D gels.

Similar ratios allowed quantitative comparison of the pTyr-EGFR present in two different lots of pE.

The protein characterization methods described here, labor intensive and relatively low-throughput, are unsuitable for mainstream analysis of SCC cancer testing. It seems likely though, that tumor specimens determined to have specific pTyr-TKs drivers could be used to generate predictive RNA-seq fingerprints. If so, the 1D and 2D SDS PAGE western blot approach could serve as a bridge to diagnostic RNA-seq fingerprinting for mainstream precision medicine targeting.

Lung cancer is the leading cause of cancer deaths in the US, over 150,000 in 2016. About 85% of lung cancers are non-small-cell lung cancer (NSCLC) of which 40% are adenocarcinoma (ADC) characterized by mucin production, and 30% are squamous cell carcinoma (SCC), characterized by keratinization. The latter, associated with smoking, has an especially poor prognosis; average 5 year survival is <50% for Stage 1 and <1% for metastatic Stage 4.

Precision medicine via genomic sequencing has achieved encouraging breakthroughs with regard to ADC. Activating mutations of epidermal growth factor receptor (EGFR) can be detected by genomic analysis in about 10% of Caucasian and 50% of Asian ADC patients. Of these, 70-80% respond to first generation EGFR inhibitors gelfitinib and erlotinib. These drugs preferentially interfere with ATP binding of mutated proteins over wild-type so adverse effects are mild. While not a cure, EGFR inhibitors give patients 6-7 months of extra progression free survival. Anaplastic lymphoma receptor tyrosine kinase (ALK) is a second oncogene activated by mutation in 5-7% of ADC that responds to the inhibitor crizotinib, approved in 2011.

Squamous cell carcinoma (SCC), the subject of this study, is surprisingly different. In 2012, The Cancer Genome Atlas group (TCGA) performed extensive genomic analysis of 178 lung SCC tumors to obtain an overview of the genomic landscape of this cancer, and to identify mutations that might lead to targeted therapies. In contrast to ADC, they found virtually no activating mutations of EGFR, ALK, or KRAS in SCC tumors. Instead a host of complex genomic alterations were detected including on average: 360 exonic mutations, 323 altered copy number segments, and 165 genomic rearrangements per tumor. Exome sequencing revealed a mean somatic mutation rate of 8.1 mutations/megabase (Mb), very high in contrast to that of ovarian cancer (2.1/Mb) and colorectal carcinoma (3.2/Mb). The results suggest that long term exposure to tobacco carcinogens leads to pronounced mutational heterogeneity, without clear activating mutations of targetable tyrosine kinase oncogenes.

Several wild type (WT) RTKs have been implicated in lung SCC. EGFR, overexpressed in >80% of these tumors is the most studied A WT EGFR inhibitor, necitumumab, was recently approved as first-line treatment for lung SCC but adds just 1.6 months on average to overall survival. A biomarker is needed. The hepatocyte growth factor receptor (MET) (11), platelet-derived growth factor receptor (PDGFR) (12), and fibroblast growth factor receptor 1 (FGFR1) (13) have all been implicated in lung SCC as well. FGFR1 is amplified in 20% of lung SCC patients but again, protein expression is not predictive of inhibitor effectiveness. We contend that the lack of correlation between protein expression and RTK inhibitor effectiveness is that there's a post-translational control step in the middle: tyrosine phosphorylation.

Receptor tyrosine kinase (RTK) activity depends on two events, protein expression and subsequent tyrosine phosphorylation. RTKs, exemplified by EGFR, are large transmembrane proteins with a similar mechanism of action. At least seven EGFR ligands (EGF, TGF-$\alpha$, betacellulin, herparin-binding EGF, amphiregulin, epiregullin, and epigen) are known to trigger dimerization by binding to the extracellular domain. Dimerization facilitates trans-phosphorylation of at least five tyrosine residues on the internal C-terminal chain and a sixth residue on the activation loop of the kinase domain. Each phosphotyrosine (pTyr) oligopeptide of 3-6 amino acids, acts as a specific high-affinity binding site for a complimentary SH2 domain on a cytosolic protein. In general, humans have 110 of the latter carrying 120 distinct SH2 domains. In addition these proteins carry various other regulatory domains. Phosphorylation of multiple tyrosine residues on RTKs brings about physical relocation of key SH2-proteins, which in turn initiate cascades of reactions that bring about cell division. It follows that unphosphoryated RTKs are inactive while pTyr-RTKs are active and mitogenic. If pTyr-RTKs are present in high amounts in tumor tissue, it is likely that they are driving cancer growth.

What mutations would cause WT RTKs to become oncogenic drivers of lung SCC? Mutations that cause tumors to secrete ligands for any of the RTKs normally expressed in lung tissue. This includes ligands for EGFR, MET, PDGFR, and FGFR1. Considerable evidence exists for this possibility. Mutations that block endocytosis and breakdown of any of the implicated RTK by suppressing cyclin G-associated kinase.

Direct detection and measurement of pTyr-RTK proteins. The method of 2D SDS PAGE has shown dramatic improvements over the past two decades. In 1997, pTyr-EGFR protein in A431 cells had to be concentrated by immunoprecipitation in order to obtain enough material for detection by western blotting with a pTyr antibody. Since then, continual improvement of 1D/2D SDS PAGE and western blotting transfer methods, in combination with enhanced chemiluminescent (ECL) detection and the availability of high affinity antibodies has increased western blotting sensitivity to the low nanogram range, enough for direct detection.

Importantly, isoelectric focusing (IEF) in tube gels, the classic method developed by O'Farrell has been optimized to be compatible with SDS buffer. The SDS is stripped off proteins during IEF to preferentially bind to micelles of a non-ionic detergent NP-40. The SDS-NP-40 micelles migrate to the acid end of the tube gel where they form a bulb that is cut off and discarded. This method has been standardized, validated, and shown to give a linear responses with varied protein loads.

2D SDS PAGE versus Mass Spectrometry (MS): 2D SDS PAGE cannot identify thousands of protein species in one run as mass spectrometry does. It can, however, focus in on a few low abundance post-translational modifications in a cell lysate containing thousands of abundant protein species, due to commercial availability of high specificity monoclonal antibodies. MS is incompatible with SDS and requires proteolytic digestion before analysis. 2D SDS PAGE is compatible with SDS and detects intact proteins. The two methods are orthogonal and complement one another.

Because of the following points, we hypothesized that our 2D system would be able to detect pTyr-RTKs in human tumor tissue.

The PY20 pTyr antibody is known to have high specificity for pTyr residues. Since activated RTKs have multiple phosphotyrosine residues the western blot sensitivity should be proportionately higher, up by 6-fold for fully phosphorylated EGFR for example. The most important proteins would be the easiest to detect.

The pTyr post-translational modification is rare in general, much less that pSer and pThr for example. Thus, cancer-related changes would not be lost in a field of "passenger" proteins lighting up, as occurs for genome mutational analysis.

The 1D and 2D SDS PAGE systems described here are compatible with SDS, the only reagent capable of dissolving high molecular weight, trans-membrane RTKs with high recovery.

Where would pTyr-RTKs run on SDS PAGE gels? The four RTK proteins implicated in lung SCC are shown in Table 13 along with their theoretical and observed molecular weights, and FDA approved inhibitors. Corresponding biomarkers are not yet in place.

TABLE 13

Receptor tyrosine kinases that are potential drivers of lung SCC. Molecular weight obtained from gene sequence (Cell Signaling PhosphoSitePlus website) versus that observed after taking glycosylation into account as reported in the literature or by Cell Signaling for a validated antibody *, ** human breast cancer.

| RTK associated with SCC | Phosphosite MW | MW of glycosylated RTK protein by SDS PAGE | Examples of inhibitors tested in lung SCC |
| --- | --- | --- | --- |
| EGFR | 134,277 | ~170 kDa (25) ~200 kDa (here) | Necitumumab (9) |
| PDGFR | 122,670 | ~200 kDa * | Crenolanib (26) |
| MET | 155,541 | 190 kDa-glycosylated precursor → 140 kDa + 50 kDa (27) | Crizotinib (11) |
| FGFR1 | 91,868 | 130 kDa (28)** | Dovitinib (29) |

Intact RTKs are heavily glycosylated. Table 13 shows the discrepancy between RTK theoretical MW obtained from genome sequencing compared to the actual glycosylated MW observed on SDS PAGE gels. Glycosylation dramatically increases the MWs for all and narrows differences between them. Images of 2D gels of tumor samples presented later show pTyr-RTKs with large outlines and irregular borders suggesting dramatic protein heterogeneity in charge and size due to heavy glycosylation.

While genomic sequence data predicts a molecular weight of 134 kDa for EGFR, in fact this receptor tyrosine kinase runs much higher because of heavy glycosylation. Branched glycan chains contribute 40-50 kDa to the molecular weight of EGFR, taking it to a physiological MW of 175-200 kDa. Zhen et. al. found that eight out of eleven canonical N-glycosylation sites in human EGFR purified from cultured A431 cells are fully glycosylated; one additional canonical and one atypical site are partially glycosylated. Structures of the glycan chains were deduced via mass spectrometry by assuming the glycan polymers were made up of 4 sugars: hexose, N-acetylhexose, fucose and sialic acid. Sialic acid, a negatively charged terminal sugar on some of the branched glycan chains would impart charge heterogeneity.

In the pages to follow, evidence from 14 human lung cancer tumors (12 SCC and 2 ADC) is shows that pTyr-EGFR and pTyr-PDGFR are present in three lung SCC tissue samples out of twelve. Neither pTyr-RTK was present in 11 lung controls; unphosphorylated EGFR and PDGFR were present in virtually all of the latter.

Results

A total of 14 resected human lung tumors and 11 control lung samples were purchased in two groups from a human biobank as shown in Table 14. Group 1, received in 2011, consisted of five SCC and one ADC sample along with one SCC matched control, and two unmatched disease controls (asthma and tuberculosis). Group 2 received in 2014, consisted of seven SCC and 1 ADC samples along with matched controls for each.

Table 14

Sample identification and receipt dates for 9 matched pairs of lung tumor and adjacent normal tissue, 5 unmatched tumor samples and 2 diseased lung tissue samples used as negative controls. SCC = squamous cell carcinoma, ADC = adenocarcinoma, NAT = normal adjacent tissue. n/a = not available or not analyzed. The two rounds of testing are separated below with the top half of the table labeled L1 to L6 and asthma and tuberculosis controls for Group 1 (2011) and L7 to L14 for Group 2 (2014).

| Kendrick ID | Wt/g | Sex | Age | Stage | Pathological Diagnosis: |
| --- | --- | --- | --- | --- | --- |
| L1 | 1.3 | F | 66 | na | SCC |
| L2 | 1.0 | M | 63 | IIIB | SCC |
| L3 | 1.0 | F | 68 | IIIB | SCC |
| L3 NAT | 0.7 | | | n/a | NAT |
| L4 | 1.2 | M | n/a | IIIA | SCC |
| L5 | 0.4 | M | 48 | III | SCC |
| L6 | 1.0 | M | 74 | IIIB | ADC |
| Asthma control | 1.3 | F | 74 | n/a | Asthma |
| Tuberculosis control | 1.9 | M | 44 | n/a | Tuberculosis |
| L7 | 1.1 | F | 52 | IIIB | SCC |
| L7 NAT | 0.7 | | | na | NAT |
| L8 | 1.2 | F | 52 | IIA | ADC |
| L8 NAT | 1.3 | | | na | NAT |
| L9 | 1.3 | M | n/a | IIIA | SCC |
| L9 NAT | 1.7 | | na | n/a | NAT |
| L10 | 1.0 | M | 63 | IIB | SCC |
| L10 NAT | 1.3 | | | na | NAT |
| L11 | 1.1 | M | 55 | IIIB | SCC |
| L11 NAT | 2.0 | | | na | NAT |
| L12 | 1.0 | M | 70 | IIIB | SCC |
| L12 NAT | 1.8 | | | na | NAT |
| L13 | 1.5 | M | 65 | 1B/2 | SCC |
| L13 NAT | 1.0 | | | na | NAT |
| L14 | 1.0 | F | 43 | IIIA | SCC |
| L14 NAT | 0.8 | | | na | NAT |

Figure 8:
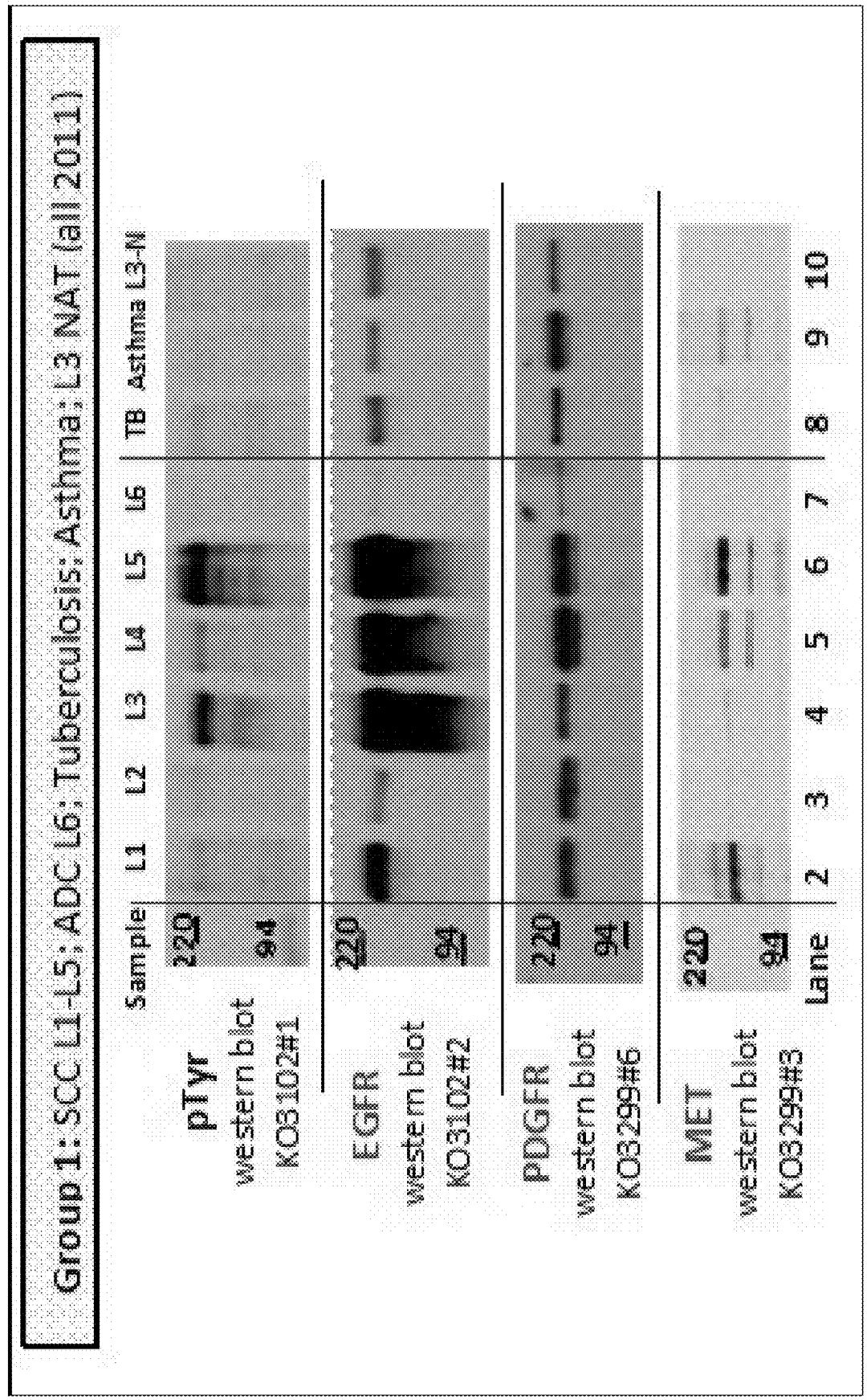

Group 1 Results:

1D SDS PAGE in combination with pTyr western blotting allowed screening of samples to find those with strong pTyr-protein signals, and to see what RTK proteins are expressed. FIG. 8 shows 1D SDS PAGE western blotting results from four antibodies (pTyr, EGFR, PDGFR and MET) for the RTK MW region 94-220 kDa, for the first group of frozen excised human tumor samples and controls purchased from a biobank in 2011. This group consists of five lung SCC samples (L1-L5), one ADC sample (L6), one matched lung control (L3-N), and two diseased lung tissues, tuberculosis (TB) and asthma.

Two out of six tumor samples, L3 and L5, showed strong pTyr bands at ~200 kDa. Tumor L4 showed a fainter band at the same MW. The rest of the tumor samples, as well as the controls, showed very faint pTyr bands between 94 and 220 kDa and were considered unreactive.

The four antibodies gave different patterns for the five SCC samples, supporting the idea of tumor heterogeniety. The ADC sample, L6, was weakly reactive with PDGFR antibody and unreactive with the others. Sample L1 & L2 showed clear EGFR and PDGFR signals; L1 showed detectable MET. The pTyr signal was faint, however, suggesting all three RTKs were inactive. L3 showed strong pTyr, strong EGFR and normal PDGFR. That EGFR was strongly expressed in ⅘ SCC samples give credence to the 80% overexpression number from the literature. EGFR was clearly expressed but at a lower level in the three normal controls.

The EGFR antibody gave a dramatically different 1D pattern than the pTyr antibody. Samples L3, L4 and L5 all showed very dark EGFR bands in contrast to light bands in the 3 controls and in tumors L2 and L6. Sample L1 showed a moderate amount of EGFR, more than the controls but less than L3-5. The ADC tumor, L6, showed the faintest EGFR band of all.

It seems plausible that pTyr-EGFR is a driver of L3 and L5 tumor growth. Unphosphorylated EGFR in L4 probably has little oncogenic activity but would spring into action if an EGFR ligand were secreted. These results are consistent with the observation that EGFR protein expression is not predictive of EGFR inhibitor efficacy. Only tumors containing pTyr-EGFR would be active, not those containing expressed unphosphorylated EGFR.

PDGFR runs at almost exactly the same molecular weight as EGFR and is expressed in all of the samples and controls in varying amounts. It is potentially a cancer driver. The MET bands are consistent with a molecular weight of 140 kDa as described in the literature. Faint MET bands were present in L1, L4, and L5; faint corresponding pTyr bands at that MW were absent in L1 and L4, but appeared in L5 suggesting MET might be active there. Western blots run with ALK (3299 #2) and VEGFR (3299 #7) antibodies were blank between 220 and 94 kDa for all Group 1 samples (not shown) suggesting these proteins are not expressed in these samples.

Figure 9:
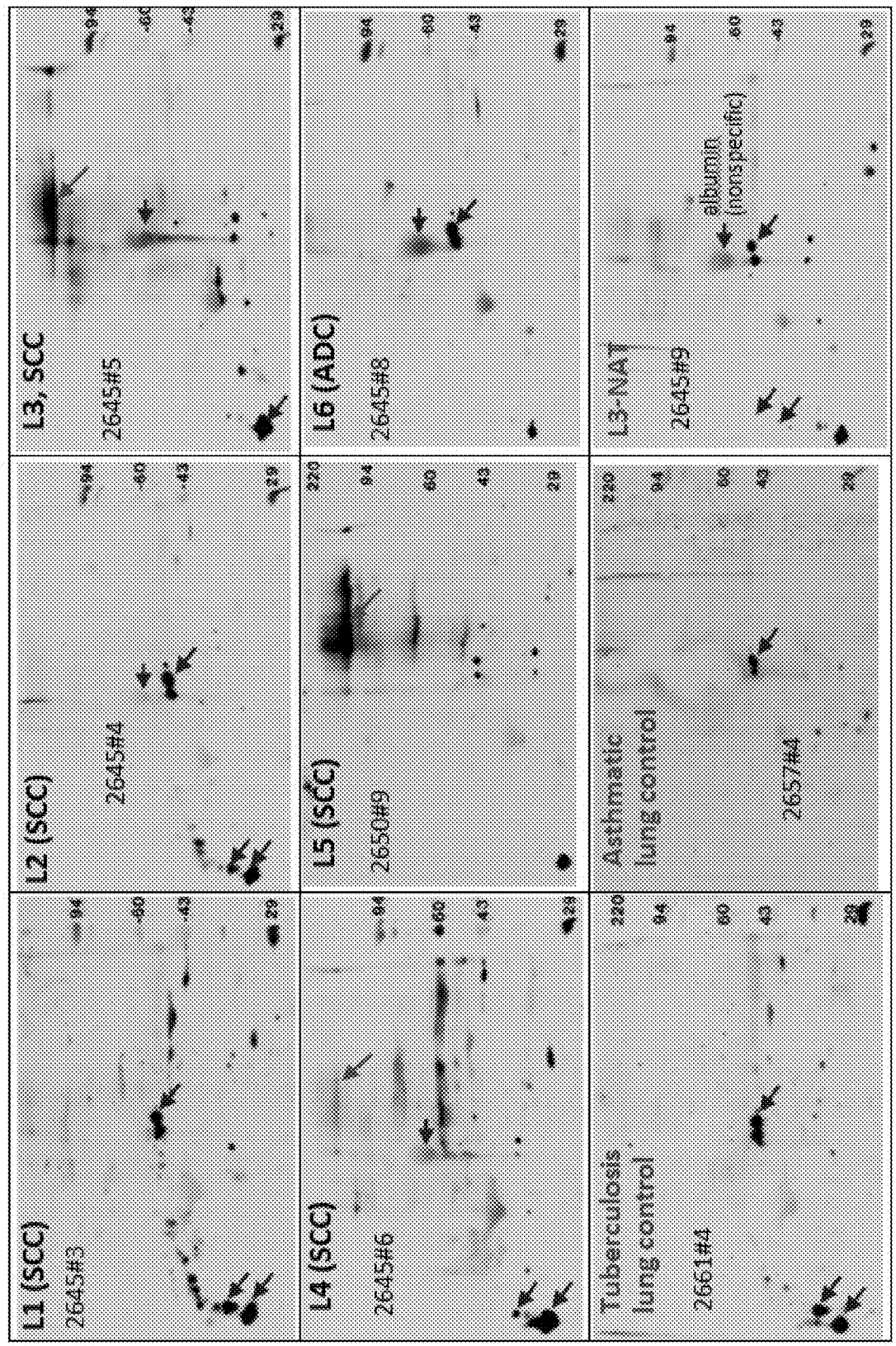

2D SDS PAGE pTyr western blots for Group 1 clarified the 1D results. FIG. 9 shows the 2D SDS PAGE pTyr WB patterns obtained from the nine Group 1 samples shown in FIG. 8. One striking feature of the set is the specificity of the pTyr signal. All gels are loaded with 200 μg of whole cell lysate containing thousands of proteins, yet only a few pTyr proteins are detected. Red (light grey) arrows indicate putative tyrosine kinase proteins that are present in tumor samples but not controls. Blue (Dark grey) arrows indicate pTyr-proteins present in at least one control sample.

Two of the six lung tumor samples, L3 and L5, showed a strong putative pTyr-RTK signal at ~200 kDa. Tumor L4 showed a faint pTyr-protein signal at ~200 kDa and a strong streaky tyrosine kinase protein at 60 kDa. The pTyr-protein spots at ~200 kDa in samples L3 and L5 are the strongest spots in the sample set. The high molecular weight and glycosylated appearance suggest these proteins are receptor tyrosine kinases. Sample L4 shows a faint pTyr-glycosylated protein in the same region, also presumptive RTK. Several lower molecular weight (≤50 kDa) pTyr proteins are detected in both samples and controls. For example a dark pTyr spot at about 35 kDa on the acidic side of the gels is present in ⅔ controls and ⅚ tumor samples. The function and identity of these proteins is unknown.

Nonspecific binding, determined by comparison of the PVDF blot Coomassie pattern with the film images, is also seen in FIG. 9. Two of the MW markers, phosphorylase A (94 kDa) and carbonic anhydrase (29 kDa) show non-specific binding on most of the gels. A large amount of centrally located albumin frequently shows a non-specific binding signal. A moderate of nonspecific binding does not interfere with interpretation. Lining up the MW markers showing nonspecific binding for example is useful for comparing patterns. Nonspecific pTyr antibody binding by the high abundance human albumin spot is also useful for lining up patterns.

Which pTyr-RTK is Present in L3 and L5: EGFR, PDGFR or a Mixture?

1D SDS PAGE works well as a screening mechanism to say which tumor samples are expressing a strong pTyr-protein signal. But which RTKs are activated? We know from 1D western blotting that VEGFR and ALK are not expressed in these tumors so they're eliminated. Likewise, the molecular weight (MW) of MET (110 kDa) and FGFR1 (130 kDa) do not match the pTyr band. However, the MW of glycosylated EGFR and PDGFR both match that of the pTyr-unknown protein and each other; 1D SDS PAGE cannot provide a definitive answer.

Figure 10:
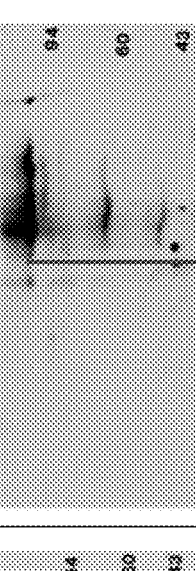

2D western blots: A second approach towards identifying the active RTK in L3 and L5 was to analyze each of the two tumors using 2D SDS PAGE WB with three different antibodies: pTyr, EGFR and PDGFR. Separating the proteins first by charge using isoelectric focusing, followed by 1D SDS PAGE might clarify what is going on. Results are shown in FIG. 10.

The left column indicates gel treatment, middle shows results for L3 while right column shows results for L5. The first row shows pTyr western blots from FIG. 8. The next two rows show aligned images from EGFR and PDGFR western blotting, while the bottom row shows the aligned images from L3 and L5 Coomassie blue stained replicate 2D gels. The latter show the major albumin protein used to line up the images.

These results suggest that pTyr-EGFR is the main RTK driver in tumor L3. PDGFR mostly appears as low molecular weight breakdown fragments. A small portion of the pTyr spot signal is co-migrating with PDGFR (green arrow) but the great majority of it co-migrates with EGFR. The film exposures for EGFR are short, just 10 seconds, to show the major charge species. Longer exposures show less abundant species that appear in the pTyr western blot.

In contrast, The 2D gel pattern for the diffuse ~200 kDa RTK spot in SCC L5 suggests both proteins are active. The PDGFR is mostly intact and comigrates with some of the pTyr signal. Antibodies against EGFR and PDGFR are binding to different epitopes, possibly glycans, making exact matching between gels difficult.

Stripping and then reprobing the same PVDF membrane with a second antibody should provide unequivocal results. Images of the second, reprobed pattern may be easily colorized and then superimposed on the first using software such as Adobe Photoshop Elements. The hypothesis was that the glycosylated pattern obtained from pTyr western blotting of sample L5 would match either the EGFR or PDGFR pattern, but not both. In fact, the answer was both.

Figure 11:
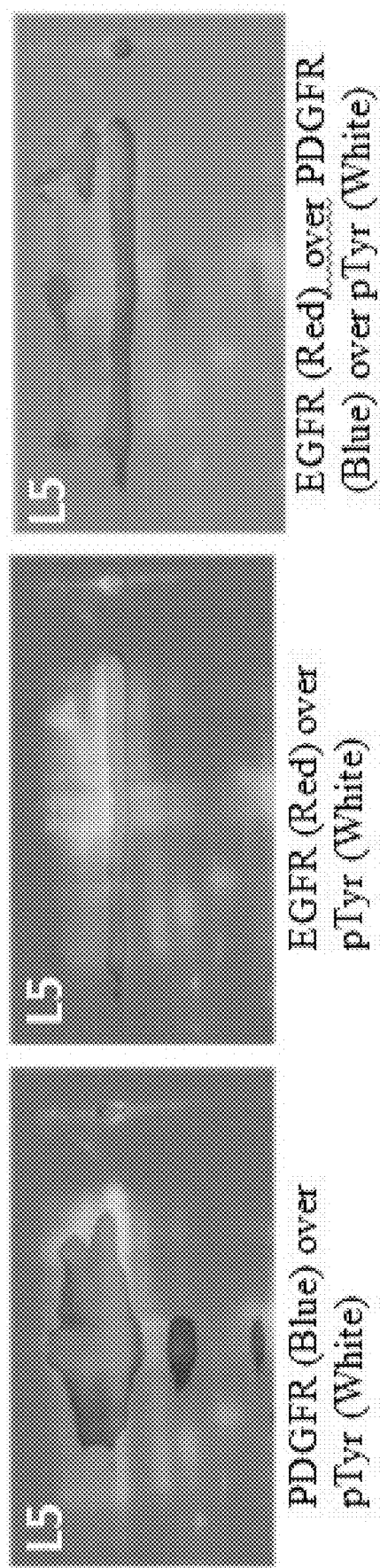
FIG. 11 shows a superimposable color-coded images from 2D western blots performed with three different antibodies on the same 2D gel (2831 #5) loaded with 200 ug of SCC L5. The order of western blotting was PDGFR WB, strip, pTyr WB, strip, EGFR WB.

FIG. 11 shows results for a triple strip and reprobe western blot experiment with sample L5. After 2D SDS PAGE of heavily loaded sample L5 (200 ug) the proteins were transferred to a PVDF sheet under standard conditions. First PDGFR western blotting was performed, followed by stripping; then pTyr western blotting followed by stripping; then EGFR western blotting. The resultant superimposable images were carefully overlaid by matching marked corners. EGFR was color-coded in red, PVDFR in blue, and pTyr in white. The EGFR and PDGFR overlay different portions of the white pTyr hazy areas but mostly do not overlay each other.

It should be noted that PVDF stripping is temperature dependent and fussy. Technical problems became apparent for some strip and reprobe pairs but not others. In some cases, the primary antibody used after stripping gave false positive spots as if the pre-blocking step was negated. This was easily detected—the second primary ab pattern (after stripping) did not match the first primary pattern from the same antibody on a duplicate gel.

Stripping and reprobing conclusions: Despite occasional problems with this method, there is no reason to doubt the results of FIG. 11. Stripping and reprobing unequivocally revealed the presence of both pTyr-EGFR and pTyr-PDGFR in lung SCC L5.

Group 21D Western Blot Screening Results Showed No ~200 kDa pTyr Proteins.

Figure 12:
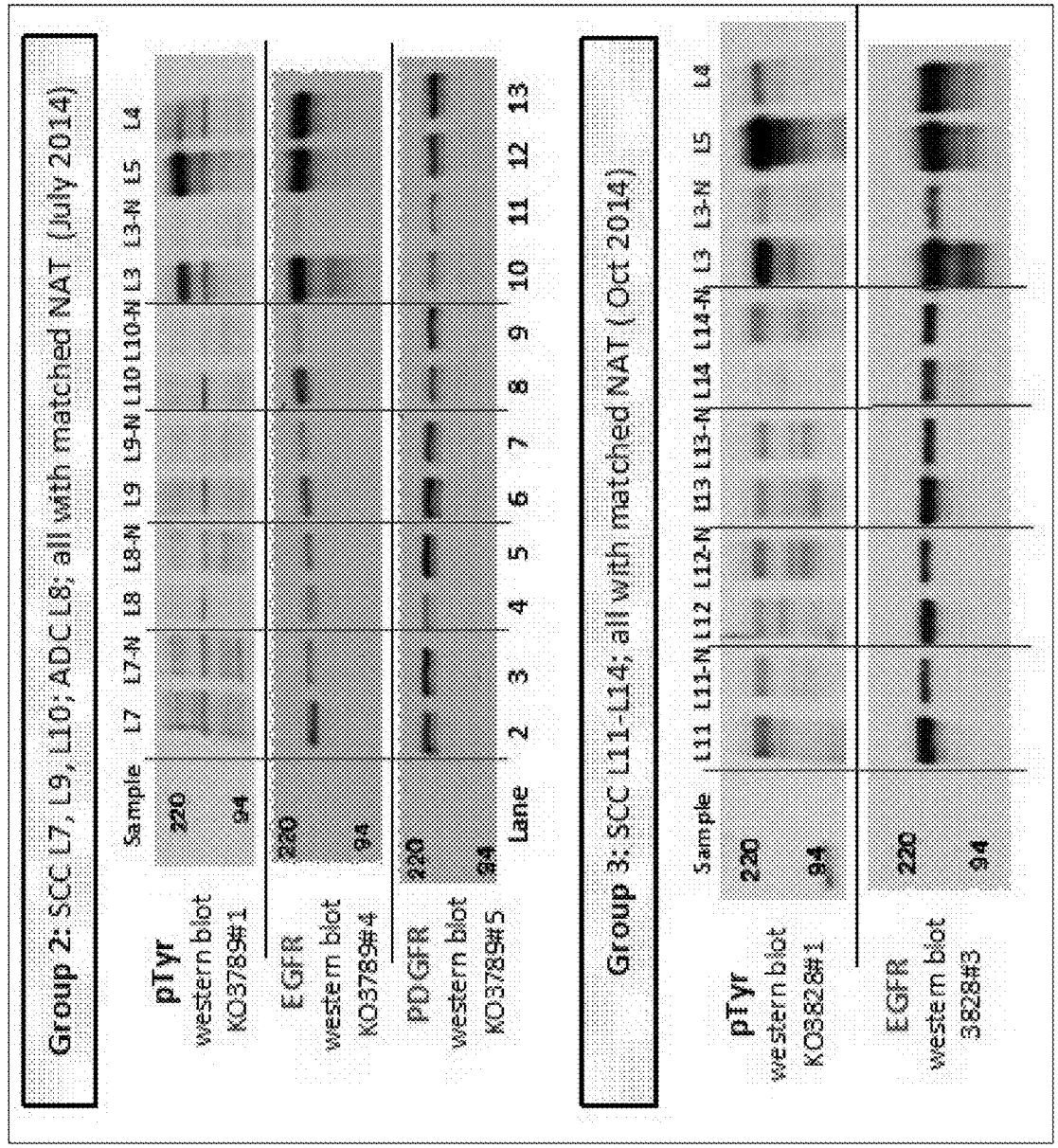
FIG. 12 shows SDS PAGE western blot patterns from Group 2 tumor sample L7-L14 with Normal Adjacent Tissue (N) samples for comparison.

The 8 tumor and matching control samples received in 2014 were screened by 1D pTyr western blotting. As a positive control, fresh aliquots of 2011 samples L3, L3-NAT, L5 and L4 were thawed and run alongside these Group 2 tumors L7-L10 with NAT controls, and Group 3 tumors L11-L14 with NAT controls. Results are shown in FIG. 12. The pTyr bands in the eight tumor samples purchased in 2014 were much fainter than the strong bands in the L3 and L5 control lanes. Only sample L11 showed a noticeable increase over the corresponding control to bring it to about the level of the L4 RTK band. All Group 2 tumor samples showed small or moderate amounts of EGFR, less than the pronounced result observed for L3-5. PDGFR was present in detectable levels in tumor and control samples L7-L10; PDGFR western blot analysis was not performed for L11-L14 tumor and control samples.

Stability of Tumor pTyr-RTK Signal SDS at −80° C.

Forced RTK Degradation: Initial mass spectrometry attempts to identify RTK(s) in samples L3 and L5 failed. A 2012 attempt to deglycosylate these samples using a Glyko Enzymatic deglycosylation kit from Prozyme caused a 30 kDa pTyr-degradation product to appear. An experiment was set up where L3 and L5 aliquotes were incubated with 0-4 Glyco enzyme combinations at 37° C. for 3-6 hours. At the end, samples were lyophilized and redissolved in SDS buffer for analysis by 2D SDS PAGE with pTyr western blotting. The deglycosylation treatments only partially worked, but, interestingly, a tight 30 kDa pTyr degradation spot appeared in each of the eight 2D gels, regardless of whether deglycosylation enzymes were present or not.

Figures 13A, 13B, 13C, 13D, 13E, 13F:
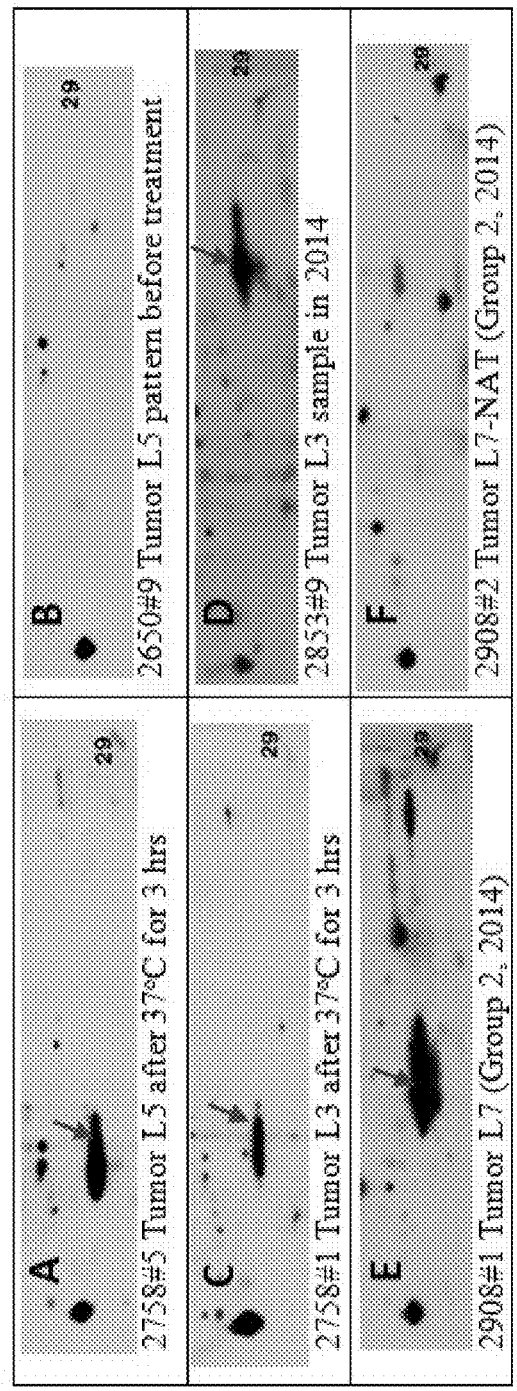

FIG. 13 shows the new ~30 kDa pTyr spot present in tumor L5 incubated for 3 hrs at 37° C. (A), but missing from the original homogenate (B). A similar spot was seen in incubated L3 (C) that was missing from the original sample. FIG. 13D shows a similar spot (D) present in a pTyr WB obtained from Tumor L3 in 2014, suggesting sample degradation had occurred in this tube only, for unknown reasons. Finally a similar strong pTyr spot appeared at ~30 kDa in Tumor L7 (E) but not L7-NAT. (F). This set of 8 samples, purchased in 2014, showed no high MW RTK signal. We hypothesize that that this sample originally possessed a strong pTyr-RTK that was lost because of inadvertent sample warming at some point.

Tumor Tissue Degradation during storage at −80° C.: Individual tubes of L3 and L5 tumor sample prepared in SDS buffer with protease and phosphatase inhibitors were stable at −80° for at least 3 years. However, all the original L3 and L5 aliquots stored at −80° C. had been used up by November 2014. The pTyr 200 kDa signal was greatly diminished for material from aliquots that had been refrozen and stored at −80° C. after a small amount of material was removed. Half of each original tumor sample had been refrozen on dry ice and stored at −80° C. for 3.6 years from 2011 to November 2014. It was assumed that raw tissue would retain pTyr signal at −80° C., similar to the frozen aliquots. In actuality, this was not true. the pTyr signal for the stored L3 and L5 samples was barely visible after homogenization in SDS buffer in 2014.

Preparation and Testing of a pTyr-Protein Internal Standard

Tracking activated RTKs in tumors by pTyr western blotting has the potential to provide important information complementary to that from genomic sequencing and mass spectrometry. One major problem, however, is that western blot results are presented as complex images and comparing images from more that 2-3 samples is difficult.

In theory, this problem can be remedied by adding a known amount of an internal pTyr-protein standard to each sample, and then expressing results as the ratio of the density of each unknown band/spot to that of the standard. Such normalization could correct for differences in film exposure times, and for ECL signal variation between runs. It would allow expression of pTyr results as a number rather than a picture. Relative amounts of individual activated RTKs such as pTyr-EGFR, could easily be compared between samples.

To that end, we have developed and performed preliminary testing of a pTyr-protein standard called pTyr-ALK48-SB (pA). A 48 kDa recombinant HIS-tag fragment of anaplastic lymphoma kinase (ALK) containing the tyrosine kinase domain was in vitro phosphorylated and, then sulfhydryl-blocked (SB) as described in methods.

2D SDS PAGE pTyr western blotting was performed on: the ALK48 starting material, the in vitro phosphorylated ALK48 (pTyr-ALK48) and phosphorylated and sulfhydryl blocked pTyr-Alk48-SB (pA). A 2D gel heavily loaded with one μg of the ALK48 starting material gave no pTyr 2D western blot signal (not shown). In contrast, FIG. 14 shows the 2D pattern of 20 ng of pTyr-ALK48 after the kinase reaction (top), and of pA, obtained after the sulfhydryl blocking step (bottom). Sulfhydryl blocking with iodoacetamide tightened up the isoelectric focusing (IEF) pattern, possibly by preventing intermolecular disulfide bonding during the overnight IEF step. Disulfide-connected dimers might cause streaking during IEF but would not appear on the subsequent SDS slab gel because the IEF tube gel is equilibrated in SDS buffer containing reducing agent before the $2^{nd}$ dimension.

Mass spectrometry was used to compare the starting material, ALK48, with the kinase-reacted product, pTyr-ALK48-SB (pA), to determine which pTyr residues were reacting with the pTyr PY20 monoclonal antibody. Analyses performed in triplicate on the two samples showed phosphorylation of at least two tyrosine residues 69 and 256 as shown in FIG. 15.

Linearity of the 1D SDS PAGE pTyr western blot response: To determine the useful range of pA as an internal quantitative standard, increasing amounts of two identically prepared lots (1 and 2), from 0.1 to 4 ng/lane, were loaded on 1D SDS PAGE gels along with a fixed amount of a commercial pTyr-EGFR standard (pE). See FIG. 16

Each lot of pA was run on triplicate 1D gels followed by pTyr western blotting. Three and 10 minute film exposures from each were scanned with a calibrated laser densitometer and the band densities determined using TotalLab 1D software. FIG. 16 shows one typical pTyr western blot image (10 minute film exposure) from each lot along with the corresponding plot of band densities versus load for the range 0.1-2 ng of pA. The curves leveled off at the 4 ng point which was omitted from the graphs. The pA internal standard gave a linear response for each film over this range. Average $R^2$ values for the six pA curves per run were 0.9861+/−0.013 for lot 1 (GP48 #1-3) and 0.9876+/−0.007 for lot 2 (GP56 #1-3). Lots 1 and 2 of pA, identically prepared, give essentially the same western blot results and are considered equivalent.

The pE positive control is an SDS cell lystate from EGF treated A431 cells, sold as a positive control for PY20 pTyr antibody. No claims were made by Exalpha regarding the amount of pTyr-EGFR in different pE lots. In fact, the 1D pTyr-EGFR signal was considerably stronger for the first lot purchased, (lot 10852) than the second (lot 10369). This provided an opportunity to use the pA standard for relative quantification of pTyr-EGFR in two different samples, and also to test the hypothesis that expressing results as a ratio would normalize film differences, giving the same result regardless of film exposure conditions.

1D results: The 1 ng pA load, in the linear region for both 3 and 10 min film exposures, was used to normalize the pTyr-EGFR band density values by expressing them as the pE/pA ratio on each of the six films per sample. Results are shown in Tables 15 (lot 10852) and 16 (lot 13639). As expected, agreement between the pE/pA ratio obtained from 3 and 10 min film exposures from the same western blot (labeled with the same #) was observed. More variability was seen between the replicate western blots than between film exposures.

TABLE 15

Lot 10852 pTyr-EGFR band density values expressed as a ratio of the 1 ng pA band on triplicate gels (GP48#1-3) for 3 min and 10 min films. The final value is the average ratio from 2 films each for 3 gels.
Lot 10852: pE/pA Band Density Ratios (GP48#1-3)

| Lane | 3 min #1 | 3 min #2 | 3 min #3 | 10 min #1 | 10 min #2 | 10 min #3 |
|------|----------|----------|----------|-----------|-----------|-----------|
| 4    | 1.8      | 1.0      | 2.3      | 1.9       | 1.3       | 2.1       |
| 6    | 1.9      | 1.5      | 2.3      | 2.0       | 1.7       | 2.2       |
| 8    | 1.4      | 0.9      | 2.3      | 1.4       | 1.1       | 2.2       |
| 10   | 1.3      | 0.4      | 1.2      | 1.4       | 0.9       | 1.5       |
| 12   | 1.7      | 0.7      | 1.9      | 1.8       | 1.0       | 1.9       |
| 14   | 1.7      | 0.7      | 2.0      | 1.8       | 1.0       | 2.0       |
| Ave  | 1.6      | 0.9      | 2.0      | 1.7       | 1.2       | 2.0       |
| SD   | 0.3      | 0.4      | 0.4      | 0.2       | 0.3       | 0.3       |
|      | 3 min Ave |         | 1.5      | 10 min Ave |          | 1.6       |
|      | 3 min SD  |         | 0.61     | 10 min SD  |          | 0.43      |
|      | Final: pE/pA Average |  |     | 1.56       | SD        | 0.52      |

TABLE 16

Lot 13639 pTyr-EGFR band density values expressed as a ratio of the 1 ng pA band on triplicate gels (GP56#1-3) for 3 min and 10 min films. The final value is the average ratio from 2 films each for 3 gels.
Lot 13639: pE/pA B and Density Ratios (GP56#1-3)

| Lane | 3 min #1 | 3 min #2 | 3 min #3 | 10 min #1 | 10 min #2 | 10 min #3 |
|------|----------|----------|----------|-----------|-----------|-----------|
| 4    | 0.21     | 0.15     | 0.20     | 0.32      | 0.29      | 0.33      |
| 6    | 0.18     | 0.15     | 0.20     | 0.30      | 0.29      | 0.33      |
| 8    | 0.22     | 0.13     | 0.21     | 0.33      | 0.29      | 0.33      |
| 10   | 0.20     | 0.13     | 0.22     | 0.34      | 0.25      | 0.37      |
| 12   | 0.22     | 0.12     | 0.19     | 0.34      | 0.31      | 0.37      |
| 14   | 0.22     | 0.10     | 0.20     | 0.34      | 0.26      | 0.38      |
| Ave  | 0.21     | 0.13     | 0.20     | 0.33      | 0.28      | 0.35      |
| SD   | 0.02     | 0.02     | 0.01     | 0.02      | 0.02      | 0.02      |
|      | 3 min Ave |         | 0.18     | 10 min Ave |          | 0.3       |
|      | 3 min SD  |         | 0.04     | 10 min SD  |          | 0.04      |
| Final: pE/pA Average | | | | 0.25 | SD | 0.08 |

The average pE/pA ratio of lot 10852 was 1.56+/−0.52 while that of lot 13639 was 0.25+/−0.08. According to this 1D western blot assay, pE Lot 10852 contains 6.2 times more pTyr-EGFR than Lot 13639. The internal standard allowed the differing amounts of pTyr-EGFR between the two lots to be expressed as a number.

Linearity of the 2D SDS PAGE pTyr western response: Only one sample is loaded on a 2D gel so an internal standard curve is not possible. Instead, the loaded ratios of pE/pA were deliberately varied over a set of eight 2D gels to test whether normalized pTyr spot density measurements are meaningful for this multi-step method, as shown in Table 17. Loads of 1 ng and 2 ng were chosen for pA, because both were in the linear range for 3 and 10 min films for 1D gels. Since 2D gels can handle higher volumes and heavier loads than 1D, 10 and 20 ul loads were chosen for the pE lots. Page 3016 2D gels were loaded with pE lot 10852; page 3017 2D gels with lot 13639. If the multiple steps of 2D SDS PAGE western blotting are true, then the measured spot density ratios will be proportional to the loaded sample ratios.

TABLE 17

Loading scheme for 2D SDS PAGE pTyr western blots used to quantify the pTyr-EGFR difference between Exalpha pE lots 10852 and lot 13639.

| Load 1 | Load 2 | Load 3 | Load 4 |
|--------|--------|--------|--------|
| Ratio = X | Ratio = 2X | Ratio = 0.5X | Ratio = X, double load |
| 10 ul pE | 20 ul pE | 10 ul pE | 20 ul pE |
| 1 ng pA | 1 ng pA | 2 ng pA | 2 ng pA |

Image of the results from 3 and 10 minute film exposures from 2D pTyr western blots loaded according to Table 17 (2 ng pA, 20 ul pE) for lot 10852 are shown in FIG. 18. After alignment of all 16 images in the set with Progenesis SameSpots, the pA and pE spot outlines shown in the right hand panel were transferred to all the images. Background (Average on Boundary) was automatically subtracted to get the spot density values. Data was transferred to Excel for calculation of ratios.

Table 18 includes pE/pA ratios from the 16 film exposures (3 and 10 minute for 8 gels) for lots 10852 (p3016) and 13639 (p3017). Corresponding plots of pE/pA spot density ratios determined using Progenesis SameSpots software versus deliberately loaded pE/pA sample ratios with zero included as a point are shown in FIG. 18. The Y axis varies between the two plots because the amount of pTyr-EGFR in 10852 is greater than that in 13639. For both plots a linear relationship is seen between the pE/pA density ratios versus the actual loaded ratio for both samples. The curve for lot 10852 gives an $R^2$ values of 0.9960, while that for lot 13639 gives 0.9808.

TABLE 18

Results from measurement of integrated density above background of the pE and pA spots from Exalpha pE lots 10852 and 13639.

| ID # | FilmExp. | Spot Density pE/pA | Average | Loaded Ratio |
|------|----------|--------------------|---------|--------------|
| 3016#1 | 3 min  | 2.3  | Ave 1.7  | X |
| 3016#1 | 10 min | 2.0  | SD 0.6   |   |
| 3016#2 | 3 min  | 1.4  |          |   |
| 3016#2 | 10 min | 1.0  |          |   |
| 3016#3 | 3 min  | 2.7  | Ave 3.7  | 2X |
| 3016#3 | 10 min | 2.4  | SD 1.4   |   |
| 3016#4 | 3 min  | 5.4  |          |   |
| 3016#4 | 10 min | 4.2  |          |   |
| 3016#5 | 3 min  | 0.5  | Ave 0.7  | 0.5X |
| 3016#5 | 10 min | 0.6  | SD 0.2   |   |
| 3016#6 | 3 min  | 0.9  |          |   |
| 3016#6 | 10 min | 0.9  |          |   |
| 3016#7 | 3 min  | 2.4  | Ave 1.9  | X |
| 3016#7 | 10 min | 2.0  | SD 0.4   | (double |
| 3016#8 | 3 min  | 1.7  |          | loads) |
| 3016#8 | 10 min | 1.6  |          |   |
| 3017#1 | 3 min  | 0.52 | Ave 0.51 | X |
| 3017#1 | 10 min | 0.41 | SD 0.07  |   |
| 3017#2 | 3 min  | 0.56 |          |   |
| 3017#2 | 10 min | 0.56 |          |   |
| 3017#3 | 3 min  | 0.64 | Ave 0.88 | 2X |
| 3017#3 | 10 min | 0.76 | SD 0.22  |   |

TABLE 18-continued

Results from measurement of integrated density above background of the pE and pA spots from Exalpha pE lots 10852 and 13639.

| ID # | FilmExp. | Spot Density pE/pA | Average | Loaded Ratio |
|---|---|---|---|---|
| 3017#4 | 3 min | 0.97 | | |
| 3017#4 | 10 min | 1.14 | | |
| 3017#5 | 3 min | 0.32 | Ave 0.20 | 0.5X |
| 3017#5 | 10 min | 0.25 | SD 0.10 | |
| 3017#6 | 3 min | 0.10 | | |
| 3017#6 | 10 min | 0.14 | | |
| 3017#7 | 3 min | 0.50 | Ave 0.56 | X |
| 3017#7 | 10 min | 0.70 | SD 0.11 | (double |
| 3017#8 | 3 min | 0.44 | | loads) |
| 3017#8 | 10 min | 0.60 | | |

Data from these tables can be used to quantify the pTyr-EGFR difference between pE lots 10852 and 13639 as shown in Table 19. Again, more variation is seen between different 2D gels than between normalized film exposures for the same gel. To use results from all eight gels, the pE/pA ratios for half loads were doubled, while those for the 2X gels were halved to get X equivalents. Results shown in Table 19 summarize results of a quantitative comparison of the two lots obtained using all eight 2D SDS PAGE gels for each sample. The average pE/pA ratio of lot 10852 was 1.73+/−0.5 (1D value 1.56+/−0.46) while that of lot 13639 was 0.48+/−0.10 (1D value 0.25+/−0.09). According to the 2D western blot assay, pE Lot 10852 contains 3.6 times more pTyr-EGFR than Lot 13639 (versus 6.2 fold for the 1D western blot assay).

TABLE 19

Comparison of pTyr-EGFR in two lots of A431 cell lysate standard (pE) from Exalpha analyzed on 2D SDS PAGE western blots. The two different pE lots (10852 and 13639) were identically loaded on sets of eight 2D gels as described in Figure 18. Measured pE/pA spot density values for gels loaded at 2X were divided by 2; measured values for gels loaded at 0.5X were multiplied by 2, to obtain comparable X values for all eight gels. The lot 10852 average pE/pA value was 1.73, while the corresponding value for lot 13639 was 0.48. Thus the fold difference for lot 10852 versus 13639 is 3.6 (1.73/0.48).

| lot 10852 pE/pA Ratio | | | lot 13639 pE/pA Ratio | | |
|---|---|---|---|---|---|
| Gel # | Adjustment | Final | Gel # | Adjustment | Final |
| 3016#1 | X (no change) | 2.2 | 3017#1 | X (no change) | 0.47 |
| 3016#2 | X (no change) | 1.2 | 3017#2 | X (no change) | 0.56 |
| 3016#3 | 2X/2 | 1.3 | 3017#3 | 2X/2 | 0.35 |
| 3016#4 | 2X/2 | 2.4 | 3017#4 | 2X/2 | 0.53 |
| 3016#5 | 0.5X*2 | 1.1 | 3017#5 | 0.5X*2 | 0.57 |
| 3016#6 | 0.5X*2 | 1.8 | 3017#6 | 0.5X*2 | 0.24 |
| 3016#7 | X (no change) | 2.2 | 3017#7 | X (no change) | 0.6 |
| 3016#8 | X (no change) | 1.7 | 3017#8 | X (no change) | 0.52 |
| | Ave | 1.73 | | Ave | 0.48 |
| | SD | 0.5 | | SD | 0.1 |
| | CV | 29 | | CV | 26 |

The SCC tumors contain proteins that cause pA streaking: Interestingly, adding the pA standard to human tumor samples L3 and L4, followed by 2D pTyr western blot analysis gave a surprising result. The pA standard streaked as shown in FIG. 13. We hypothesize that proteins containing SH2 domains are binding complementary pTyr-aa sites during IEF, after the SDS is stripped off the proteins by NP-40 micelles.

pE/pA ratios might be an imperfect measure of tumor driver abundance, but far better than pictures. FIG. 20 shows a 30 minute film from tumor L3 run in 2011, (versus a 5 minute exposure of the same film in FIG. 9) alongside a 10 minute exposure of the pA/pE standard mix run in 2016. Full films are shown, to reveal the PVDF corner marks used to match Coomassie stained PVDF images showing total protein to the western blot films. Note, that the pA standard was not available in 2011. Its position, had it been added, would have been to the left of its position in 2016, out of the way of the great bulk of the tumor pTyr signal.

The red arrow on the left image points to pTyr-EGFR in L3, the green arrow points to a lower abundance, lower molecular weight RTK, possibly FGFR1. The latter is faint on the 5 minute film shown in FIG. 9. Had pA been added to as a standard, the ratio of pTyr-EGFR to 1 ng pA would have been say, roughly, 10 in 2011, while that of putative pTyr-FGFR1 would have been roughly 1. Overall, inclusion of the pA standard for 1D or 2D gels would provide a meaningful way to compare expression between proteins in the same sample or between two samples or gels and convert images to numbers that can be more easily compared.

Streakiness of the pA spot might increase error; long film exposures might push the pA spot density outside of the linear range. Even so, numerical estimates of relative pTyr-RTKs amounts would be useful for trying to determine which pathways are in place for individual SCC tumors.

DISCUSSION

Even though WT EGFR is overexpressed in ~80% of SCC, necitumumab, the newest WT EGFR inhibitor, prolongs overall survival by less than two months, a disappointing result. Paik and Rudin noted in 2016 that more than 60% of lung ADC patients have single actionable RTK targets, detectable by genomic analysis, while lung SCC patients have effectively 0%. Our results may shed light on this dilemma. FIGS. 8 and 12, both 1D western blots, indicate that at least three RTKs, EGFR, PDGFR, and Met, and perhaps more are commonly expressed in normal lung and sometimes overexpressed in SCC. Such expressed RTKs would be inactive until corresponding ligands induced by mutation bring about tyrosine phosphorylation and the subsequent cascade of reactions engendered by SH2 domain-containing proteins. Tyrosine phosphorylation, detectable by pTyr western blotting using the PY20 antibody, was observed in three of twelve SCC samples.

Importantly, in one of the three positive samples it appeared that two different pTyr-RTKs were active simultaneously. Sample L5 showed pTyr-RTK signal matching both pTyr-EGFR and pTyr-PDGFR patterns that were different from each other. The L3 tumor, in hindsight, showed a faint pTyr signal that was at the appropriate molecular weight for FGFR1. If so, it seems likely that the two RTKs are driving different clones in the same tumor. Relatively large pieces of tumor tissue were homogenized (0.5-1 gm of tissue) which would include multiple clones, if present.

Considerable precedent exists for such autocrine stimulation of tumors. In fact SCC tumor is listed as a case where TGF-alpha was the autocrine signal released that stimulated EGFR activity. Unfortunately there are multiple ligands for each RTK, for example, there are seven known ligands for EGFR and 22 for FGFR1. Diagnosis by ligand identification would be difficult.

In this exploratory work with excised lung tumor tissue purchased from a tissue bank, only SCC samples purchased in 2011 showed a strong pTyr-RTK signal; samples purchased in 2014 showed no high molecular weight signal above background. It is not clear if this is serendipitous, or if the 2014 samples were compromised in some way. One of the 2014 samples showed a strong 30 kDa pTyr-protein that was reminiscent of forced breakdown products observed previously in experiments with L3 and L5. This suggests at least one of the 2014 samples was compromised.

The new pTyr-protein might be from enzymatically clipped C-terminal fragment containing all the pTyr residues. Four charge isoforms, possibly due to different numbers of negatively charged pTyr residues, appeared for these breakdown products. Phosphotyrosine-induced changes in RTK isoelectric points, obscured in the intact protein by heavy glycosylation, would be visible in the C-terminal chain. Storage by the tissue bank in liquid N2 was as long as seven years in some cases. All activity was lost for the leftover tumor halves refrozen on dry ice and stored at −80° C. for 3 years.

To our knowledge, these results are novel. Rikova et al. analyzed 150 NSCLC samples in 2007 using 1D SDS PAGE with pTyr western blotting in combination with RTK identification by mass spectrometry. SDS interferes with mass spectrometry however, and, as far as we can tell, was omitted during sample preparation. A centrifugation step was used to clarify prepared samples. In retrospect, it seems likely that RTK recoveries would have been low for samples analyzed by the Rikova group.

Mass Spectrometry of pTyr-RTK spots: Two attempts were made to identify the pTyr-RTK species by mass spectrometry (LS/MS/MS) at the Columbia University Protein Core Facility. Putative RTK spots were cut from large format 2D gels that had been heavily loaded with 600 μg protein and stained with Coomassie blue. The appropriate area was cut since the candidate spots were not visible. No RTK peptides were detected. Since glycosylation was likely an interfering factor, attempts were made to focus the diffuse pTyr-protein profiles into sharper spots by deglycosylation. These attempts failed, and in fact served to force protein breakdown. A new 30 kDa pTyr-protein appeared at ~30 kDa that we hypothesize is the clipped C-terminal tail.

Importance of an internal pTyr internal standard: ECL western blotting is a common procedure performed by many laboratories. Comparing results from different labs is difficult, however, because the ECL reagent light emission, which imparts very high sensitivity, varies dramatically over the first 2 hours. Absolute band density may vary between identically loaded gels. The density variation may be normalized for pTyr by adding 1 ng of the internal pA standard and expressing results as the ratio of an unknown pTyr-RTK band to that of the standard on the same gel.

The pA standard also serves as a positive control, providing evidence that gel running, transblotting, and immunostaining steps were all acceptable. Two lots of the 48 kDa internal pTyr standard pA, run on different days, gave a linear response on both 3 min and 10 minute film exposures as shown in FIG. 16. Normalization of the pTyr western blot signal allows comparison of corresponding pTyr proteins in different samples. The fold difference between the two lots of pTyr-EGFR in the two lots of A431 cells was 6.2 as determined by 1D versus 3.6 as determined by 2D SDS PAGE western blotting. The standard error (mean/SD*100) was 32% (n=3 gels each) and for 2D was 26% (n=8 2D gels each). The results suggest that there is more variation between gels than between film exposures, probably in the transblotting step.

Additional sources of error for pTyr-RTK quantification in tumor tissue: Obviously, the exact amount pTyr-RTK in a tumor sample cannot be deduced by methods described here. The percentage of tumor tissue may vary within the large amount of tissue sampled, as may the number of clones with different pTyr-RTKs. The number of filled pTyr sites per RTK molecule may vary between tumors. The ligand levels probably vary with time. Autocrine secretion would be self-selective. Even so, knowing which tumors contain pronounced amounts of pTyr-EGFR as expressed by a pTyr-E/pA ratio of say 20 versus those with a ratio of 0, would provide a guide for treating some patients.

Stripping and reprobing of 2D western blots to identify pTyr-RTKs is labor intensive. A set of reverse blots is required in every case to be sure of results. RTK signals from EGFR and PDGFR overlapped because of extensive glycosylation. An alternative approach that might work would be to multiplex 1D western blots—combine the pTyr antibody with a Cy dye labeled antibody against a single RTK-specific phosphorylation site. For example a rabbit anti-pTyr1068-EGFR antibody might be mixed with the mouse pTyr antibody during the overnight incubation. An anti-rabbit secondary antibody might be reacted and the blot scanned at the Cy dye wavelength, before normal ECL detection with an anti-mouse HRP secondary.

ECL sensitivity: Assuming that 1 ng (20 femtomoles) of pA has two pTyr/molecule on average, then 20 fmoles of tumor EGFR that has 6 pTyr/molecule on average, should give a signal that is 3 times darker and detectable, despite being spread out over a larger area because of glycosylation.

The pTyr signal in sample L3 and L5 was stable in individual tissue aliquots prepared in SDS buffer and stored at −80° C. for 3 years at which time it was used up. The half of each intact original excised lung sample that was stored frozen at −80° for 3 years, including active tumors L3, L4 and L5, lost virtually all pTyr signal over that time.

These may be obtained by directly scanning the ECL-treated membrane with a phosphoimager such as a GE Typhoon, or by exposing the membrane to x-ray film and then scanning that permanent record with a calibrated densitometer. In either case, a short exposure reveals the abundant pTyr-protein isoforms while longer exposures may reveal a more complex pattern including less abundant pTyr-protein species.

RTK glycosylation: One unexpected problem with 2D co-migration experiments was that extreme charge and size heterogeneity imparted by protein glycosylation made pattern matching difficult. Glycosylation of pTyr EGFR in tumors L3 and L5 appears to be more extensive than that seen in A431 cells. In general, glycan side chains are extraordinarily complex and difficult to study. Kaszuba et al state: " . . . glycosylation is immensely diverse, with different cell lines exhibiting distinct patterns of protein glycosylation, largely as a result of the expression of varying repertoires of glycosidases and glycosyltransferases . . . " Since, glycans are often quite immunogenic, immuno-targeting of oncogenic glycans in some way might be very specific, with few side effects.

PVDF staining with Coomassie blue is useful: When western blotting is used to detect single proteins in tissue lysates containing several thousand polypeptides, one concern is that abundant proteins might affect the pattern. Staining the PVDF membranes and scanning to record the pattern before immunostaining allows visualization of abundant proteins. The PVDF Coomassie image exactly aligns with the WB film pattern, and can be superimposed if needed via alignment of marked corners using software such as Adobe Elements. Nonspecific binding occasionally reveals the position of heavily loaded molecular weight markers run down the basic edge of the 2D gel as well as albumin and other high abundance proteins.

Considerable evidence exists that shows poor correlation between mRNA and protein expression, at best 41%. This poor correlation of 40% at best, holds true for six types of cultured mammalian cells and twelve human tissue samples and leads to the conclusion that mRNA levels cannot be used as a surrogate for protein levels. Measuring protein expression directly by mass spectrometry is hindered because important membrane proteins are insoluble in buffers that are compatible with MS, microarrays, and immobilized pH gradient strip 2D electrophoresis.

The power of the detergent sodium dodecyl sulfate (SDS) as a protein-dissolving agent is sometimes forgotten. SDS binds stoichiometrically to the peptide backbone in the ratio of 1.4 g SDS/g protein such that both secondary and tertiary structures are lost. When tissue homogenates are heated to boiling in the presence of SDS, virtually all protein species become solubilized, including membrane proteins such as receptor tyrosine kinases in human tumor tissues.

Two-dimensional gel electrophoresis (2DE) is a 2-step method where protein mixtures are first separated by charge using isoelectric focusing, then by size using SDS PAGE. This method was first developed in 1975 by Patrick O'Farrell who performed IEF in polyacrylamide tube gels polymerized with ampholines and a non-ionic detergent called IGEPAL. The protein mixture is loaded at the top of a tube gel, which is placed in a chamber with dilute acid in the bottom and dilute base in the top. Application of high voltage across the tubes cause the ampholines to migrate towards the acid where then become protonated and stop at their pI, the pH at which the molecule is electrically neutral. Proteins loaded at the top of the tube migrate more slowly into the newly formed pH gradient and also stop at their pI. The tube gels are extruded and sealed onto the stacking gel of an SDS PAGE slab gel where the second dimension of 2DE is completed.

There is a misconception that IEF is always incompatible with SDS buffer. In fact this is true for a popular variation of 2DE where IEF is performed with commercially available immobilized pH gradient strips. The Anderson team showed early on however, that IEF in tube gels is compatible with SDS. During the overnight period required for IEF to come to equilibration in tube gels, SDS is stripped off proteins to create micelles with NP-40, a non-ionic detergent. The charged micelles migrate to the acid end of the tube gel where they form a bulb that is discarded. This SDS compatibility was verified by our laboratory along with method robustness in 1989. Although it cannot be proven that all the SDS is stripped off every protein, the 2D patterns of samples dissolved in SDS buffer are quite reproducible. Furthermore, since samples for 1D and 2D SDS PAGE gels are dissolved in the same SDS buffer, the 2D pattern is useful for interpretation of 1D bands. Samples can be screened using 1D SDS PAGE western blotting using an anti-pTyr antibody. Those that show a positive signal can be further investigated using 2D SDS PAGE.

SDS compatibility is critical to the work described here because, to our knowledge, the intact high molecular weight receptor tyrosine kinases (200 kDa) can only be quantitatively solubilized using SDS buffer with heating to 100° C.

Methods for Example 2

Human Tissue Samples 14 human lung tumor and 11 control lung tissue samples were purchased in 2011 and 2014 from a biobank, ILS Bio, LLC (now BioreclamationIVT, Chesterfield, Md.) as shown in Table 1. Group 1 (2011) consisted of 5 SCC tumor samples, 1 ADC tumor sample, 1 SCC matched control, and 2 unmatched disease controls, asthmatic and tuberculosis lung received in 2011. Group 2 (2014) consisted of 7 SCC tumor samples and 1 ACD tumor sample along with a 8 matched normal adjacent tissue (NAT) controls. The resected tissue samples were shipped on dry ice and stored at −80° C. until preparation.

All tissue sample preparation was performed on ice with ice-cold reagents. Samples were cut in half with a scalpel; one half was frozen on dry ice prior to long-term storage at −80° C. The other half was rinsed with Tris buffered saline (TBS, 50 mM Tris, 150 mM NaCl pH 7.4), then placed in a motorized glass-teflon homogenizer containing: 2 ml Osmotic Lysis Buffer (10 mM Tris, pH 7.4 and 0.3% SDS); 1% protease inhibitors from a stock containing 20 mM AEBSF, 1 mg/mL Leupeptin, 0.36 mg/mL E-64, 5.6 mg/mL Benzamidine and 500 mM EDTA; phosphatase inhibitor cocktails Sets I and II (serine/threonine and tyrosine); nucleases (50 µg/mL RNase, 100 µg/mL DNase in 5 mM $MgCl_2$ and 10 mM Tris-CI pH 7), and 3 mL SDS buffer (5% SDS, 10% glycerol, 60 mM Tris, pH 6.8). SDS was from IBI Scientific (Peosta, Iowa); unless specified remaining reagents were from Millipore Sigma (Burlington, Mass.). The tumor tissue was homogenized and then placed in a boiling water bath for 5 min. A protein determination was performed using the BCA method. Finally the sample was diluted with SDS buffer containing 5% beta-mercaptoethanol, aliquoted, and stored at −80° C.

1D SDS PAGE

Polyacrylamide slab gels (10% acrylamide, 13×15 cm×1.0 mm thick) were prepared with 30% acrylamide stock with 0.8% Bis crosslinker, both from National Diagnostics (Atlanta, Ga.). Ammonium persulfate (Mallinckrodt, St Louis, Mo.) and TEMED (Bio-Rad, Hercules, Calif.) were used as catalysts. After at least 1 hour of polymerization, a 2.5×15 cm stacker gel was added with a 15-well comb to provide wells for loading samples. SDS slab gel electrophoresis was carried out according to the method of Laemmli as modified by Burgess-Cassler (second dimension) (Burgess-Cassler, A., Johansen, J. J., Santek, D. A., Ide, J. R., and Kendrick, N. C. (1989) Computerized quantitative analysis of coomassie-blue-stained serum proteins separated by two-dimensional electrophoresis, *Clin Chem* 35, 2297-2304) for about 4 hrs at 15 mA/gel. The following proteins (Millipore Sigma) were run in one lane as molecular weight standards: myosin (220,000), phosphorylase A (94,000), catalase (60,000), actin (43,000), carbonic anhydrase (29,000), and lysozyme (14,000). The MW markers were loaded at 1 µg each except for lysozyme which was used at 2 µg/lane.

2D SDS PAGE

Two dimensional SDS PAGE was performed according to the method of O'Farrell (22) as modified by Burgess-Cassler et. al. Isoelectric focusing tube gels (130 mm long×2.3 mm internal diameter) sealed at the bottom with parafilm, were prepared with: acrylamide stock (1.5% piperazine diacrylamide (Sigma) in 30% acrylamide stock), ultrapure urea (MP Biomedicals (Solon, Ohio)); 10% IGEPAL Sigma-Aldrich, and 2% ampholines (pH 3-10 Iso-Dalt or a 1:1 mixture of Servalyte pH 4-6 and pH 5-8 ampholines, Serva Electrophoresis, Heidelberg, Germany).

Samples were dissolved in SDS buffer with heating before being loaded at the basic end of an acrylamide tube gel polymerized with 2% ampholines. The ampholines stack to form a pH gradient when 1000 volts are applied for 20 hrs. During this time, SDS is stripped off the proteins by the nonionic IGEPAL detergent, and proteins separate according to their isoelectric point (pI) along the pH gradient. The SDS-IGEPAL micelles migrate to the extreme acid end of the tube gel where they form a bulb that is cut off and discarded.

The tube gels are extruded by air pressure into containing SDS buffer and then equilibrated for 10 min in buffer "0" (10% glycerol, 50 mM dithiothreitol, 2.3% SDS and 0.0625 M tris, pH 6.8). Each tube gel was sealed to the top of a stacking gel overlaying a 10% acrylamide slab gel (1.0 mm thick). SDS slab gel electrophoresis was carried out for about 5 hrs at 25 mA/gel. Protein standards (described in 1D SDS PAGE section) appear as bands on the basic edge of the Coomassie stained slab gels or PVDF blots. Stained gels and blots were dried between sheets of cellophane paper with the acid edge to the left.

One μg of an IEF internal standard, tropomyosin, is added to every sample scheduled for western blotting for purposes of quality control. This protein migrates as a doublet with lower polypeptide spot of MW 33,000 and pI 5.2; an arrow on the stained gel images marks its position. Tube gel pH gradient plots, obtained with a surface pH electrode from blank tubes extruded after IEF, are determined for each set of ampholines.

Transblotting

After slab gel electrophoresis, the gels were placed in transfer buffer (10 mM Caps, pH 11.0, 10% methanol) and transblotted onto PVDF membranes overnight at 200 mA, 4° C. and approximately 100 volts/two gels in a model EBU-100 apparatus from CBS Scientific (Del Mar, Calif.). Transblotted PVDF membranes were stained with Coomassie blue (Millipore Sigma) in a solution containing 50% methanol, 0.12% Coomassie blue dye. The blots were incubated with dye solution for 5 min on an orbital shaker, then destained in a solution of 50% methanol by shaking for 1.5 min. Blots were rinsed twice for 1 min in ultrapure water and placed on a filter paper sheet to air dry. A desktop scanner was used to obtain images of dried Coomassie-stained PVDF membranes. For storage, blots covered with another filter paper sheet and placed between poster board supports for storage. Coomassie staining does not interfere with subsequent western blotting.

TABLE 20

Antibodies used for western blotting. The secondary antibody dilution (1:2000) with a 2 hour incubation time.
Western Blotting (Immunostaining):

| Primary Antibody | Supplier/ Catalog # | Source | Dilution | Secondary Antibody | Supplier/ Catalog # |
|---|---|---|---|---|---|
| Phospho-tyrosine (clone PY20) | ExAlpha/ X1021 | Mouse | 1:1000, 1:5000* | Anti-mouse IgG HRP from sheep | GE Healthcare/ NA931V |
| EGFR | Cell Signaling/ 4267S | Rabbit | 1:1000 | Anti-rabbit IgG HRP from sheep | GE Healthcare/ NA934V |
| PDGFR beta | Cell Signaling/ 4564S | Rabbit | 1:10,000* | Anti-rabbit IgG HRP from sheep | GE Healthcare/ NA934V |
| VEGFR 2 | Cell Signaling/ 4564S | Rabbit | 1:10,000* | Anti-rabbit IgG HRP from sheep | GE Healthcare/ NA934V |
| MET (L41G3) | Cell Signaling/ 3148S | Mouse | 1:1000 | Anti-mouse IgG HRP from sheep | GE Healthcare/ NA931V |
| ALK (31F12) | Cell Signaling/ 3791S | Mouse | 1:1000 | Anti-rabbit IgG HRP from sheep | GE Healthcare/ NA934V |

Stained PVDF membranes were wet in 100% methanol to remove the stain, rinsed briefly in tween-20 TBS (TTBS), and blocked for two hours in 5% non fat dry milk (NFDM) diluted in TTBS. The blots were then incubated overnight on an orbital shaker at room temperature with primary antibody (Table 20) in 2% NFDM TTBS. The blot was rinsed 3×10 minutes in TTBS and shaken with secondary antibody diluted 1:2000 for 2 hours. Finally, the blots were treated with Pierce ECL reagent (Thermo), and exposed to x-ray film (Hyperfilm ECL [GE Amersham] or Kodak BioMax [Thermo-Fisher]), followed by film development with an automatic Konica Minolta Medical Film Processor SRX-101A. The linear range of the X-ray film was determined with a laser densitometer calibrated for linearity with NIST-tied Melles Griot optical density filters over the range 1-3 OD units.

pA phosphotyrosine standard A 48 kD recombinant protein kinase fragment containing the C-terminal active tail of ALK was purchased from ProQinase, GmbH. (Freiburg, Germany). This recombinant human active protein kinase ALK (HIS-tag, product No 1048-0000-1) contains internal fragment amino acids L1066-S1437 (NM_004304.3). Two different lots of the pA standard were generated by an in vitro phosphorylation reaction followed by an alkylation reaction. For the phosphorylation reaction the recombinant ALK was combined 1:1 with kinase activation buffer (50 mM HEPES pH 7.5, 100 mM NaCl (Fisher), 2 mM DTT (Fisher), 7.5 mM MgCl, 7.5 mM $MnCl_2$, and 2 mM ATP. The phosphorylated ALK is referred to as pTyr-ALK48. Unless specified, all reagents were purchased from Sigma. Tyrosine phosphorylation was confirmed by western blot (FIG. 9). After kinase reaction, cysteine sulfhydral groups were chemically blocked by alkylation with iodoacetamide (Thermo Fisher Scientific). (NK, GP's book p46-47 and GP p51-52). The sample was pretreated with 25 mM TCEP-HCl in 0.1% SDS, and 90 mM $NH_4HCO_3$ for 1 hour at 55° C., and then reacted with iodoacetamide for 30 minutes at 55° C. protected from light. The reaction was stopped by addition of SDS Buffer (10% glycerol, 5% beta mecaptoethanol, 5% SDS, 62.5 mM Tris pH 6.8). The phosphorylated, iodoacetylated ALK standard is referred to as pTyr-ALK48-SB (pA).

Western blot phosphotyrosine positive control (pE) is an EGF stimulated A431 whole cell lysate (Exalpha Biologicals, Shirley, Mass.). Two different lots (#10852 and 13639), were purchased and prepared by heated in a boiling water bath for 5 minutes before loading.

Mass Spectrometry of pA

Protein digestion and peptide extraction. Proteins that were separated by SDS-PAGE/2D-PAGE and stained by Coomassie dye were excised, washed and the proteins from the gel were treated according to published protocols (Shevchenko, Wilm et al. 1996; Darie, Deinhardt et al. 2011; Sokolowska, Woods et al. 2012). Briefly, the gel pieces were washed in high purity, high performance liquid chromatography HPLC grade water, dehydrated and cut into small pieces and destained by incubating in 50 mM ammonium bicarbonate, 50 mM ammonium bicarbonate/50% acetonitrile, and 100% acetonitrile under moderate shaking, followed by drying in a speed-vac concentrator. The gel bands were then rehydrated with 50 mM ammonium bicarbonate. The gel pieces were then re-incubated in 50 mM ammonium bicarbonate/50% acetonitrile, and 100% acetonitrile under moderate shaking, followed by drying in speed-vac concentrator. The dry gel pieces were then rehydrated using 50 mM ammonium bicarbonate containing 10 ng/μL trypsin and incubated overnight at 37° C. under low shaking. The resulting peptides were extracted twice with 5% formic acid/50 mM ammonium bicarbonate/50% acetonitrile and once with 100% acetonitrile under moderate shaking. Peptide mixture was then dried in a speed-vac, solubilized in 20 µL of 0.1% formic acid/2% acetonitrile, cleaned using a C18 ZipTip (Millipore) and then dried again. The clean peptide mixture was then solubilized in 20 µL of 0.1% formic acid/2% acetonitrile.

NanoLC-MS/MS. The peptides mixture was analyzed by reversed phase nanoliquid chromatography (LC) and MS (LC-MS/MS) using a NanoAcuity UPLC (Micromass/Waters, Milford, Mass.) coupled to a Q-TOF Xevo G2 mass spectrometer (Micromass/Waters, Milford, Mass.), according to published procedures (Darie, Deinhardt et al. 2011; Sokolowska, Dorobantu et al. 2012; Sokolowska, Gawinowicz et al. 2012). Briefly, the peptides were loaded onto a 100 µm×10 mm NanoAquity BEH130 C18 1.7 µm UPLC column (Waters, Milford, Mass.) and eluted over a 60 minute gradient of 2-80% organic solvent (ACN containing 0.1% FA) at a flow rate of 400 nL/min. The aqueous solvent was 0.1% FA in HPLC water. The column was coupled to a Picotip Emitter Silicatip nano-electrospray needle (New Objective, Woburn, Mass.). MS data acquisition involved survey MS scans and automatic data dependent analysis (DDA) of the top six ions with the highest intensity ions with the charge of 2+, 3+ or 4+ ions. The MS/MS was triggered when the MS signal intensity exceeded 250 counts/second. In survey MS scans, the three most intense peaks were selected for collision-induced dissociation (CID) and fragmented until the total MS/MS ion counts reached 10,000 or for up to 6 seconds each. The entire procedure used was previously described (Darie, Deinhardt et al. 2011; Sokolowska, Dorobantu et al. 2012; Sokolowska, Gawinowicz et al. 2012). Calibration was performed for both precursor and product ions using 1 pmol GluFib (Glu1-Fibrinopeptide B) standard peptide with the sequence EGVNDNEEGFFSAR and the monoisotopic doubly-charged peak with m/z of 785.84.

Data processing and protein identification. The raw data were processed using ProteinLynx Global Server (PLGS, version 2.4) software. The following parameters were used: background subtraction of polynomial order 5 adaptive with a threshold of 30%, two smoothings with a window of three channels in Savitzky-Golay mode and centroid calculation of top 80% of peaks based on a minimum peak width of 4 channels at half height. The resulting pkl files were submitted for database search and protein identification to the in-house Mascot server (www.matrixscience.com, Matrix Science, London, UK) for database search using the following parameters: databases from NCBI (Human), parent mass error of 0.5 Da with 1 13C, product ion error of 0.8 Da, enzyme used: trypsin, three missed cleavages, carbamydomethyl and propionamide as cysteine variable modification and Methionine oxidized as variable modification. To identify the false negative results, we used additional parameters such as different databases or organisms, a narrower error window for the parent mass error (1.2 and then 0.2 Da) and for the product ion error (0.6 Da), and up to two missed cleavage sites for trypsin. In addition, the pkl files were also searched against in-house PLGS database version 2.4 (www.waters.com) using searching parameters similar to the ones used for Mascot search. The Mascot and PLGS database search provided a list of proteins for each gel band. To eliminate false positive results, for the proteins identified by either one peptide or a mascot score lower than 25, we verified the MS/MS spectra that led to identification of a protein. Protein phosphorylation was identified by using directly Mascot and ProteinLynx Global Server databases and the searches were done using phosphorylations of the tyrosine, serine and threonine as variable modifications. MSMS spectra of the phosphopeptides identified in the database search were also verified manually.

We claim:

1. A protein standard comprising two components,
   the first component comprising a phosphorylated Anaplastic Lymphoma Kinase-sulfhydryl-blocked (pALK48-SB) protein,
   wherein the protein standard contains 0.1-2.0 ng of the pALK48-SB protein, and
   the second component comprising at least a second protein, the second protein comprising a phosphorylated amino acid, and
   wherein the protein standard has a ratio of 0.5-2.0 of the second protein of the second component relative to the pALK48-SB protein of the first component.

2. The protein standard of claim 1, wherein the pALK48-SB protein comprises SEQ ID NO: 1.

3. The protein standard of claim 2, wherein the pALK48-SB protein comprises SEQ ID NO: 2.

4. The protein standard of claim 2, wherein the pALK48-SB protein comprises a phosphorylated tyrosine residue at position 31 of SEQ ID NO: 1, at position 218 of SEQ ID NO: 1, or both.

5. The protein standard of claim 3, wherein the pALK48-SB protein comprises a phosphorylated tyrosine residue at position 69 of SEQ ID NO: 2, at position 256 of SEQ ID NO: 2, or both.

6. The protein standard of claim 2, wherein the pALK48-SB protein comprises 2-11 cysteine residues with a blocked sulfhydryl group.

7. The protein standard of claim 1, wherein the sulfhydryl blocked group comprises an alkylated sulfhydryl group.

8. The protein standard of claim 1, further comprising a buffer.

9. A kit comprising the protein standard of claim 1.

10. The protein standard of claim 8, wherein the buffer is selected from the group comprising phosphate-buffered saline buffer, TRIS buffer, HEPES buffer, MOPS buffer, sodium dodecyl sulphate (SD S) buffer, or beta-mercaptoethanol.

11. The protein standard of claim 1, wherein the phosphorylated protein of the second component comprises HER1, HER2, HER3, HER4, PDFGR, MET, FGFT, ALK, or VEGFR proteins.

\* \* \* \* \*

SEQUENCE LISTING

```
<160> NUMBER OF SEQ ID NOS: 4

<210> SEQ ID NO 1
<211> LENGTH: 372
<212> TYPE: PRT
<213> ORGANISM: Homo sapiens
<220> FEATURE:
<221> NAME/KEY: misc_feature
<223> OTHER INFORMATION: Human ALK protein fragment L1066-S1437 from
      ProQinase

<400> SEQUENCE: 1

Leu Gln Ala Met Gln Met Glu Leu Gln Ser Pro Glu Tyr Lys Leu Ser
1               5                   10                  15

Lys Leu Arg Thr Ser Thr Ile Met Thr Asp Tyr Asn Pro Asn Tyr Cys
            20                  25                  30

Phe Ala Gly Lys Thr Ser Ser Ile Ser Asp Leu Lys Glu Val Pro Arg
        35                  40                  45

Lys Asn Ile Thr Leu Ile Arg Gly Leu Gly His Gly Ala Phe Gly Glu
    50                  55                  60

Val Tyr Glu Gly Gln Val Ser Gly Met Pro Asn Asp Pro Ser Pro Leu
65                  70                  75                  80

Gln Val Ala Val Lys Thr Leu Pro Glu Val Cys Ser Glu Gln Asp Glu
                85                  90                  95

Leu Asp Phe Leu Met Glu Ala Leu Ile Ile Ser Lys Phe Asn His Gln
```

```
            100                 105                 110
Asn Ile Val Arg Cys Ile Gly Val Ser Leu Gln Ser Leu Pro Arg Phe
        115                 120                 125
Ile Leu Leu Glu Leu Met Ala Gly Gly Asp Leu Lys Ser Phe Leu Arg
130                 135                 140
Glu Thr Arg Pro Arg Pro Ser Gln Pro Ser Ser Leu Ala Met Leu Asp
145                 150                 155                 160
Leu Leu His Val Ala Arg Asp Ile Ala Cys Gly Cys Gln Tyr Leu Glu
                165                 170                 175
Glu Asn His Phe Ile His Arg Asp Ile Ala Ala Arg Asn Cys Leu Leu
            180                 185                 190
Thr Cys Pro Gly Pro Gly Arg Val Ala Lys Ile Gly Asp Phe Gly Met
        195                 200                 205
Ala Arg Asp Ile Tyr Arg Ala Ser Tyr Tyr Arg Lys Gly Gly Cys Ala
    210                 215                 220
Met Leu Pro Val Lys Trp Met Pro Pro Glu Ala Phe Met Glu Gly Ile
225                 230                 235                 240
Phe Thr Ser Lys Thr Asp Thr Trp Ser Phe Gly Val Leu Leu Trp Glu
                245                 250                 255
Ile Phe Ser Leu Gly Tyr Met Pro Tyr Pro Ser Lys Ser Asn Gln Glu
            260                 265                 270
Val Leu Glu Phe Val Thr Ser Gly Gly Arg Met Asp Pro Pro Lys Asn
        275                 280                 285
Cys Pro Gly Pro Val Tyr Arg Ile Met Thr Gln Cys Trp Gln His Gln
    290                 295                 300
Pro Glu Asp Arg Pro Asn Phe Ala Ile Ile Leu Glu Arg Ile Glu Tyr
305                 310                 315                 320
Cys Thr Gln Asp Pro Asp Val Ile Asn Thr Ala Leu Pro Ile Glu Tyr
                325                 330                 335
Gly Pro Leu Val Glu Glu Glu Lys Val Pro Val Arg Pro Lys Asp
            340                 345                 350
Pro Glu Gly Val Pro Pro Leu Leu Val Ser Gln Gln Ala Lys Arg Glu
        355                 360                 365
Glu Glu Arg Ser
    370

<210> SEQ ID NO 2
<211> LENGTH: 422
<212> TYPE: PRT
<213> ORGANISM: Homo sapiens
<220> FEATURE:
<221> NAME/KEY: misc_feature
<223> OTHER INFORMATION: Tagged version of human ALK protein fragment

<400> SEQUENCE: 2

Met Asp Tyr Lys Asp Asp Asp Lys Asp Tyr Lys Asp Asp Asp
1               5                   10                  15
Lys Asp Tyr Lys Asp Asp Asp Lys Asp Tyr Lys Asp Asp Asp
                20                  25                  30
Lys Ser Gly Gly Gly Ser Leu Gln Ala Met Gln Met Glu Leu Gln Ser
            35                  40                  45
Pro Glu Tyr Lys Leu Ser Lys Leu Arg Thr Ser Thr Ile Met Thr Asp
        50                  55                  60
Tyr Asn Pro Asn Tyr Cys Phe Ala Gly Lys Thr Ser Ser Ile Ser Asp
65                  70                  75                  80
```

```
Leu Lys Glu Val Pro Arg Lys Asn Ile Thr Leu Ile Arg Gly Leu Gly
                85                  90                  95

His Gly Ala Phe Gly Glu Val Tyr Glu Gly Gln Val Ser Gly Met Pro
            100                 105                 110

Asn Asp Pro Ser Pro Leu Gln Val Ala Val Lys Thr Leu Pro Glu Val
        115                 120                 125

Cys Ser Glu Gln Asp Glu Leu Asp Phe Leu Met Glu Ala Leu Ile Ile
    130                 135                 140

Ser Lys Phe Asn His Gln Asn Ile Val Arg Cys Ile Gly Val Ser Leu
145                 150                 155                 160

Gln Ser Leu Pro Arg Phe Ile Leu Leu Glu Leu Met Ala Gly Gly Asp
                165                 170                 175

Leu Lys Ser Phe Leu Arg Glu Thr Arg Pro Arg Pro Ser Gln Pro Ser
            180                 185                 190

Ser Leu Ala Met Leu Asp Leu Leu His Val Ala Arg Asp Ile Ala Cys
        195                 200                 205

Gly Cys Gln Tyr Leu Glu Glu Asn His Phe Ile His Arg Asp Ile Ala
    210                 215                 220

Ala Arg Asn Cys Leu Leu Thr Cys Pro Gly Pro Gly Arg Val Ala Lys
225                 230                 235                 240

Ile Gly Asp Phe Gly Met Ala Arg Asp Ile Tyr Arg Ala Ser Tyr Tyr
                245                 250                 255

Arg Lys Gly Gly Cys Ala Met Leu Pro Val Lys Trp Met Pro Pro Glu
            260                 265                 270

Ala Phe Met Glu Gly Ile Phe Thr Ser Lys Thr Asp Thr Trp Ser Phe
        275                 280                 285

Gly Val Leu Leu Trp Glu Ile Phe Ser Leu Gly Tyr Met Pro Tyr Pro
    290                 295                 300

Ser Lys Ser Asn Gln Glu Val Leu Glu Phe Val Thr Ser Gly Gly Arg
305                 310                 315                 320

Met Asp Pro Pro Lys Asn Cys Pro Gly Pro Val Tyr Arg Ile Met Thr
                325                 330                 335

Gln Cys Trp Gln His Gln Pro Glu Asp Arg Pro Asn Phe Ala Ile Ile
            340                 345                 350

Leu Glu Arg Ile Glu Tyr Cys Thr Gln Asp Pro Asp Val Ile Asn Thr
        355                 360                 365

Ala Leu Pro Ile Glu Tyr Gly Pro Leu Val Glu Glu Glu Lys Val
    370                 375                 380

Pro Val Arg Pro Lys Asp Pro Glu Gly Val Pro Pro Leu Leu Val Ser
385                 390                 395                 400

Gln Gln Ala Lys Arg Glu Glu Glu Arg Ser Lys Leu Leu Glu His His
                405                 410                 415

His His His His
        420

<210> SEQ ID NO 3
<211> LENGTH: 1620
<212> TYPE: PRT
<213> ORGANISM: Homo sapiens
<220> FEATURE:
<221> NAME/KEY: misc_feature
<223> OTHER INFORMATION: Homo sapiens anaplastic lymphoma receptor
      tyrosine kinase (ALK)

<400> SEQUENCE: 3

Met Gly Ala Ile Gly Leu Leu Trp Leu Leu Pro Leu Leu Leu Ser Thr
```

-continued

```
1               5                   10                  15
Ala Ala Val Gly Ser Gly Met Gly Thr Gly Gln Arg Ala Gly Ser Pro
            20                  25                  30
Ala Ala Gly Pro Pro Leu Gln Pro Arg Glu Pro Leu Ser Tyr Ser Arg
            35                  40                  45
Leu Gln Arg Lys Ser Leu Ala Val Asp Phe Val Pro Ser Leu Phe
    50                  55                  60
Arg Val Tyr Ala Arg Asp Leu Leu Pro Pro Ser Ser Ser Glu Leu
65                  70                  75                  80
Lys Ala Gly Arg Pro Glu Ala Arg Gly Ser Leu Ala Leu Asp Cys Ala
                85                  90                  95
Pro Leu Leu Arg Leu Leu Gly Pro Ala Pro Gly Val Ser Trp Thr Ala
                100                 105                 110
Gly Ser Pro Ala Pro Ala Glu Ala Arg Thr Leu Ser Arg Val Leu Lys
                115                 120                 125
Gly Gly Ser Val Arg Lys Leu Arg Arg Ala Lys Gln Leu Val Leu Glu
            130                 135                 140
Leu Gly Glu Glu Ala Ile Leu Glu Gly Cys Val Gly Pro Pro Gly Glu
145                 150                 155                 160
Ala Ala Val Gly Leu Leu Gln Phe Asn Leu Ser Glu Leu Phe Ser Trp
                165                 170                 175
Trp Ile Arg Gln Gly Glu Gly Arg Leu Arg Ile Arg Leu Met Pro Glu
            180                 185                 190
Lys Lys Ala Ser Glu Val Gly Arg Glu Gly Arg Leu Ser Ala Ala Ile
            195                 200                 205
Arg Ala Ser Gln Pro Arg Leu Leu Phe Gln Ile Phe Gly Thr Gly His
        210                 215                 220
Ser Ser Leu Glu Ser Pro Thr Asn Met Pro Ser Pro Ser Pro Asp Tyr
225                 230                 235                 240
Phe Thr Trp Asn Leu Thr Trp Ile Met Lys Asp Ser Phe Pro Phe Leu
                245                 250                 255
Ser His Arg Ser Arg Tyr Gly Leu Glu Cys Ser Phe Asp Phe Pro Cys
            260                 265                 270
Glu Leu Glu Tyr Ser Pro Pro Leu His Asp Leu Arg Asn Gln Ser Trp
            275                 280                 285
Ser Trp Arg Arg Ile Pro Ser Glu Glu Ala Ser Gln Met Asp Leu Leu
        290                 295                 300
Asp Gly Pro Gly Ala Glu Arg Ser Lys Glu Met Pro Arg Gly Ser Phe
305                 310                 315                 320
Leu Leu Leu Asn Thr Ser Ala Asp Ser Lys His Thr Ile Leu Ser Pro
                325                 330                 335
Trp Met Arg Ser Ser Glu His Cys Thr Leu Ala Val Ser Val His
                340                 345                 350
Arg His Leu Gln Pro Ser Gly Arg Tyr Ile Ala Gln Leu Leu Pro His
            355                 360                 365
Asn Glu Ala Ala Arg Glu Ile Leu Leu Met Pro Thr Pro Gly Lys His
        370                 375                 380
Gly Trp Thr Val Leu Gln Gly Arg Ile Gly Arg Pro Asp Asn Pro Phe
385                 390                 395                 400
Arg Val Ala Leu Glu Tyr Ile Ser Ser Gly Asn Arg Ser Leu Ser Ala
                405                 410                 415
Val Asp Phe Phe Ala Leu Lys Asn Cys Ser Glu Gly Thr Ser Pro Gly
                420                 425                 430
```

-continued

Ser Lys Met Ala Leu Gln Ser Phe Thr Cys Trp Asn Gly Thr Val
    435                 440                 445

Leu Gln Leu Gly Gln Ala Cys Asp Phe His Gln Asp Cys Ala Gln Gly
450                 455                 460

Glu Asp Glu Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
                485                 490                 495

His Thr Pro Gln Trp Gln Val Arg Thr Leu Lys Asp Ala Arg Phe Gln
            500                 505                 510

Asp His Gln Asp His Ala Leu Leu Ser Thr Thr Asp Val Pro Ala
            515                 520                 525

Ser Glu Ser Ala Thr Val Thr Ser Ala Thr Phe Pro Ala Pro Ile Lys
530                 535                 540

Ser Ser Pro Cys Glu Leu Arg Met Ser Trp Leu Ile Arg Gly Val Leu
545                 550                 555                 560

Arg Gly Asn Val Ser Leu Val Leu Val Glu Asn Lys Thr Gly Lys Glu
                565                 570                 575

Gln Gly Arg Met Val Trp His Val Ala Ala Tyr Glu Gly Leu Ser Leu
            580                 585                 590

Trp Gln Trp Met Val Leu Pro Leu Leu Asp Val Ser Asp Arg Phe Trp
        595                 600                 605

Leu Gln Met Val Ala Trp Trp Gly Gln Gly Ser Arg Ala Ile Val Ala
        610                 615                 620

Phe Asp Asn Ile Ser Ile Ser Leu Asp Cys Tyr Leu Thr Ile Ser Gly
625                 630                 635                 640

Glu Asp Lys Ile Leu Gln Asn Thr Ala Pro Lys Ser Arg Asn Leu Phe
                645                 650                 655

Glu Arg Asn Pro Asn Lys Glu Leu Lys Pro Gly Glu Asn Ser Pro Arg
            660                 665                 670

Gln Thr Pro Ile Phe Asp Pro Thr Val His Trp Leu Phe Thr Thr Cys
        675                 680                 685

Gly Ala Ser Gly Pro His Gly Pro Thr Gln Ala Gln Cys Asn Asn Ala
        690                 695                 700

Tyr Gln Asn Ser Asn Leu Ser Val Glu Val Gly Ser Glu Gly Pro Leu
705                 710                 715                 720

Lys Gly Ile Gln Ile Trp Lys Val Pro Ala Thr Asp Thr Tyr Ser Ile
                725                 730                 735

Ser Gly Tyr Gly Ala Ala Gly Gly Lys Gly Gly Lys Asn Thr Met Met
            740                 745                 750

Arg Ser His Gly Val Ser Val Leu Gly Ile Phe Asn Leu Glu Lys Asp
        755                 760                 765

Asp Met Leu Tyr Ile Leu Val Gly Gln Gln Gly Glu Asp Ala Cys Pro
        770                 775                 780

Ser Thr Asn Gln Leu Ile Gln Lys Val Cys Ile Gly Glu Asn Asn Val
785                 790                 795                 800

Ile Glu Glu Glu Ile Arg Val Asn Arg Ser Val His Glu Trp Ala Gly
                805                 810                 815

Gly Gly Gly Gly Gly Gly Gly Ala Thr Tyr Val Phe Lys Met Lys Asp
            820                 825                 830

Gly Val Pro Val Pro Leu Ile Ile Ala Ala Gly Gly Gly Gly Arg Ala
        835                 840                 845

-continued

Tyr Gly Ala Lys Thr Asp Thr Phe His Pro Glu Arg Leu Glu Asn Asn
        850             855             860

Ser Ser Val Leu Gly Leu Asn Gly Asn Ser Gly Ala Ala Gly Gly Gly
865             870             875             880

Gly Gly Trp Asn Asp Asn Thr Ser Leu Leu Trp Ala Gly Lys Ser Leu
            885             890             895

Gln Glu Gly Ala Thr Gly Gly His Ser Cys Pro Gln Ala Met Lys Lys
            900             905             910

Trp Gly Trp Glu Thr Arg Gly Gly Phe Gly Gly Gly Gly Gly Gly Cys
            915             920             925

Ser Ser Gly Gly Gly Gly Gly Gly Tyr Ile Gly Gly Asn Ala Ala Ser
930             935             940

Asn Asn Asp Pro Glu Met Asp Gly Glu Asp Gly Val Ser Phe Ile Ser
945             950             955             960

Pro Leu Gly Ile Leu Tyr Thr Pro Ala Leu Lys Val Met Glu Gly His
            965             970             975

Gly Glu Val Asn Ile Lys His Tyr Leu Asn Cys Ser His Cys Glu Val
            980             985             990

Asp Glu Cys His Met Asp Pro Glu Ser His Lys Val Ile Cys Phe Cys
            995             1000            1005

Asp His Gly Thr Val Leu Ala Glu Asp Gly Val Ser Cys Ile Val
    1010            1015            1020

Ser Pro Thr Pro Glu Pro His Leu Pro Leu Ser Leu Ile Leu Ser
    1025            1030            1035

Val Val Thr Ser Ala Leu Val Ala Ala Leu Val Leu Ala Phe Ser
    1040            1045            1050

Gly Ile Met Ile Val Tyr Arg Arg Lys His Gln Glu Leu Gln Ala
    1055            1060            1065

Met Gln Met Glu Leu Gln Ser Pro Glu Tyr Lys Leu Ser Lys Leu
    1070            1075            1080

Arg Thr Ser Thr Ile Met Thr Asp Tyr Asn Pro Asn Tyr Cys Phe
    1085            1090            1095

Ala Gly Lys Thr Ser Ser Ile Ser Asp Leu Lys Glu Val Pro Arg
    1100            1105            1110

Lys Asn Ile Thr Leu Ile Arg Gly Leu Gly His Gly Ala Phe Gly
    1115            1120            1125

Glu Val Tyr Glu Gly Gln Val Ser Gly Met Pro Asn Asp Pro Ser
    1130            1135            1140

Pro Leu Gln Val Ala Val Lys Thr Leu Pro Glu Val Cys Ser Glu
    1145            1150            1155

Gln Asp Glu Leu Asp Phe Leu Met Glu Ala Leu Ile Ile Ser Lys
    1160            1165            1170

Phe Asn His Gln Asn Ile Val Arg Cys Ile Gly Val Ser Leu Gln
    1175            1180            1185

Ser Leu Pro Arg Phe Ile Leu Leu Glu Leu Met Ala Gly Gly Asp
    1190            1195            1200

Leu Lys Ser Phe Leu Arg Glu Thr Arg Pro Arg Pro Ser Gln Pro
    1205            1210            1215

Ser Ser Leu Ala Met Leu Asp Leu Leu His Val Ala Arg Asp Ile
    1220            1225            1230

Ala Cys Gly Cys Gln Tyr Leu Glu Glu Asn His Phe Ile His Arg
    1235            1240            1245

Asp Ile Ala Ala Arg Asn Cys Leu Leu Thr Cys Pro Gly Pro Gly

```
          1250                1255                1260
Arg Val Ala Lys Ile Gly Asp Phe Gly Met Ala Arg Asp Ile Tyr
  1265                1270                1275
Arg Ala Ser Tyr Tyr Arg Lys Gly Gly Cys Ala Met Leu Pro Val
  1280                1285                1290
Lys Trp Met Pro Pro Glu Ala Phe Met Glu Gly Ile Phe Thr Ser
  1295                1300                1305
Lys Thr Asp Thr Trp Ser Phe Gly Val Leu Leu Trp Glu Ile Phe
  1310                1315                1320
Ser Leu Gly Tyr Met Pro Tyr Pro Ser Lys Ser Asn Gln Glu Val
  1325                1330                1335
Leu Glu Phe Val Thr Ser Gly Gly Arg Met Asp Pro Pro Lys Asn
  1340                1345                1350
Cys Pro Gly Pro Val Tyr Arg Ile Met Thr Gln Cys Trp Gln His
  1355                1360                1365
Gln Pro Glu Asp Arg Pro Asn Phe Ala Ile Ile Leu Glu Arg Ile
  1370                1375                1380
Glu Tyr Cys Thr Gln Asp Pro Asp Val Ile Asn Thr Ala Leu Pro
  1385                1390                1395
Ile Glu Tyr Gly Pro Leu Val Glu Glu Glu Glu Lys Val Pro Val
  1400                1405                1410
Arg Pro Lys Asp Pro Glu Gly Val Pro Pro Leu Leu Val Ser Gln
  1415                1420                1425
Gln Ala Lys Arg Glu Glu Glu Arg Ser Pro Ala Ala Pro Pro Pro
  1430                1435                1440
Leu Pro Thr Thr Ser Ser Gly Lys Ala Ala Lys Lys Pro Thr Ala
  1445                1450                1455
Ala Glu Ile Ser Val Arg Val Pro Arg Gly Pro Ala Val Glu Gly
  1460                1465                1470
Gly His Val Asn Met Ala Phe Ser Gln Ser Asn Pro Pro Ser Glu
  1475                1480                1485
Leu His Lys Val His Gly Ser Arg Asn Lys Pro Thr Ser Leu Trp
  1490                1495                1500
Asn Pro Thr Tyr Gly Ser Trp Phe Thr Glu Lys Pro Thr Lys Lys
  1505                1510                1515
Asn Asn Pro Ile Ala Lys Lys Glu Pro His Asp Arg Gly Asn Leu
  1520                1525                1530
Gly Leu Glu Gly Ser Cys Thr Val Pro Pro Asn Val Ala Thr Gly
  1535                1540                1545
Arg Leu Pro Gly Ala Ser Leu Leu Leu Glu Pro Ser Ser Leu Thr
  1550                1555                1560
Ala Asn Met Lys Glu Val Pro Leu Phe Arg Leu Arg His Phe Pro
  1565                1570                1575
Cys Gly Asn Val Asn Tyr Gly Tyr Gln Gln Gln Gly Leu Pro Leu
  1580                1585                1590
Glu Ala Ala Thr Ala Pro Gly Ala Gly His Tyr Glu Asp Thr Ile
  1595                1600                1605
Leu Lys Ser Lys Asn Ser Met Asn Gln Pro Gly Pro
  1610                1615                1620

<210> SEQ ID NO 4
<211> LENGTH: 6222
<212> TYPE: DNA
<213> ORGANISM: Homo sapiens
```

```
<220> FEATURE:
<221> NAME/KEY: misc_feature
<223> OTHER INFORMATION: Homo sapiens anaplastic lymphoma receptor
      tyrosine kinase (ALK), mRNA

<400> SEQUENCE: 4
gggggcggca gcggtggtag cagctggtac ctcccgccgc ctctgttcgg agggtcgcgg     60
ggcaccgagg tgcttccgg ccgccctctg gtcggccacc caaagccgcg ggcgctgatg    120
atgggtgagg aggggggcggc aagatttcgg gcgcccctgc cctgaacgcc ctcagctgct    180
gccgccgggg ccgctccagt gcctgcgaac tctgaggagc cgaggcgccg gtgagagcaa    240
ggacgctgca aacttgcgca gcgcgggggc tgggattcac gcccagaagt tcagcaggca    300
gacagtccga agccttcccg cagcggagag atagcttgag ggtgcgcaag acggcagcct    360
ccgccctcgg ttcccgccca gaccgggcag aagagcttgg aggagccaaa aggaacgcaa    420
aaggcggcca ggacagcgtg cagcagctgg gagccgccgt tctcagcctt aaaagttgca    480
gagattggag gctgccccga gagggacag accccagctc cgactgcggg ggcaggaga    540 ggacggtacc caactgccac ctcccttcaa ccatagtagt tcctctgtac cgagcgcagc    600
gagctacaga cggggggcgcg gcactcggcg cggagagcgg gaggctcaag gtcccagcca    660
gtgagcccag tgtgcttgag tgtctctgga ctcgcccctg agcttccagg tctgtttcat    720
ttagactcct gctcgcctcc gtgcagttgg gggaaaagcaa gagacttgcg cgcacgcaca    780
gtcctctgga gatcaggtgg aaggagccgc tgggtaccaa ggactgttca gagcctcttc    840
ccatctcggg gagagcgaag ggtgaggctg ggccccggaga gcagtgtaaa cggcctcctc    900
cggcgggatg ggagccatcg ggctcctgtg gctcctgccg ctgctgcttt ccacggcagc    960
tgtgggctcc gggatgggga ccggccagcg cgcgggctcc ccagctgcgg ggccgccgct   1020
gcagccccgg gagccactca gctactcgcg cctgcagagg aagagtctgg cagttgactt   1080
cgtggtgccc tcgctcttcc gtgtctacgc ccgggaccta ctgctgccac catcctcctc   1140
ggagctgaag gctggcaggc ccgaggcccg cggctcgcta gctctggact gcgccccgct   1200
gctcaggttg ctggggccgg cgccgggggt ctcctggacc gccggttcac cagccccggc   1260
agaggcccgg acgctgtcca gggtgctgaa gggcggctcc gtgcgcaagc tccggcgtgc   1320
caagcagttg gtgctggagc tgggcgagga ggcgatcttg gagggttgcg tcgggccccc   1380
cggggaggcg gctgtggggc tgctccagtt caatctcagc gagctgttca gttggtggat   1440
tcgccaaggc gaagggcgac tgaggatccg cctgatgccc gagaagaagg cgtcggaagt   1500
gggcagagag ggaaggctgt ccgcggcaat tcgcgcctcc cagccccgcc ttctcttcca   1560
gatcttcggg actggtcata gctccttgga atcaccaaca aacatgcctt ctccttctcc   1620
tgattatttt acatggaatc tcacctggat aatgaaagac tccttccctt tcctgtctca   1680
tcgcagccga tatggtctgg agtgcagctt tgacttcccc tgtgagctgg agtattcccc   1740
tccactgcat gacctcagga accagagctg gtcctggcgc cgcatcccct ccgaggaggc   1800
ctcccagatg gacttgctgg atgggcctgg ggcagagcgt tctaaggaga tgcccagagg   1860
ctcctttctc cttctcaaca cctcagctga ctccaagcac accatcctga gtccgtggat   1920
gaggagcagc agtgagcact gcacactggc cgtctcggtg cacaggcacc tgcagccctc   1980
tggaaggtac attgcccagc tgctgccca caacgaggct gcaagagaga tcctcctgat   2040
gcccactcca gggaagcatg gttggacagt gctccaggga agaatcgggc gtccagacaa   2100
cccatttcga gtggccctgg aatacatctc cagtggaaac cgcagcttgt ctgcagtgga   2160
```

```
cttctttgcc ctgaagaact gcagtgaagg aacatcccca ggctccaaga tggccctgca      2220
gagctccttc acttgttgga atgggacagt cctccagctt gggcaggcct gtgacttcca      2280
ccaggactgt gcccagggag aagatgagag ccagatgtgc cggaaactgc ctgtgggttt      2340
ttactgcaac tttgaagatg gcttctgtgg ctggacccaa ggcacactgt caccccacac      2400
tcctcaatgg caggtcagga ccctaaagga tgcccggttc caggaccacc aagaccatgc      2460
tctattgctc agtaccactg atgtccccgc ttctgaaagt gctacagtga ccagtgctac      2520
gtttcctgca ccgatcaaga gctctccatg tgagctccga atgtcctggc tcattcgtgg      2580
agtcttgagg ggaaacgtgt ccttggtgct agtggagaac aaaaccggga aggagcaagg      2640
caggatggtc tggcatgtcg ccgcctatga aggcttgagc ctgtggcagt ggatggtgtt      2700
gcctctcctc gatgtgtctg acaggttctg gctgcagatg gtcgcatggt ggggacaagg      2760
atccagagcc atcgtggctt ttgacaatat ctccatcagc ctggactgct acctcaccat      2820
tagcggagag acaagatcc tgcagaatac agcacccaaa tcaagaaacc tgtttgagag      2880
aaacccaaac aaggagctga aacccgggga aaattcacca agacagaccc ccatctttga      2940
ccctacagtt cattggctgt tcaccacatg tggggccagc gggccccatg gccccaccca      3000
ggcacagtgc aacaacgcct accagaactc caacctgagc gtggaggtgg ggagcgaggg      3060
cccccctgaaa ggcatccaga tctgaaggt gccagccacc gacacctaca gcatctcggg      3120
ctacggagct gctggcggga aaggcgggaa gaacaccatg atgcggtccc acggcgtgtc      3180
tgtgctgggc atcttcaacc tggagaagga tgacatgctg tacatcctgg ttgggcagca      3240
gggagaggac gcctgcccca gtacaaacca gttaatccag aaagtctgca ttggagagaa      3300
caatgtgata gaagaagaaa tccgtgtgaa cagaagcgtg catgagtggg caggaggcgg      3360
aggaggaggg ggtggagcca cctacgtatt taagatgaag gatggagtgc cggtgcccct      3420
gatcattgca gccggaggtg gtggcagggc ctacggggcc aagacagaca cgttccaccc      3480
agagagactg gagaataact cctcggttct agggctaaac ggcaattccg gagccgcagg      3540
tggtggaggt ggctggaatg ataacacttc cttgctctgg gccggaaaat ctttgcagga      3600
gggtgccacc ggaggacatt cctgccccca ggccatgaag aagtgggggt gggagacaag      3660
aggggggttttc ggaggggggtg gagggggggtg ctcctcaggt ggaggaggcg gaggatatat      3720
aggcggcaat gcagcctcaa acaatgaccc cgaaatggat ggggaagatg gggtttcctt      3780
catcagtcca ctgggcatcc tgtacacccc agctttaaaa gtgatggaag gccacgggga      3840
agtgaatatt aagcattatc taaactgcag tcactgtgag gtagacgaat gtcacatgga      3900
cccctgaaagc cacaaggtca tctgcttctg tgaccacggg acggtgctgg ctgaggatgg      3960
cgtctcctgc attgtgtcac ccaccccgga gccacacctg ccactctcgc tgatcctctc      4020
tgtggtgacc tctgccctcg tggccgccct ggtcctggct ttctcggca tcatgattgt      4080
gtaccgccgg aagcaccagg agctgcaagc catgcagatg gagctgcaga gccctgagta      4140
caagctgagc aagctccgca cctcgaccat catgaccgac tacaaccccca actactgctt      4200
tgctggcaag acctcctcca tcagtgacct gaaggaggtg ccgcggaaaa acatcaccct      4260
cattcggggt ctgggccatg cgccttttgg ggaggtgtat aaggccaggt gtccggaat       4320
gcccaacgac ccaagccccc tgcaagtggc tgtgaagacg ctgcctgaag tgtgctctga      4380
acaggacgaa ctggatttcc tcatggaagc cctgatcatc agcaaattca accaccagaa      4440
cattgttcgc tgcattgggg tgagcctgca atccctgccc cggttcatcc tgctggagct      4500
catggcgggg ggagaccctca agtccttcct ccgagagacc cgccctcgcc cgagccagcc      4560
```

-continued

```
ctcctccctg gccatgctgg accttctgca cgtggctcgg gacattgcct gtggctgtca    4620
gtatttggag gaaaaccact tcatccaccg agacattgct gccagaaact gcctcttgac    4680
ctgtccaggc cctggaagag tggccaagat tggagacttc gggatggccc gagacatcta    4740
cagggcgagc tactatagaa agggaggctg tgccatgctg ccagttaagt ggatgccccc    4800
agaggccttc atggaaggaa tattcacttc taaaacagac acatggtcct ttggagtgct    4860
gctatgggaa atcttttctc ttggatatat gccataccc  agcaaaagca accaggaagt    4920
tctggagttt gtcaccagtg gaggccggat ggacccaccc aagaactgcc ctgggcctgt    4980
ataccggata atgactcagt gctggcaaca tcagcctgaa gacaggccca actttgccat    5040
cattttggag aggattgaat actgcaccca ggacccggat gtaatcaaca ccgctttgcc    5100
gatagaatat ggtccacttg tggaagagga agagaaagtg cctgtgaggc ccaaggaccc    5160
tgaggggtt  cctcctctcc tggtctctca acaggcaaaa cgggaggagg agcgcagccc    5220
agctgcccca ccacctctgc ctaccacctc ctctggcaag gctgcaaaga aacccacagc    5280
tgcagagatc tctgttcgag tccctagagg gccggccgtg aaggggac  acgtgaatat    5340
ggcattctct cagtccaacc ctccttcgga gttgcacaag gtccacggat ccagaaacaa    5400
gcccaccagc ttgtggaacc caacgtacgg ctcctggttt acagagaaac ccaccaaaaa    5460
gaataatcct atagcaaaga aggagccaca cgacaggggt aacctgggc  tggagggaag    5520
ctgtactgtc ccacctaacg ttgcaactgg gagacttccg ggggcctcac tgctcctaga    5580
gccctcttcg ctgactgcca atatgaagga ggtacctctg ttcaggctac gtcacttccc    5640
ttgtgggaat gtcaattacg gctaccagca acagggcttg cccttagaag ccgctactgc    5700
ccctggagct ggtcattacg aggataccat tctgaaaagc aagaatagca tgaaccagcc    5760
tgggccctga gctcggtcgc acactcactt ctcttccttg ggatccctaa gaccgtggag    5820
gagagagagg caatggctcc ttcacaaacc agagaccaaa tgtcacgttt tgttttgtgc    5880
caacctattt tgaagtacca ccaaaaaagc tgtattttga aaatgcttta gaaaggtttt    5940
gagcatgggt tcatcctatt ctttcgaaag aagaaaatat cataaaaatg agtgataaat    6000
acaaggccca gatgtggttg cataaggttt ttatgcatgt ttgttgtata cttccttatg    6060
cttctttcaa attgtgtgtg ctctgcttca atgtagtcag aattagctgc ttctatgttt    6120
catagttggg gtcatagatg tttccttgcc ttgttgatgt ggacatgagc catttgaggg    6180
gagagggaac ggaaataaag gagttatttg taatgactaa aa                      6222
```